(12) United States Patent
Ise

(10) Patent No.: US 7,914,910 B2
(45) Date of Patent: Mar. 29, 2011

(54) ORGANIC ELECTROLUMINESCENCE DEVICE AND NOVEL ORGANIC COMPOUND CONTAINING SILICON SUBSTITUENT

(75) Inventor: Toshihiro Ise, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 308 days.

(21) Appl. No.: 12/324,278

(22) Filed: Nov. 26, 2008

(65) Prior Publication Data

US 2009/0134789 A1    May 28, 2009

(30) Foreign Application Priority Data

Nov. 27, 2007    (JP) ................................. 2007-306264

(51) Int. Cl.
*H01J 1/63* (2006.01)
*C07F 7/10* (2006.01)

(52) U.S. Cl. ........................... 428/690; 313/504; 546/14

(58) Field of Classification Search .................. None
See application file for complete search history.

(56) References Cited

U.S. PATENT DOCUMENTS

| 6,303,238 B1 | 10/2001 | Thompson et al. | |
| 2006/0008674 A1* | 1/2006 | Yu et al. ........................ | 428/690 |

FOREIGN PATENT DOCUMENTS

| JP | 2006-135160 A | 5/2006 |
| WO | 00/57676 A1 | 9/2000 |
| WO | 2004/095598 A2 | 11/2004 |
| WO | 2005/022962 A1 | 3/2005 |

OTHER PUBLICATIONS

Kaminorz et. al., OLEDs . . . oxadiazole derivatives, 2001, Synthetics Metals, vol. 122, pp. 115-118.*
Jun Ho Kim, et al., "Study on electrical characteristics of organic electrophosphorescent devices based on new Ir complex", Materials Science & Engineering, 2004, pp. 167-171, vol. 24, Elsevier B.V.

* cited by examiner

*Primary Examiner* — D. Lawrence Tarazano
*Assistant Examiner* — Gregory Clark
(74) *Attorney, Agent, or Firm* — Sughrue Mion, PLLC

(57) ABSTRACT

An organic electroluminescence device includes an anode; a cathode; and at least one organic layer, wherein the at least one organic layer includes a first organic layer which is a light-emitting layer being provided between the anode and the cathode and containing at least one light-emitting material, and the at least one organic layer contains at least one compound represented by formula (I):

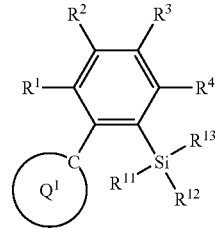

wherein $Q^1$ represents an aromatic heterocyclic ring; each of $R^1$, $R^2$, $R^3$ and $R^4$ independently represents a hydrogen atom or a substituent; and each of $R^{11}$, $R^{12}$ and $R^{13}$ independently represents an alkyl group, an aryl group, or an aromatic heterocyclic group, provided that at least one of $R^{11}$, $R^{12}$ and $R^{13}$ represents an aryl group or an aromatic heterocyclic group.

10 Claims, No Drawings

US 7,914,910 B2

ORGANIC ELECTROLUMINESCENCE DEVICE AND NOVEL ORGANIC COMPOUND CONTAINING SILICON SUBSTITUENT

BACKGROUND OF THE INVENTION

1. Field of the Invention

The present invention relates to an organic electroluminescence device capable of emitting light by converting electric energy to light, and also relates to a novel organic compound containing a silicon substituent.

2. Description of the Related Art

Since organic electroluminescence devices (hereinafter also referred to as "organic EL devices") are capable of obtaining emission of light of high luminance by low voltage driving, they are actively researched and developed. An organic electroluminescence device comprises a pair of electrodes and an organic layer between the pair of electrodes, electrons injected from the cathode and holes injected from the anode are recombined in the organic layer, and generated energy of exciton is used for emission of light.

In recent years, increment in efficiency of devices has been advanced by the use of phosphorescent materials. As the phosphorescent materials, inventions in connection with phosphorescent devices using iridium complexes and platinum complexes are used as the phosphorescent material are described in U.S. Pat. No. 6,303,238 and WO 00/57,676. However, devices that satisfy compatibility of high efficiency and high durability are not yet developed.

As host materials capable of forming a light-emitting layer together with phosphorescent materials, invention relating to organic electroluminescence devices using materials having a triphenylsilyl group for imparting aptitude for vacuum deposition and an amorphous property are described in WO 05/022,962 and WO 04/095,598. However, these materials are low in the lowest excitation triplet energy ($T_1$ energy) and when they are used with phosphorescent materials having emission of light in a blue region, they quench the emission of light of the phosphorescent materials to lower the luminous efficiency of the organic electroluminescence device. Therefore, these materials are inapplicable to a blue phosphorescent device, and further, they are low in charge injecting and transporting performances, so that the driving voltage of the device increases and the improvement is desired.

Invention concerning an organic electroluminescence device containing a compound represented by the following formula (F) is disclosed in JP-A-2006-135160 (The term "JP-A" as used herein refers to an "unexamined published Japanese patent application".), and as the specific examples of the compounds, compounds represented by formula (F-31) or (F-33) in which an aromatic heterocyclic ring and a trimethylsilyl group are substituted on the ortho-position of the benzene ring are exemplified. However, durability of the devices using these compounds is not sufficient, and further improvement is desired.

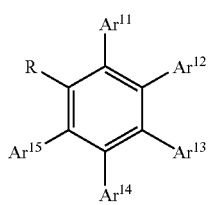

Formula (F)

In formula (F), each of $Ar^{11}$, $Ar^{12}$, $Ar^{13}$, $Ar^{14}$ and $Ar^{15}$ independently represents an aryl group or an aromatic heterocyclic group; and R represents a group selected from a hydrogen atom, an aliphatic hydrocarbon group, a fluoroalkyl group, a halogen atom, a sulfonyl group, a silyl group, and a cyano group. However, when R represents a hydrogen atom or an aliphatic hydrocarbon group, at least one of $Ar^{11}$, $Ar^{12}$, $Ar^{13}$, $Ar^{14}$ and $Ar^{15}$ represents an aryl group having one or more substituents having Hammett's σ para value of 0.05 or more.

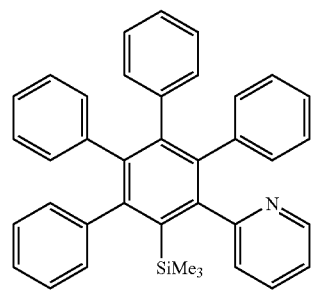

F-31

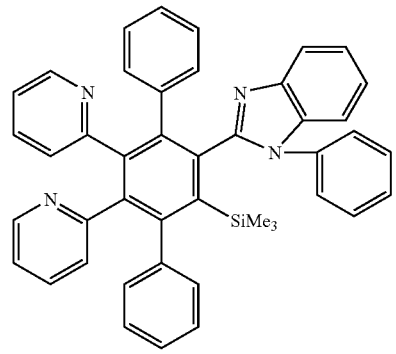

F-33

Further, an organic electroluminescence device using Alq (an aluminum complex of 8-hydroxyquinoline) as an electron transporting material for use in an electron-transporting layer of a phosphorescent device is disclosed in Materials, Science and Engineering, C24 pp. 167-171 (2004). However, Alq is low in $T_1$ energy and when Alq is used in a layer contiguous to a light-emitting layer, it quenches the emission of light of the phosphorescent materials to lower the luminous efficiency of the organic electroluminescence device. Therefore, materials high in $T_1$ energy and applicable to the layer are also desired.

SUMMARY OF THE INVENTION

An object of the invention is to provide an organic electroluminescence device high in luminance of emission of light, high in luminous efficiency, and high in durability. Another object is to provide an organic electroluminescence device having, in particular, emission in a blue region, which is high in emission luminance, high in luminous efficiency, and high in durability. A further object is to provide an organic compound having a silicon substituent preferred to provide the organic electroluminescence device.

As a result of intensive studies to solve the above problems, the present inventors have found that an organic electroluminescence device containing a compound having a special silicon substituent in an organic layer can solve the above problems. That is, the invention has been achieved by the following means.

(1) An organic electroluminescence device comprising:
  an anode;
  a cathode; and
  at least one organic layer,
  wherein
  the at least one organic layer comprises a first organic layer which is a light-emitting layer being provided between the anode and the cathode and containing at least one light-emitting material, and
  the at least one organic layer contains at least one compound represented by formula (I):

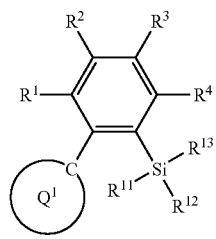

wherein
  $Q^1$ represents an aromatic heterocyclic ring;
  each of $R^1$, $R^2$, $R^3$ and $R^4$ independently represents a hydrogen atom or a substituent; and
  each of $R^{11}$, $R^{12}$ and $R^{13}$ independently represents an alkyl group, an aryl group, or an aromatic heterocyclic group, provided that at least one of $R^{11}$, $R^{12}$ and $R^{13}$ represents an aryl group or an aromatic heterocyclic group.
(2) The organic electroluminescence device as described in (1), wherein the compound represented by formula (I) is a compound represented by formula (II):

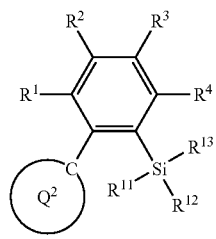

wherein
  $Q^2$ represents a nitrogen-containing aromatic heterocyclic ring;
  each of $R^1$, $R^2$, $R^3$ and $R^4$ independently represents a hydrogen atom or a substituent; and
  each of $R^{11}$, $R^{12}$ and $R^{13}$ independently represents an alkyl group, an aryl group, or an aromatic heterocyclic group, provided that at least one of $R^{11}$, $R^{12}$ and $R^{13}$ represents an aryl group or an aromatic heterocyclic group.
(3) The organic electroluminescence device as described in (1), wherein the light-emitting layer contains the compound represented by formula (I).
(4) The organic electroluminescence device as described in (1), wherein the at least one organic layer further comprises a second organic layer being provided between the light-emitting layer and the cathode, and the second organic layer contains the compound represented by formula (I).
(5) The organic electroluminescence device as described in (1), wherein the at least one light-emitting material comprises a phosphorescent material.
(6) The organic electroluminescence device as described in (1), wherein the at least one light-emitting material comprises a platinum complex or an iridium complex.
(7) The organic electroluminescence device as described in (6), wherein the platinum complex is a platinum complex having a tridentate or tetradentate ligand.
(8) The organic electroluminescence device as described in (7), wherein the platinum complex is represented by the following formula (C-1):

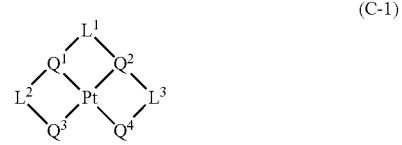

wherein
  each of $Q^1$, $Q^2$, $Q^3$ and $Q^4$ independently represents a ligand to coordinate to Pt; and
  each of $L^1$, $L^2$ and $L^3$ independently represents a single bond or a divalent linking group.
(9) A compound represented by the following formula (III):

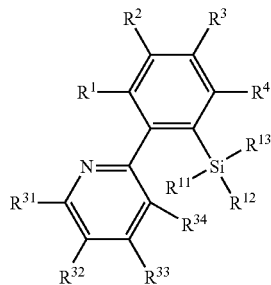

wherein
  each of $R^1$, $R^2$, $R^3$ and $R^4$ independently represents a hydrogen atom or a substituent;
  each of $R^{11}$, $R^{12}$ and $R^{13}$ independently represents an alkyl group, an aryl group, or an aromatic heterocyclic group, provided that at least one of $R^{11}$, $R^{12}$ and $R^{13}$ represents an aryl group or an aromatic heterocyclic group; and
  each of $R^{31}$, $R^{32}$, $R^{33}$ and $R^{34}$ independently represents a hydrogen atom or a substituent.
(10) A compound represented by the following formula (IV):

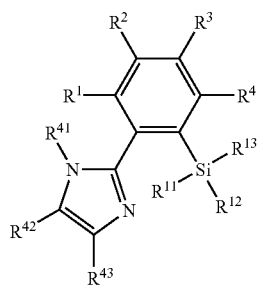

wherein
  each of $R^1$, $R^2$, $R^3$ and $R^4$ independently represents a hydrogen atom or a substituent;
  each of $R^{11}$, $R^{12}$ and $R^{13}$ independently represents an alkyl group, an aryl group, or an aromatic heterocyclic group, provided that at least one of $R^{11}$, $R^{12}$ and $R^{13}$ represents an aryl group or an aromatic heterocyclic group;

$R^{41}$ represents an alkyl group, an aryl group, or an aromatic heterocyclic group; and each of $R^{42}$ and $R^{43}$ independently represents a hydrogen atom or a substituent.

DETAILED DESCRIPTION OF THE INVENTION

The organic electroluminescence device in the invention is an organic electroluminescence device comprising: an anode; a cathode; and at least one organic layer, wherein the at least one organic layer comprises a light-emitting layer being provided between the anode and the cathode and containing at least one light-emitting material, and the at least one organic layer contains at least one compound represented by formula (I):

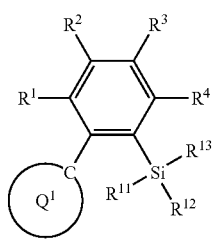

Formula (I)

In formula (I), $Q^1$ represents an aromatic heterocyclic ring; each of $R^1$, $R^2$, $R^3$ and $R^4$ independently represents a hydrogen atom or a substituent; and each of $R^{11}$, $R^{12}$ and $R^{13}$ independently represents an alkyl group, an aryl group, or an aromatic heterocyclic group, provided that at least one of $R^{11}$, $R^{12}$ and $R^{13}$ represents an aryl group or an aromatic heterocyclic group.

That is, the organic electroluminescence device in the invention has at least one light-emitting layer as the organic layer. Further, as the organic layers other than the light-emitting layer, a hole injecting layer, a hole transporting layer, an electron-blocking layer, an exciton-blocking layer, a hole-blocking layer, an electron transporting layer, an electron injecting layer, and a protective layer may be arbitrarily arranged, and each layer may unite functions of other layers. Further, each layer may be composed of a plurality of layers.

The organic electroluminescence device in the invention may be the one utilizing emission of light from singlet excited state (fluorescence), or may be the one utilizing emission of light from triplet excited state (phosphorescence), but the one using phosphorescence is preferred from the viewpoint of luminous efficiency.

The light-emitting layer of the organic electroluminescence device in the invention is preferably composed of at least one light-emitting material and at least one host material. Here, the host material means a material other than the light-emitting material of the materials constituting the light-emitting layer, which has at least one function of a function of dispersing a light-emitting material and maintaining the dispersion in the light-emitting layer, a function of receiving holes from the anode and a hole transporting layer, a function of receiving electrons from the cathode and an electron transporting layer, a function of transporting at least one of holes and electrons, a function of offering the place of recombination of holes and electrons, a function of transporting the energy of exciton generated by the recombination to the light-emitting material, and a function of transporting at least one of holes and electrons to the light-emitting material.

The compounds of the invention may be contained in any layer of the organic layers, and may be contained in a plurality of layers, but they are preferably contained in a hole injecting layer, a hole transporting layer, an electron blocking layer, a light-emitting layer, a hole blocking layer, an electron transporting layer, or an electron injecting layer, more preferably contained in a light-emitting layer, a hole blocking layer, an electron transporting layer, or an electron injecting layer, still more preferably contained in a light-emitting layer, and most preferably contained in a light-emitting layer as host materials. When the compounds of the invention are contained in a light-emitting layer as host materials, the content of the compounds of the invention in the light-emitting layer is preferably from 50 to 99.9 mass %, and more preferably from 60 to 99 mass %. Further, when the compounds of the invention are contained in a hole injecting layer, a hole transporting layer, an electron blocking layer, a hole blocking layer, an electron transporting layer, or an electron injecting layer, the content of the compounds of the invention in each layer is preferably from 70 to 100%, more preferably from 85 to 100%, and most preferably from 99 to 100%. Further, when an electron transporting layer consists of two or more layers, it is sufficient for any one layer to contain the compounds of the invention.

The compound represented by formula (I) is explained below.

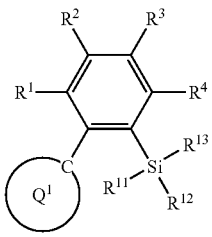

Formula (I)

In formula (I), $Q^1$ represents an aromatic heterocyclic ring; each $R^1$, $R^2$, $R^3$ and $R^4$ independently represents a hydrogen atom or a substituent; and each of $R^{11}$, $R^{12}$ and $R^{13}$ independently represents an alkyl group, an aryl group, or an aromatic heterocyclic group, provided that at least one of $R^{11}$, $R^{12}$ and $R^{13}$ represents an aryl group or an aromatic heterocyclic group.

$Q^1$ represents an aromatic heterocyclic ring. The aromatic heterocyclic ring in the invention means an aromatic ring containing at least one hetero atom. Further, the aromatic heterocyclic group means a group formed by elimination of the hydrogen atom bonding to the aromatic heterocyclic ring.

As the aromatic heterocyclic ring represented by $Q^1$, a nitrogen-containing heterocyclic 5-membered ring, a nitrogen-containing heterocyclic 6-membered ring, an oxygen-containing heterocyclic 5-membered ring, and a sulfur-containing heterocyclic 5-membered ring are exemplified, and as the specific examples, a pyridine ring, a pyrazine ring, a pyrimidine ring, a pyridazine ring, a 1,2,4-triazine ring, a 1,3,5-triazine ring, a pyrrole ring, a pyrazole ring, an imidazole ring, a 1,2,3-triazole ring, a 1,2,4-triazole ring, a furan ring, a thiophene ring, an oxazole ring, an isoxazole ring, a thiazole ring, an isothiazole ring, a 1,2,3-oxadiazole ring, a 1,2,4-oxadiazole ring, a 1,3,4-oxadiazole ring, a 1,2,3-thiadiazole ring, a 1,2,4-thiadiazole ring, a 1,3,4-thiadiazole ring, a selenophene ring, and a tellurophene ring are exemplified. From the aspects of a charge transporting property and driving durability of the device, considering the stability of mother nucleus of an aromatic ring, the ionization potential of a film, control of affinity of electrons, and expanse of π electron system, a pyridine ring, a pyrazine ring, a pyrimidine ring, a pyridazine ring, a 1,3,5-triazine ring, a pyrrole ring, a pyrazole ring, an imidazole ring, a 1,2,4-triazole ring, a furan ring, a thiophene ring, an oxazole ring, a thiazole ring, a 1,3,4-oxadiazole ring, and a 1,3,4-thiadiazole ring are preferred, a pyridine ring, a pyrimidine ring, a pyrazine ring, a 1,3,5-triazine ring, a pyrazole ring, an imidazole ring, an oxazole ring, a thiazole ring, and a thiophene ring are more preferred, a pyridine ring, a pyrimidine ring, a pyrazine ring, an imidazole ring, a pyrazole ring, an oxazole ring, and a thiazole ring are still more preferred, a pyridine ring, a pyrazine ring, and an imidazole ring are still further preferred, and a pyridine ring and an imidazole ring are especially preferred.

$Q^1$ may have a substituent, and as the substituents of $Q^1$, the substituents selected from the following substituent group A are exemplified. When $Q^1$ has two or more substituents, these substituents may be the same with or different from each other.

Substituent Group A:

A alkyl group (preferably having from 1 to 30 carbon atoms, more preferably from 1 to 20 carbon atoms, and especially preferably from 1 to 10 carbon atoms, e.g., methyl, ethyl, isopropyl, tert-butyl, n-octyl, n-decyl, n-hexadecyl, cyclopropyl, cyclopentyl, cyclohexyl, etc., are exemplified), an alkenyl group (preferably having from 2 to 30 carbon atoms, more preferably from 2 to 20 carbon atoms, and especially preferably from 2 to 10 carbon atoms, e.g., vinyl, allyl, 2-butenyl, 3-pentenyl, etc., are exemplified), an alkynyl group (preferably having from 2 to 30 carbon atoms, more preferably from 2 to 20 carbon atoms, and especially preferably from 2 to 10 carbon atoms, e g., propargyl, 3-pentynyl, etc., are exemplified), an aryl group (preferably having from 6 to 30 carbon atoms, more preferably from 6 to 20 carbon atoms, and especially preferably from 6 to 12 carbon atoms, e.g., phenyl, p-methylphenyl, naphthyl, anthranyl, etc., are exemplified), an amino group (preferably having from 0 to 30 carbon atoms, more preferably from 0 to 20 carbon atoms, and especially preferably from 0 to 10 carbon atoms, e.g., amino, methylamino, dimethylamino, diethylamino, dibenzylamino, diphenylamino, ditolylamino, etc., are exemplified), an alkoxy group (preferably having from 1 to 30 carbon atoms, more preferably from 1 to 20 carbon atoms, and especially preferably from 1 to 10 carbon atoms, e.g., methoxy, ethoxy, butoxy, 2-ethylhexyloxy, etc., are exemplified), an aryloxy group (preferably having from 6 to 30 carbon atoms, more preferably from 6 to 20 carbon atoms, and especially preferably from 6 to 12 carbon atoms, e.g., phenyloxy, 1-naphthyloxy, 2-naphthyloxy, etc., are exemplified), a heterocyclic oxy group (preferably having from 1 to 30 carbon atoms, more preferably from 1 to 20 carbon atoms, and especially preferably from 1 to 12 carbon atoms, e.g., pyridyloxy, pyrazyloxy, pyrimidyloxy, quinolyloxy, etc., are exemplified), an acyl group (preferably having from 2 to 30 carbon atoms, more preferably from 2 to 20 carbon atoms, and especially preferably from 2 to 12 carbon atoms, e.g., acetyl, benzoyl, formyl, pivaloyl, etc., are exemplified), an alkoxycarbonyl group (preferably having from 2 to 30 carbon atoms, more preferably from 2 to 20 carbon atoms, and especially preferably from 2 to 12 carbon atoms, e.g., methoxycarbonyl, ethoxycarbonyl, etc., are exemplified), an aryloxycarbonyl group (preferably having from 7 to 30 carbon atoms, more preferably from 7 to 20 carbon atoms, and especially preferably from 7 to 12 carbon atoms, e.g., phenyloxycarbonyl, etc., are exemplified), an acyloxy group (preferably having from 2 to 30 carbon atoms, more preferably from 2 to 20 carbon atoms, and especially preferably from 2 to 10 carbon atoms, e.g., acetoxy, benzoyloxy, etc., are exemplified), an acylamino group (preferably having from 2 to 30 carbon atoms, more preferably from 2 to 20 carbon atoms, and especially preferably from 2 to 10 carbon atoms, e.g., acetylamino, benzoylamino, etc., are exemplified), an alkoxycarbonylamino group (preferably having from 2 to 30 carbon atoms, more preferably from 2 to 20 carbon atoms, and especially preferably from 2 to 12 carbon atoms, e.g., methoxycarbonylamino, etc., are exemplified), an aryloxycarbonylamino group (preferably having from 7 to 30 carbon atoms, more preferably from 7 to 20 carbon atoms, and especially preferably from 7 to 12 carbon atoms, e.g., phenyloxycarbonylamino, etc., are exemplified), a sulfonylamino group (preferably having from 1 to 30 carbon atoms, more preferably from 1 to 20 carbon atoms, and especially preferably from 1 to 12 carbon atoms, e.g., methanesulfonylamino, benzenesulfonylamino, etc., are exemplified), a sulfamoyl group (preferably having from 0 to 30 carbon atoms, more preferably from 0 to 20 carbon atoms, and especially preferably from 0 to 12 carbon atoms, e.g., sulfamoyl, methylsulfamoyl, dimethylsulfamoyl, phenylsulfamoyl, etc., are exemplified), a carbamoyl group (preferably having from 1 to 30 carbon atoms, more preferably from 1 to 20 carbon atoms, and especially preferably from 1 to 12 carbon atoms, e.g., carbamoyl, methylcarbamoyl, diethylcarbamoyl, phenylcarbamoyl, etc., are exemplified), an alkylthio group (preferably having from 1 to 30 carbon atoms, more preferably from 1 to 20 carbon atoms, and especially preferably from 1 to 12 carbon atoms, e.g., methylthio, ethylthio, etc., are exemplified), an arylthio group (preferably having from 6 to 30 carbon atoms, more preferably from 6 to 20 carbon atoms, and especially preferably from 6 to 12 carbon atoms, e.g., phenylthio, etc., are exemplified), a heterocyclic thio group (preferably having from 1 to 30 carbon atoms, more preferably from 1 to 20 carbon atoms, and especially preferably from 1 to 12 carbon atoms, e.g., pyridylthio, 2-benzimizolylthio, 2-benzoxazolylthio, 2-benzothiazolylthio, etc., are exemplified), a sulfonyl group (preferably having from 1 to 30 carbon atoms, more preferably from 1 to 20 carbon atoms, and especially preferably from 1 to 12 carbon atoms, e.g., mesyl, tosyl, etc., are exemplified), a sulfinyl group (preferably having from 1 to 30 carbon atoms, more preferably from 1 to 20 carbon atoms, and especially preferably from 1 to 12 carbon atoms, e.g., methanesulfinyl, benzenesulfinyl, etc., are exemplified), a ureido group (preferably having from 1 to 30 carbon atoms, more preferably from 1 to 20 carbon atoms, and especially preferably from 1 to 12 carbon atoms, e.g., ureido, methylureido, phenylureido, etc., are exemplified), a phosphoric acid amido group (preferably having from 1 to 30 carbon atoms, more preferably from 1 to 20 carbon atoms, and especially preferably from 1 to 12 carbon atoms, e.g., diethylphosphoric acid amido, phenylphosphoric acid amido, etc., are exemplified), a hydroxyl group, a mercapto group, a halogen atom (e.g., a fluorine atom, a chlorine atom, a bromine atom, an iodine atom), a cyano group, a sulfo group, a carboxyl group, a nitro group, a hydroxamic acid group, a sulfino group, a hydrazino group, an imino group, a heterocyclic group (also including an aromatic heterocyclic group, preferably having from 1 to 30 carbon atoms, and more preferably from 1 to 12 carbon atoms, and as the hetero atoms, e.g., a nitrogen atom, an oxygen atom, a sulfur atom, a phosphorus atom, a silicon atom, a selenium atom, and a tellurium atom are exemplified, specifically, e.g., pyridyl, pyrazinyl, pyrimidyl, pyridazinyl, pyrrolyl, pyrazolyl, triazolyl, imidazolyl, oxazolyl, thiazolyl, isoxazolyl, isothiazolyl, quinolyl, furyl, thienyl, selenophenyl, tellurophenyl, piperidyl, piperidino, morpholino, pyrrolidyl, pyrrolidino, benzoxazolyl, benzimidazolyl, benzothiazolyl, a carbazolyl group, an azepinyl group, a silolyl group, etc., are exemplified), a silyl group (preferably having from 3 to 40 carbon atoms, more preferably from 3 to 30 carbon atoms, and especially preferably from 3 to 24 carbon atoms, e.g., trimethylsilyl, triphenylsilyl, etc., are exemplified), a silyloxy group (preferably having from 3 to 40 carbon atoms, more preferably from 3 to 30 carbon atoms, and especially preferably from 3 to 24 carbon atoms, e.g., trimethylsilyloxy, triphenylsilyloxy, etc., are exemplified), and a phosphoryl group (e.g., a diphenylphosphoryl group, a dimethylphosphoryl group, etc., are exemplified) are exemplified. These substituents may further be substituted, and the substituents selected from substituent group A described above can be exemplified as further substituents.

In the invention, the above "carbon atom numbers" of the substituent of, e.g., an alkyl group, etc. also include the case where the substituent of the alkyl group, etc., may further be substituted with other substituents, and the terminology is used to also include the carbon atom numbers of such other substituents.

The aromatic heterocyclic ring represented by $Q^1$ may further form a condensed ring with other rings. As the rings to be condensed, a benzene ring, a pyridine ring, a pyrazine ring, a pyrimidine ring, a pyridazine ring, a pyrrole ring, a pyrazole ring, an imidazole ring, a 1,2,4-triazole ring, an oxazole ring, a thiazole ring, a furan ring, a thiophene ring, a selenophene ring, a tellurophene ring, a silole ring, a germole ring, a phosphor ring, etc., are exemplified. From the aspects of a charge transporting property and driving durability of the device, considering the stability of mother nucleus of an aromatic ring, the ionization potential of a film, control of affinity of electrons, and expanse of π electron system, a benzene ring, a pyridine ring, a pyrazine ring, an imidazole ring, an oxazole ring, and a thiophene ring are preferred, a benzene ring, a pyrazine ring and an imidazole ring are more preferred, and a benzene ring and a pyridine ring are still more preferred.

These above substituents and condensed rings may further have a substituent, and may further be condensed with other rings.

Each of $R^1$, $R^2$, $R^3$ and $R^4$ independently represents a hydrogen atom or a substituent. As the substituents represented by $R^1$, $R^2$, $R^3$ and $R^4$, substituent group A described above can be independently applied. From the aspects of a charge transporting property and driving durability of the device, taking bulkiness of substituents and electronic disturbance into consideration, each of $R^1$, $R^2$, $R^3$ and $R^4$ preferably represents a hydrogen atom, an alkyl group, an aryl group, an aromatic heterocyclic group, an alkoxy group, an amino group, a silyl group, a fluorine group, or a cyano group, more preferably represents a hydrogen atom, an alkyl group, an aryl group, or an aromatic heterocyclic group, still more preferably represents a hydrogen atom or an alkyl group, and especially preferably represents a hydrogen atom. Further, it is a preferred embodiment that at least one of $R^1$, $R^2$, $R^3$ and $R^4$ represents a hydrogen atom, or a substituent other than an aryl group or an aromatic heterocyclic group. That is, an embodiment that not all of $R^1$, $R^2$, $R^3$ and $R^4$ represent an aryl group or an aromatic heterocyclic group is preferred. More preferably, at least one of $R^1$, $R^2$, $R^3$ and $R^4$ is selected from the group consisting of a hydrogen atom, an alkyl group, an alkoxy group, an amino group, a silyl group, a fluorine group and a cyano group, still more preferably, from the viewpoint of retaining the lowest excitation triplet energy high, at least one of $R^1$, $R^2$, $R^3$ and $R^4$ is selected from the group consisting of a hydrogen atom and an alkyl group, and most preferably $R^1$, $R^2$, $R^3$ and $R^4$ are all hydrogen atoms.

Each of $R^{11}$, $R^{12}$ and $R^{13}$ independently represents an alkyl group, an aryl group, or an aromatic heterocyclic group, provided that at least one of $R^{11}$, $R^{12}$ and $R^{13}$ represents an aryl group or an aromatic heterocyclic group. As the alkyl groups, a methyl group, an ethyl group, an isopropyl group, a tert-butyl group, an n-octyl group, an n-decyl group, an n-hexadecyl group, a cyclopropyl group, a cyclopentyl group, and a cyclohexyl group are exemplified, preferably a methyl group, an ethyl group, and an isopropyl group. As the aryl group and the aromatic heterocyclic group, a phenyl group, a pyridyl group, a pyrazinyl group, a pyrimidinyl group, an imidazolyl group, an oxazolyl group, a thiazolyl group, a pyrazolyl group, a thienyl group, a furyl group, etc., are exemplified. From the viewpoint of driving durability of the device, the substituent on the silyl group is preferably bulky, and from the aspect of a charge transporting property, considering the potential of a mother nucleus and expanse of π electron system, a phenyl group and a pyridyl group are preferred, and a phenyl group is more preferred.

From the points of a charge transporting property and driving durability of the device, as the groups represented by $R^{11}$, $R^{12}$ and $R^{13}$ and a silicon atom, preferably a triphenylsilyl group, a dimethylphenylsilyl group, a methyldiphenylsilyl group, an ethyldiphenylsilyl group, and an isopropyldiphenylsilyl group are exemplified, more preferably a triphenylsilyl group and a dimethylphenylsilyl group, and still more preferably a triphenylsilyl group.

From the aspects of a charge transporting property and driving durability of the device, considering the stability of a mother nucleus of an aromatic ring, the ionization potential of a film, the control of affinity of electrons, and expanse of π electron system, the compound represented by formula (I) is more preferably a compound represented by formula (II). The compound represented by formula (II) will be described below.

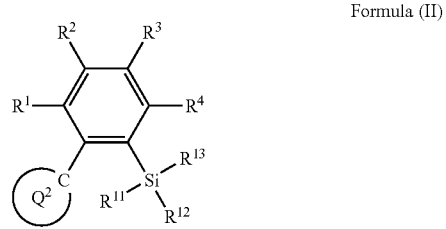

Formula (II)

In formula (II), $Q^2$ represents a nitrogen-containing aromatic heterocyclic ring; each of $R^1$, $R^2$, $R^3$ and $R^4$ independently represents a hydrogen atom or a substituent; and each of $R^{11}$, $R^{12}$ and $R^{13}$ independently represents an alkyl group, an aryl group, or an aromatic heterocyclic group, provided that at least one of $R^{11}$, $R^{12}$ and $R^{13}$ represents an aryl group or an aromatic heterocyclic group.

Q2 represents a nitrogen-containing aromatic heterocyclic ring. As the examples of the nitrogen-containing aromatic heterocyclic rings represented by $Q^2$, from the aspects of a charge transporting property and driving durability of the device, considering the stability of a mother nucleus of an aromatic ring, the ionization potential of a film, the control of affinity of electrons, and expanse of π electron system, a pyridine ring, a pyrazine ring, a pyrimidine ring, a pyridazine ring, a 1,2,4-triazine ring, a 1,3,5-triazine ring, a pyrrole ring, a pyrazole ring, an imidazole ring, a 1,2,3-triazole ring, a 1,2,4-triazole ring, an oxazole ring, an isoxazole ring, a thiazole ring, an isothiazole ring, a 1,2,3-oxadiazole ring, a 1,2,4-oxadiazole ring, a 1,3,4-oxadiazole ring, a 1,2,3-thiadiazole ring, a 1,2,4-thiadiazole ring, and a 1,3,4-thiadiazole ring are exemplified, preferably a pyridine ring, a pyrazine ring, a pyrimidine ring, a pyridazine ring, a 1,3,5-triazine ring, a pyrrole ring, a pyrazole ring, an imidazole ring, a 1,2,4-triazole ring, an oxazole ring, a thiazole ring, a 1,3,4-oxadiazole ring, and a 1,3,4-thiadiazole ring are exemplified, more preferably a pyridine ring, a pyrimidine ring, a pyrazine ring, a 1,3,5-triazine ring, a pyrazole ring, an imidazole ring, an oxazole ring, and a thiazole ring are exemplified, still more preferably a pyridine ring, a pyrimidine ring, a pyrazine ring, an imidazole ring, a pyrazole ring, an oxazole ring, and a thiazole ring, still yet preferably a pyridine ring, a pyrazine ring, and an imidazole ring, and especially preferably a pyridine ring and an imidazole ring are exemplified.

$Q^2$ may have a substituent, and the above substituent group A can be exemplified as the examples of the substituents of $Q^2$. The embodiment of the substituents of $Q^2$ is the same as that of $Q^1$.

The nitrogen-containing aromatic heterocyclic ring represented by $Q^2$ may further form a condensed ring with other rings. As the rings to be condensed, the rings exemplified above as the condensed rings formed by the aromatic heterocyclic rings represented by $Q^1$ are applicable. The embodiment of these condensed rings is the same as that of $Q^1$.

Each of the above substituents and condensed rings may further have a substituent, or may further be condensed with other rings.

$R^1$, $R^2$, $R^3$, $R^4$, $R^{11}$, $R^{12}$ and $R^{13}$ have the same definitions as those in formula (I), and preferred ranges are also the same.

From the aspects of a charge transporting property and driving durability of the device, considering the stability of a mother nucleus of an aromatic ring, the ionization potential of a film, the control of affinity of electrons, and expanse of π electron system, the compound represented by formula (II) is preferably a compound represented by the following formula (III). The compound represented by formula (III) will be described below.

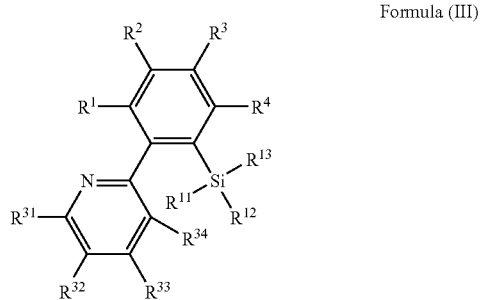

Formula (III)

In formula (III), each of $R^1$, $R^2$, $R^3$ and $R^4$ independently represents a hydrogen atom or a substituent; each of $R^{11}$, $R^{12}$ and $R^{13}$ independently represents an alkyl group, an aryl group, or an aromatic heterocyclic group, provided that at least one of $R^{11}$, $R^{12}$ and $R^{13}$ represents an aryl group or an aromatic heterocyclic group; and each of $R^{31}$, $R^{32}$, $R^{33}$ and $R^{34}$ independently represents a hydrogen atom or a substituent.

$R^1$, $R^2$, $R^3$, $R^4$, $R^{11}$, $R^{12}$ and $R^{13}$ have the same definitions as those in formula (I), and preferred ranges are also the same.

Each of $R^{31}$, $R^{32}$, $R^{33}$ and $R^{34}$ independently represents a hydrogen atom or a substituent. Each of the substituents exemplified above as substituent group A can be independently applied to the substituents represented by $R^{31}$, $R^{32}$, $R^{33}$ and $R^{34}$. Each of $R^{31}$, $R^{32}$, $R^{33}$ and $R^{34}$ preferably represents a hydrogen atom, an alkyl group, an aryl group, an aromatic heterocyclic group, an alkoxy group, an amino group, a silyl group, a fluorine group, or a cyano group, more preferably represents a hydrogen atom, an alkyl group, an aryl group, or an aromatic heterocyclic group, still more preferably a hydrogen atom, an alkyl group, or an aryl group, and especially preferably a hydrogen atom.

From the aspects of a charge transporting property and driving durability of the device, considering the stability of a mother nucleus of an aromatic ring, the ionization potential of a film, the control of affinity of electrons, and expanse of π electron system, the compound represented by formula (II) is a compound represented by the following formula (IV) as another preferred embodiment. The compound represented by formula (IV) will be described below.

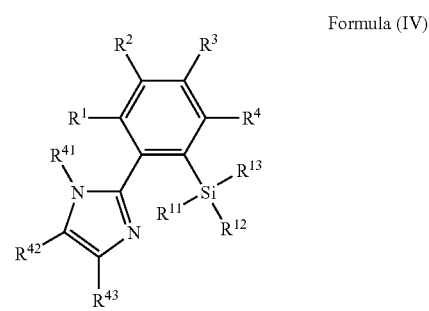

Formula (IV)

In formula (IV), each of $R^1$, $R^2$, $R^3$ and $R^4$ independently represents a hydrogen atom or a substituent; each of $R^{11}$, $R^{12}$ and $R^{13}$ independently represents an alkyl group, an aryl group, or an aromatic heterocyclic group, provided that at least one of $R^{11}$, $R^{12}$ and $R^{13}$ represents an aryl group or an aromatic heterocyclic group; $R^{41}$ represents an alkyl group, an aryl group, or an aromatic heterocyclic group; and each of $R^{42}$ and $R^{43}$ independently represents a hydrogen atom or a substituent.

$R^1$, $R^2$, $R^3$, $R^4$, $R^{11}$, $R^{12}$ and $R^{13}$ have the same definitions as those in formula (I), and preferred ranges are also the same.

$R^{41}$ represents an alkyl group, an aryl group, or an aromatic heterocyclic group. $R^{41}$ preferably represents an aryl group, and more preferably a phenyl group. The alkyl group, aryl group, or aromatic heterocyclic group represented by $R^{41}$ may each have a substituent, and the above substituent group A can be applied to the substituents.

Each of $R^{42}$ and $R^{43}$ independently represents a hydrogen atom or a substituent. Each of the substituents exemplified above as substituent group A can be independently applied to the substituents represented by $R^{42}$ and $R^{43}$. Each of $R^{42}$ and $R^{43}$ preferably represents an alkyl group, an aryl group, an aromatic heterocyclic group, a silyl group, a cyano group, a fluorine group, or a group to form an aromatic ring or an aromatic heterocyclic ring by linking $R^{42}$ and $R^{43}$, more preferably an aryl group, a cyano group, or a group to form an aromatic ring or an aromatic heterocyclic ring by linking $R^{42}$ and $R^{43}$, still more preferably a group to form an aromatic ring or an aromatic heterocyclic ring by linking $R^{42}$ and $R^{43}$, and still yet preferably a group to form a benzene ring, a pyridine ring or a pyrazine ring by linking $R^{42}$ and $R^{43}$.

From the aspects of a charge transporting property and driving durability of the device, considering the stability of a mother nucleus of an aromatic ring, the ionization potential of a film, the control of affinity of electrons, and expanse of π electron system, the compound represented by formula (III) is a compound represented by the following formula (V) as a preferred embodiment. The compound represented by formula (V) will be described below.

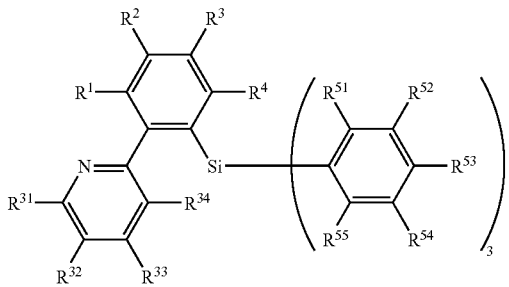

Formula (V)

In formula (V), each of $R^1$, $R^2$, $R^3$ and $R^4$ independently represents a hydrogen atom or a substituent; and each of $R^{31}$, $R^{32}$, $R^{33}$, $R^{34}$, $R^{51}$, $R^{52}$, $R^{53}$, $R^{54}$ and $R^{55}$ independently represents a hydrogen atom or a substituent.

$R^1$, $R^2$, $R^3$ and $R^4$ have the same definitions as those in formula (I), and preferred ranges are also the same.

$R^{31}$, $R^{32}$, $R^{33}$ and $R^{34}$ have the same definitions as those in formula (III), and preferred ranges are also the same.

Each of $R^{51}$, $R^{52}$, $R^{53}$, $R^{54}$ and $R^{55}$ independently represents a hydrogen atom or a substituent. Each of the substituents exemplified above as substituent group A can be independently applied to the substituents represented by $R^{51}$, $R^{52}$, $R^{53}$, $R^{54}$ and $R^{55}$. Each of $R^{51}$, $R^{52}$, $R^{53}$, $R^{54}$ and $R^{55}$ preferably represents a hydrogen atom, an alkyl group, an aryl group, an aromatic heterocyclic group, an alkoxy group, an amino group, a silyl group, a fluorine group, or a cyano group, more preferably represents a hydrogen atom, an alkyl group, an aryl group, or an aromatic heterocyclic group, still more preferably a hydrogen atom, an alkyl group, or an aryl group, and especially preferably a hydrogen atom.

From the aspects of a charge transporting property and driving durability of the device, considering the stability of a mother nucleus of an aromatic ring, the ionization potential of a film, the control of affinity of electrons, and expanse of π electron system, the compound represented by formula (IV) is a compound represented by the following formula (VI) as a preferred embodiment. The compound represented by formula (VI) will be described below.

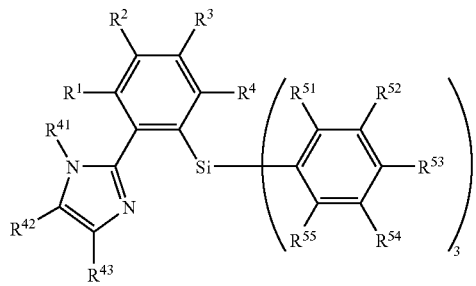

Formula (VI)

In formula (VI), each of $R^1$, $R^2$, $R^3$ and $R^4$ independently represents a hydrogen atom or a substituent; $R^{41}$ represents an alkyl group, an aryl group, or an aromatic heterocyclic group; each of $R^{42}$ and $R^{43}$ independently represents a hydrogen atom or a substituent; and each of $R^{51}$, $R^{52}$, $R^{53}$, $R^{54}$ and $R^{55}$ independently represents a hydrogen atom or a substituent.

$R^1$, $R^2$, $R^3$ and $R^4$ have the same definitions as those in formula (I), and preferred ranges are also the same. $R^{41}$, $R^{42}$ and $R^{43}$ have the same definitions as those in formula (IV), and preferred ranges are also the same. $R^{51}$, $R^{52}$, $R^{53}$, $R^{54}$ and $R^{55}$ have the same definitions as those in formula (V), and preferred ranges are also the same.

From the aspects of a charge transporting property and driving durability of the device, considering the stability of a mother nucleus of an aromatic ring, the ionization potential of a film, the control of affinity of electrons, and expanse of π electron system, the compound represented by formula (VI) is a compound represented by the following formula (VII) as a preferred embodiment. The compound represented by formula (VII) will be described below.

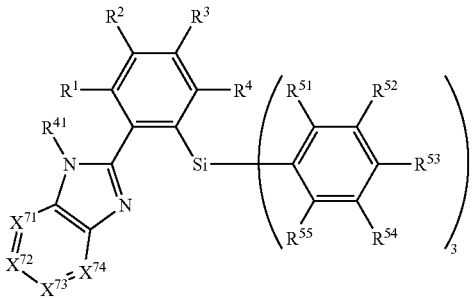

Formula (VII)

In formula (VII), each of $R^1$, $R^2$, $R^3$ and $R^4$ independently represents a hydrogen atom or a substituent; $R^{41}$ represents an alkyl group, an aryl group, or an aromatic heterocyclic group; each of $R^{51}$, $R^{52}$, $R^{53}$, $R^{54}$ and $R^{55}$ independently represents a hydrogen atom or a substituent; and each of $X^{71}$, $X^{72}$, $X^{73}$ and $X^{74}$ independently represents a nitrogen atom, or a substituted or unsubstituted carbon atom.

$R^1$, $R^2$, $R^3$ and $R^4$ have the same definitions as those in formula (I), and preferred ranges are also the same. $R^{41}$ has the same definition as that in formula (IV), and a preferred range is also the same. $R^{51}$, $R^{52}$, $R^{53}$, $R^{54}$ and $R^{55}$ have the same definitions as those in formula (V), and preferred ranges are also the same. Each of $X^{71}$, $X^{72}$, $X^{73}$ and $X^{74}$ independently represents a nitrogen atom, or a substituted or unsubstituted carbon atom. When each of $X^{71}$, $X^{72}$, $X^{73}$ and $X^{74}$ represents a substituted carbon atom, each of the substituents exemplified above as substituent group A can be independently applied to the substituents. From the aspects of a charge transporting property and driving durability of the device, considering the stability of a mother nucleus of an aromatic ring, the ionization potential of a film, the control of affinity of electrons, and expanse of π electron system, the combination of a nitrogen atom and an unsubstituted carbon atom is preferred as $X^{71}$, $X^{72}$, $X^{73}$ and $X^{74}$, and the number of the nitrogen atom is preferably 1 or 2.

The compound represented by formula (I) may be a low molecular weight compound, or may be a polymer compound having a residue structure connected to the main chain of the polymer (preferably having a mass average molecular weight of from 1,000 to 5,000,000, more preferably from 5,000 to 2,000,000, and still more preferably from 10,000 to 1,000, 000), or may be a polymer compound having the structure of the compound represented by formula (I) of the invention at the main chain (preferably having a mass average molecular weight of from 1,000 to 5,000,000, more preferably from 5,000 to 2,000,000, and still more preferably from 10,000 to 1,000,000). When the compound is a polymer compound, it may be a homopolymer, or may be a copolymer with other polymer, and when the compound is a copolymer, it may be a random copolymer or may be a block copolymer. Further, in the case of a copolymer, it may have at least one of a compound having a light-emitting function and a compound having a charge transporting function in the polymer.

The specific examples of the compounds represented by formulae (I)-(VII) in the invention are shown below, but the invention is not restricted to these compounds.

1

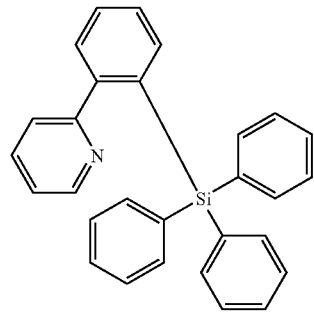

2

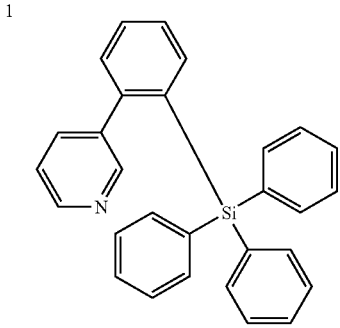

3

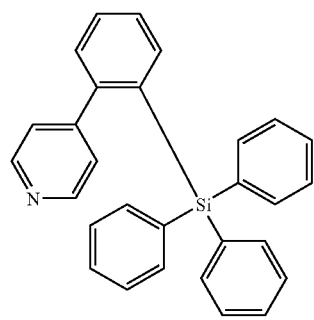

4

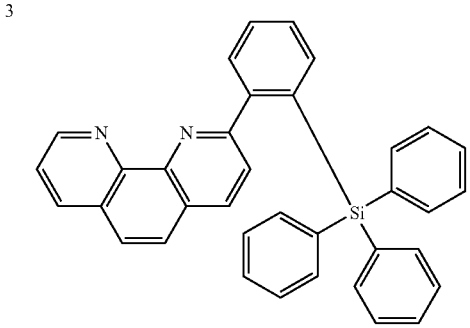

5

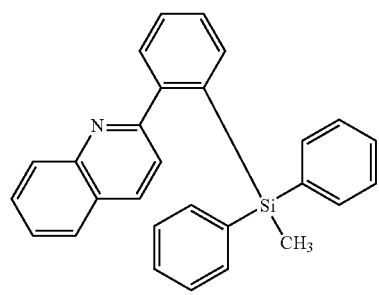

6

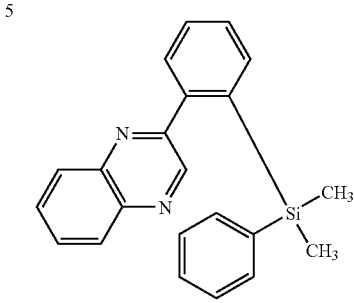

7

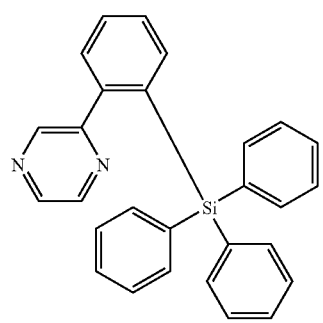

8

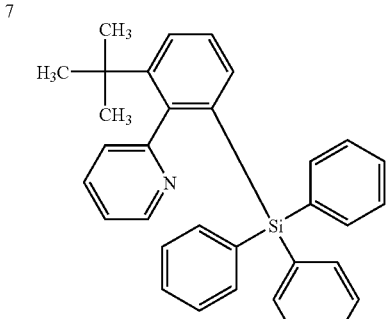

-continued
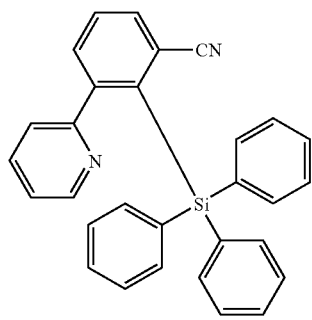
9
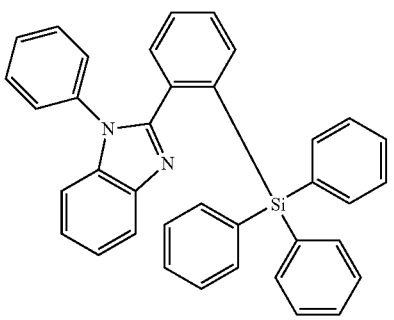
10
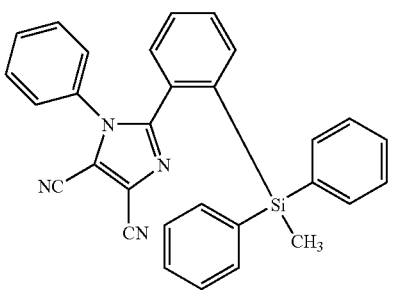
11
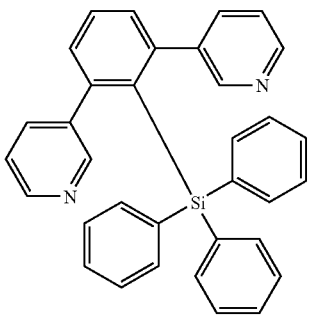
12
13
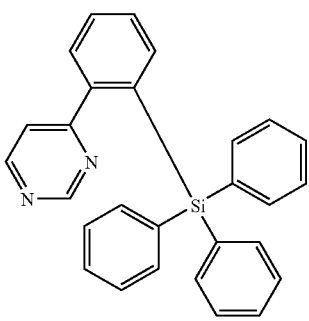
14
15
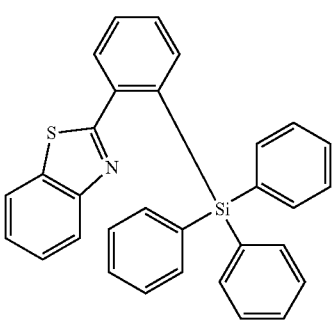
16
17
18

-continued
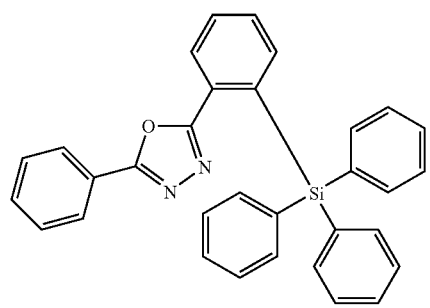
19
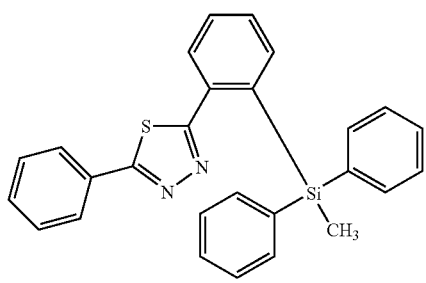
20
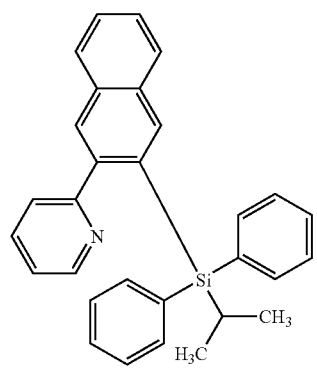
21
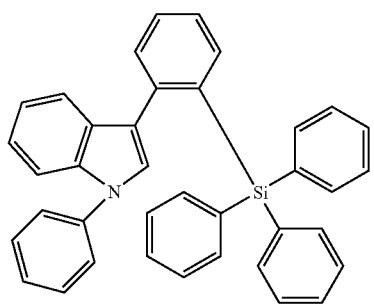
22
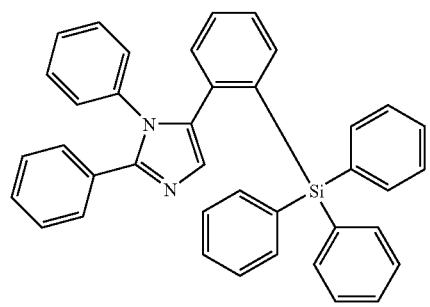
23
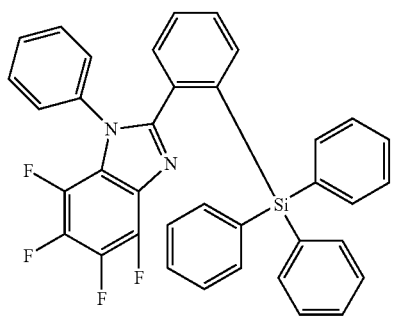
24
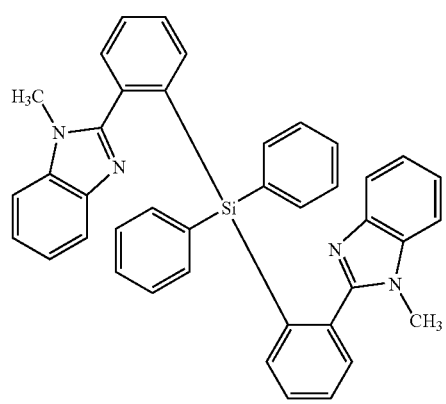
25
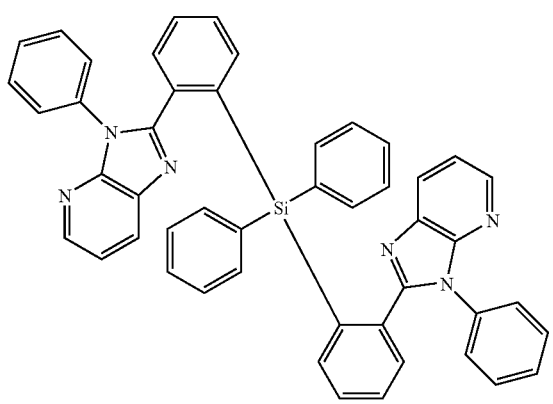
26

-continued
21
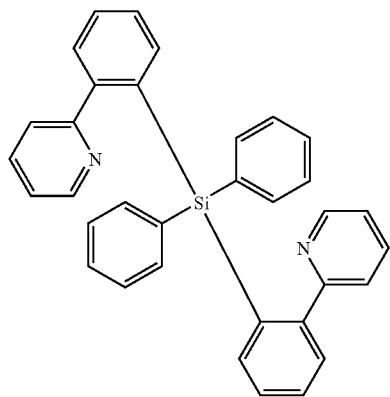
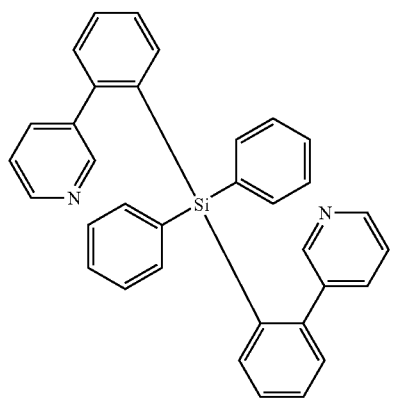
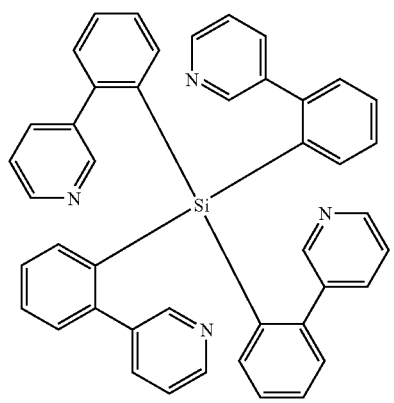
27
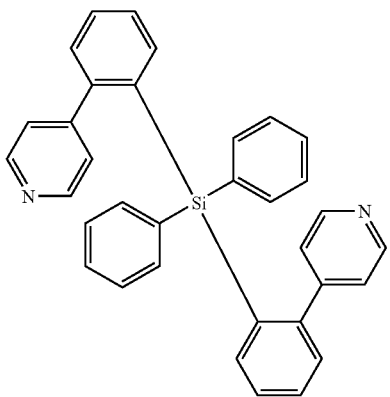
29
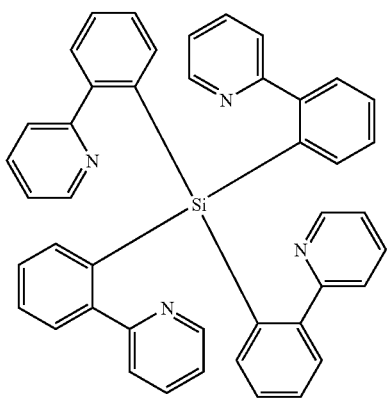
31
28
30
32
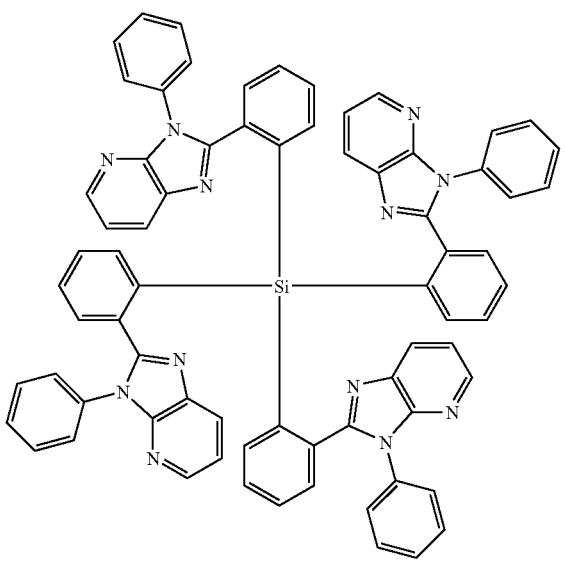

-continued
33
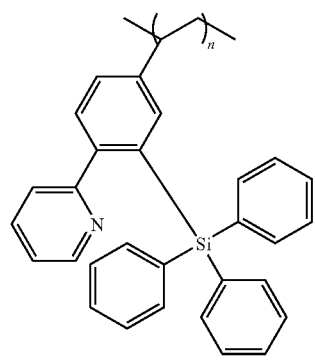
Mass average molecular weight; 7,000.
34
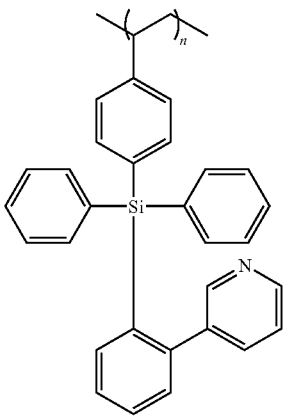
Mass average molecular weight; 15,000.
35
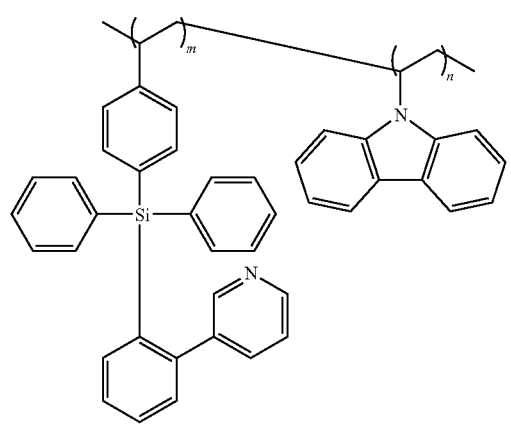
Mass ratio (%) m:n = 70:30
Mass average molecular weight; 16,000.
36
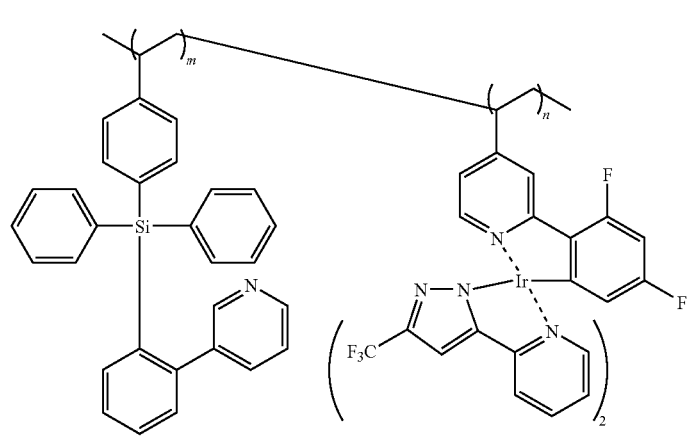
Mass ratio (%) m:n = 85:15
Mass average molecular weight; 10,000.

37
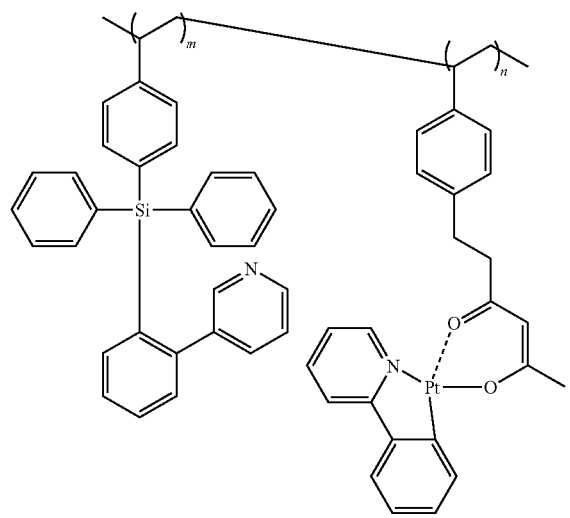
Mass ratio (%) m:n = 85:15
Mass average molecular weight; 15,000.
38
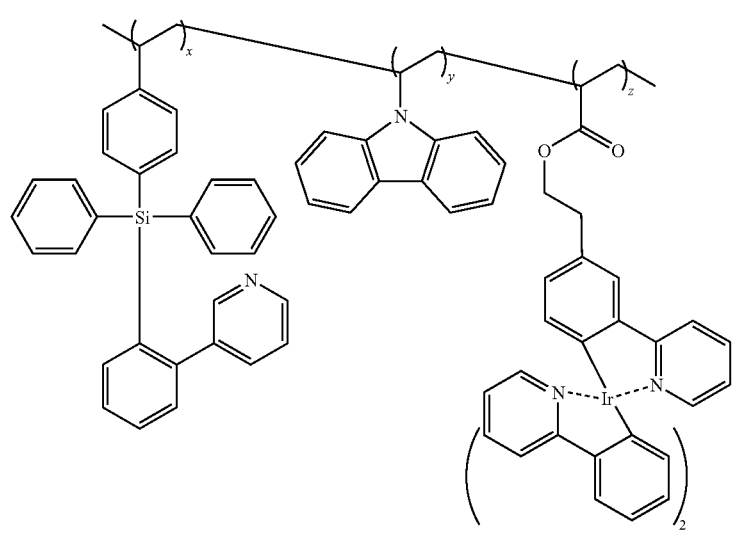
Mass ratio (%) x:y:z = 50:40:10
Mass average molecular weight; 9,000.
39
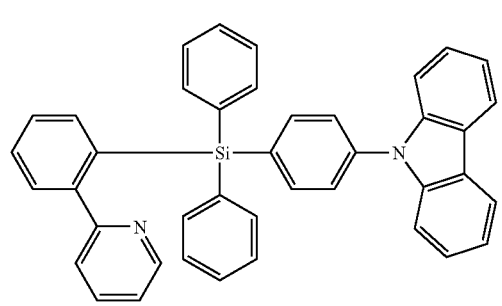
40
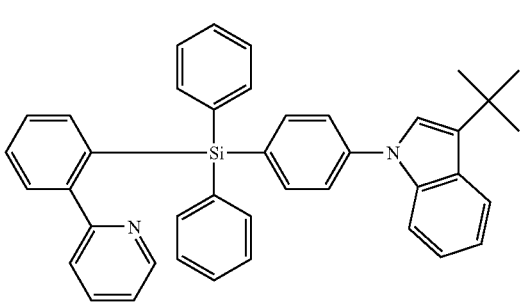

-continued
41
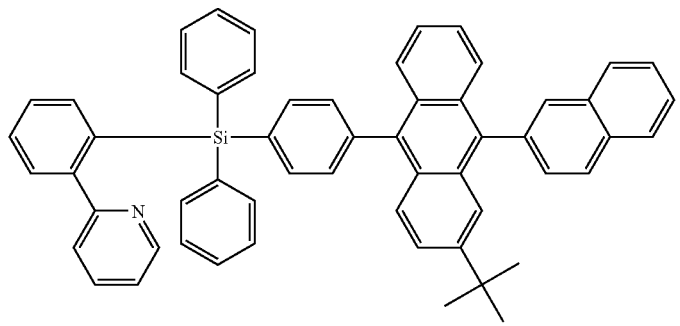
42
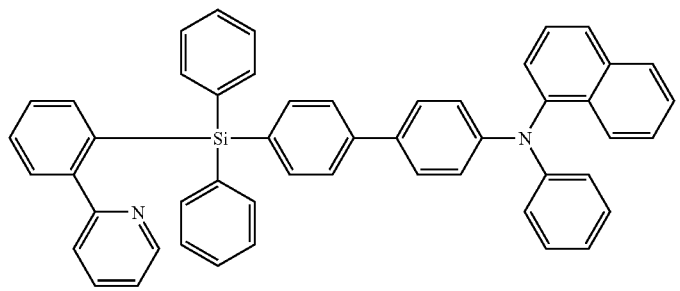
43
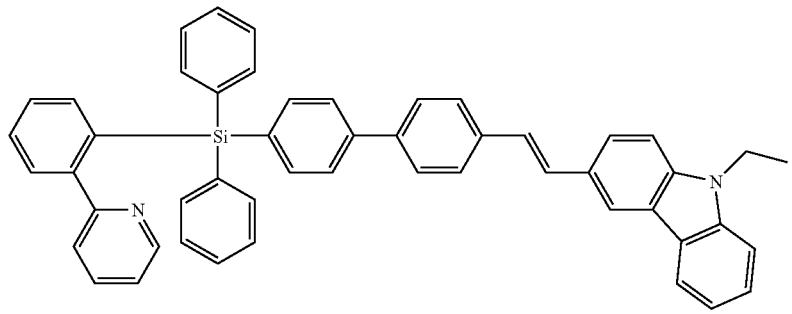
44
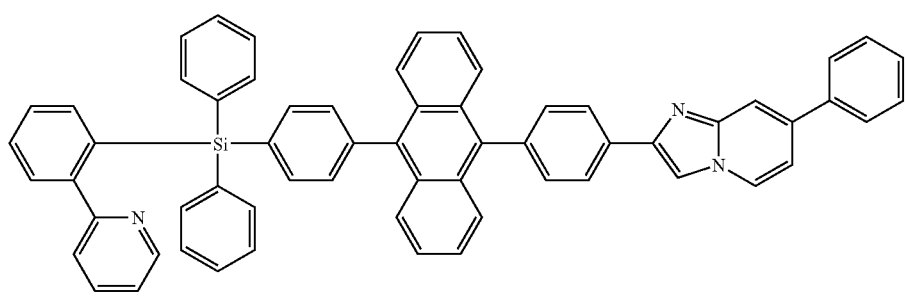
45
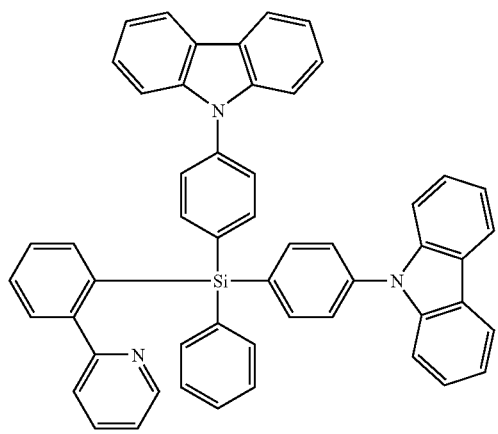
46
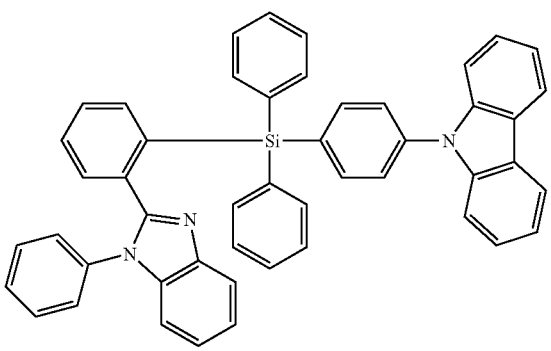

-continued
47
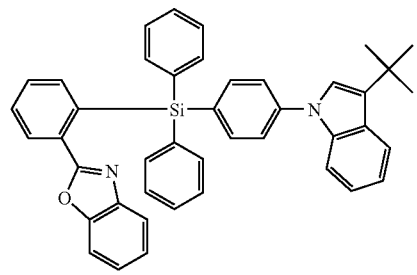
48
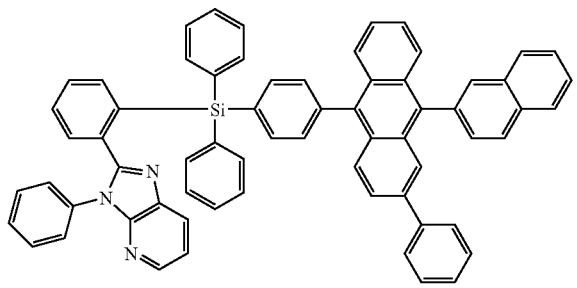
49
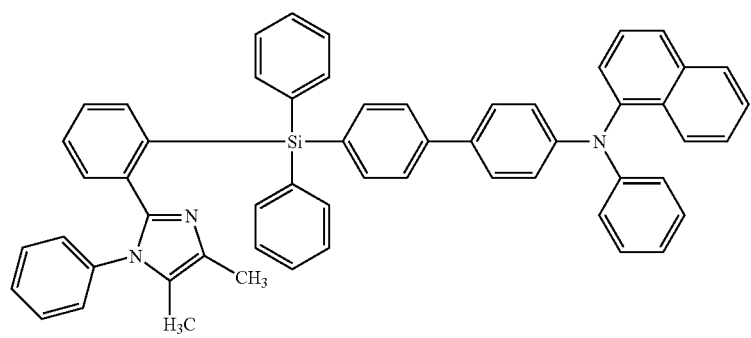
50
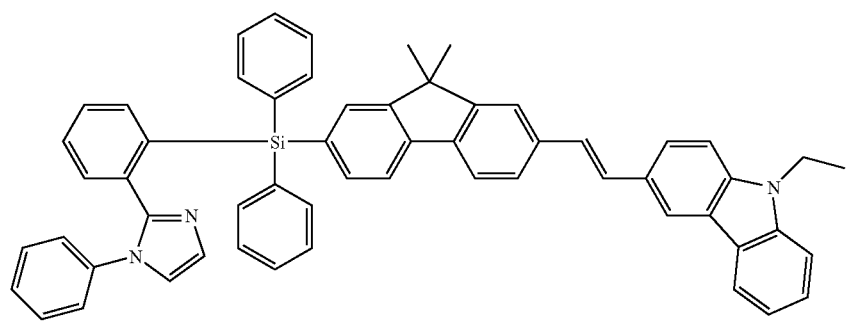
51
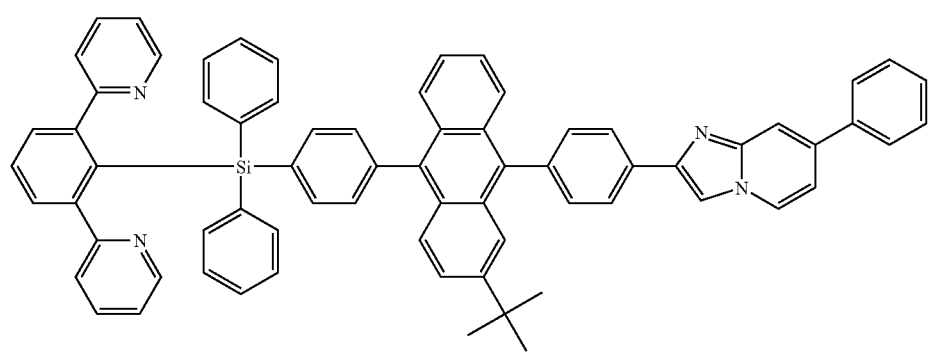

The compounds represented by formulae (I)-(VII) of the invention can be synthesized by the combination of various known synthesizing methods. As the materials of the syntheses, for example, the following materials can be used.

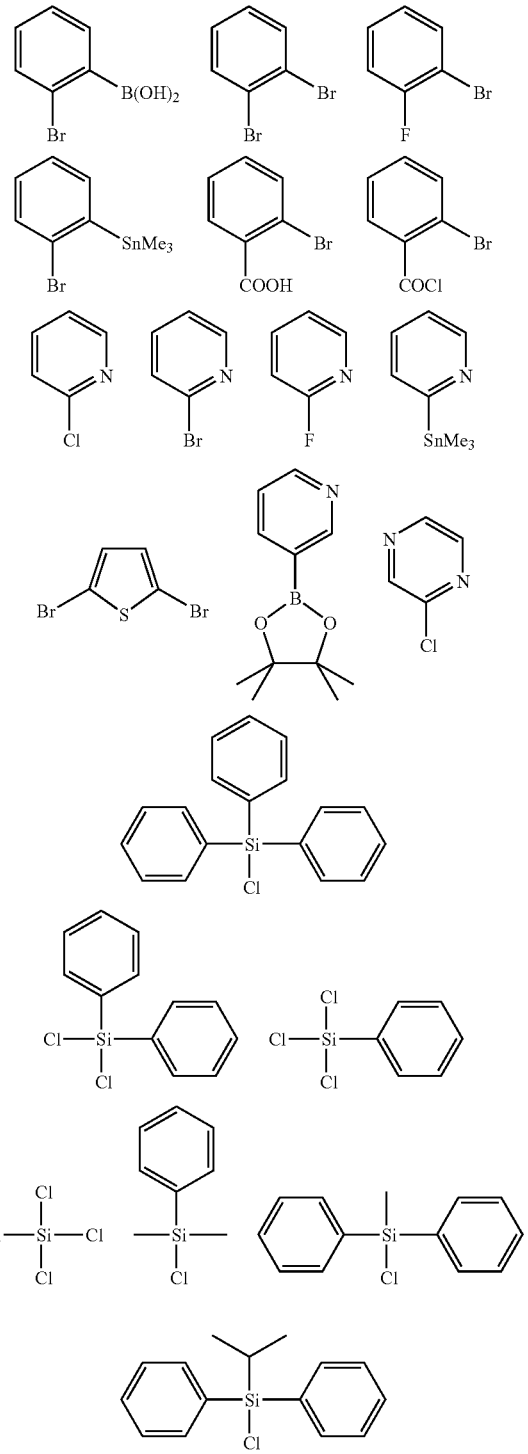

The compound represented by formula (I) can be synthesized, for example, according to Route A via Intermediate A or Route B via Intermediate B and Intermediate C as shown below.

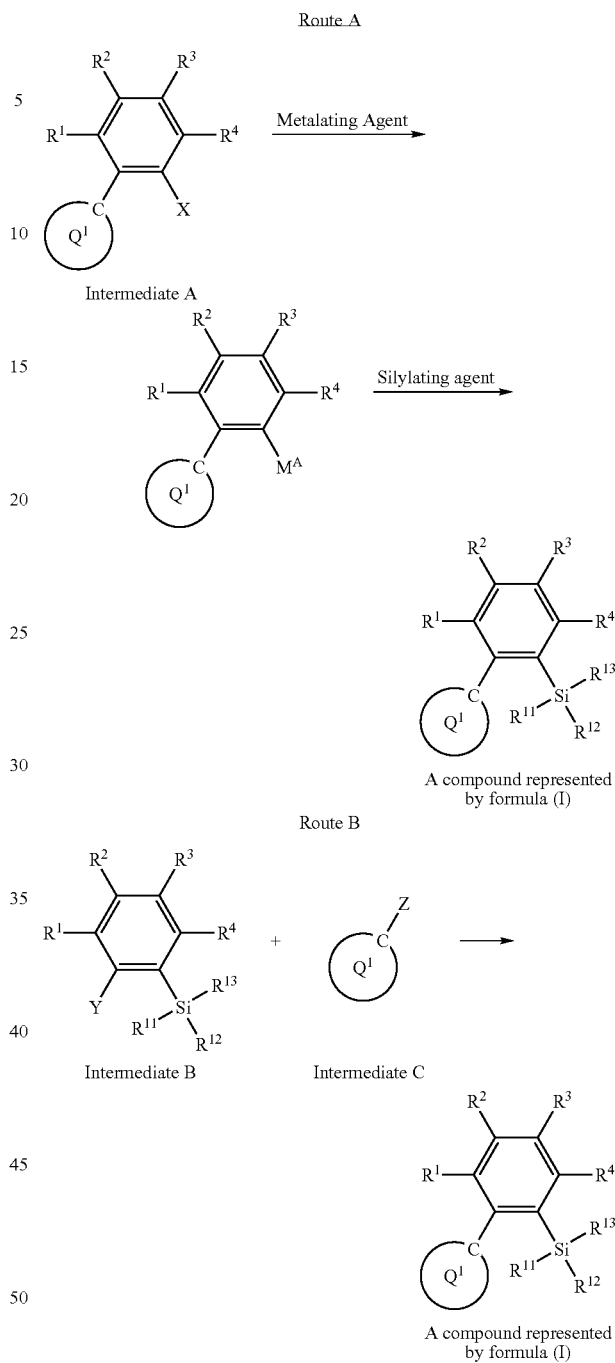

X in Route A represents a Cl group, a Br group, an I group, or an H group, and preferably a Br group. $M^A$ represents Li or Mg, and preferably Li.

The compound represented by formula (I) can be synthesized by, for example, the following reaction. A solution of intermediate A (as the solvent, e.g., diethyl ether, tetrahydrofuran, or dioxane) is metalated by acting a metalating agent (e.g., n-butyl lithium, sec-butyl lithium, tert-butyl lithium, lithium diisopropylamide, dibutyl(tetramethylpiperidino) magnesium lithium, lithium metal, magnesium metal, etc.) at −90° C. to 30° C., and then the metalated intermediate A is reacted with a silylating agent (e.g., triphenylsilyl chloride, methyldiphenylsilyl chloride, dimethylphenylsilyl chloride, diisopropylphenylsilyl chloride, methoxytriphenylsilane, diphenylsilyl dichloride, phenyltrichlorosilane, tetrachlorosilane, etc.), thus the compound represented by formula (I) can be obtained.

Y in Route B represents a Cl group, a Br group, an I group, an —OSO$_2$CF$_3$ group, an —OSO$_2$C$_6$H$_4$CH$_3$ group, or an —OSO$_2$C$_6$H$_4$CF$_3$ group, and Z represents —B(OH)$_2$, —B(OR)$_2$, a (tetramethylpinacolyl)boryl group, an —SnR$_3$ group, a Cl group, a Br group, or an I group.

The compound represented by formula (I) can be synthesized by, for example, the following reaction. Intermediate B (wherein Y is a Cl group, a Br group, an I group, an —OSO$_2$CF$_3$ group, an —OSO$_2$C$_6$H$_4$CH$_3$ group, or an —OSO$_2$C$_6$H$_4$CF$_3$ group) and intermediate C (wherein Z is —B(OH)$_2$, —B(OR)$_2$, or a (tetramethylpinacolyl)boryl group) (from 0.3 to 1.1 equivalent weight to Y) are stirred in a solvent (water, aromatic hydrocarbons such as benzene, toluene, xylene, etc., halogenated hydrocarbons such as dichloroethane, chloroform, etc., ethers such as tetrahydrofuran, 1,2-dimethoxyethane, 1,4-dioxane, diethyl ether, etc., alcohols such as methanol, ethanol, isopropyl alcohol, etc., or esters such as ethyl acetate, butyl acetate, etc.) together with a 0-valent palladium catalyst (such as tetrakis(triphenylphosphine)palladium, bis(dibenzylidene acetone) palladium, etc.) or a divalent palladium catalyst (such as palladium acetate, dichlorobistriphenylphosphine palladium, etc.) (from 0.0001 to 0.5 equivalent weight to Y), a base (sodium tert-butoxy, potassium tert-butoxy, cesium carbonate, sodium carbonate, potassium carbonate, tripotassium phosphate, triethylamine, potassium hydroxide, sodium hydroxide, potassium fluoride, etc.) (from 1.5 to 10 equivalent weight to Y), and if necessary a ligand (phosphine, carbene ligand) at a temperature of from 0° C. to the boiling point of the solvent, thus the compound represented by formula (I) can be obtained.

The specific synthesizing prescriptions are described in the Examples below.

Considering the driving durability of the device, the glass transition temperature (Tg) of the compound of the invention is preferably 130° C. or more and 450° C. or less, more preferably 135° C. or more and 450° C. or less, still more preferably 140° C. or more and 450° C. or less, especially preferably 150° C. or more and 450° C. or less, and most preferably 160° C. or more and 450° C. or less.

Here, Tg can be confirmed by thermal measurement such as differential scanning calorimetry (DSC) and differential thermal analysis (DTA), X-ray diffraction (XRD), and observation with a polarization microscope.

When the device of the invention is a luminescence device utilizing phosphorescence, the lowest excitation triplet energy (T$_1$ energy) of the compound of the invention is preferably 60 kcal/mol (251.4 kJ/mol) or more and 95 kcal/mol (398.05 kJ/mol) or less, more preferably 65 kcal/mol (272.35 kJ/mol) or more and 95 kcal/mol (398.05 kJ/mol) or less, and still more preferably 68 kcal/mol (284.92 kJ/mol) or more and 95 kcal/mol (398.05 kJ/mol) or less.

Here, T$_1$ energy can be found by measuring the spectrum of phosphorescence of the film of a material, and from the short wave end of the spectrum of phosphorescence. For example, a film is formed in a thickness of about 50 nm on a cleaned quartz glass substrate by a vacuum deposition method of a material, and the spectrum of phosphorescence of the film is measured with an F-7000 Hitachi fluorescence spectrophotometer (manufactured by Hitachi High Technologies) under a liquid nitrogen temperature. T$_1$ energy can be found by converting the rising wavelength on the short wavelength side of the obtained emission spectrum into an energy unit.

An organic electroluminescence device containing the compound of the invention will be described below.

Organic Electroluminescence Device:

It is preferred for the organic electroluminescence device to further have at least one organic layer between the light-emitting layer and the cathode, wherein the organic layer between the light-emitting layer and the cathode contains the compound represented by formula (I).

The organic electroluminescence device in the invention comprises a substrate having thereon the cathode and the anode and an organic layer including a light-emitting layer between the electrodes. It is preferred that at least one electrode of the cathode and the anode is transparent from the properties of the luminescence device.

As the form of lamination of the organic layers in the invention, an embodiment of lamination of a hole-transporting layer, a light-emitting layer and an electron-transporting layer from the anode side is preferred. Further, a hole-injecting layer is provided between the hole-transporting layer and the anode, and/or an electron-transporting intermediate layer is provided between the light-emitting layer and the electron-transporting layer. In addition, it is also possible to provide a hole-transporting intermediate layer between the light-emitting layer and the hole-transporting layer and an electron-injecting layer between the cathode and the electron-transporting layer.

Incidentally, each of these layers may consist of a plurality of layers.

Each layer constituting the organic layers can be preferably formed by any of dry film-forming methods such as a vacuum deposition method or a sputtering method, a transfer method, a printing method, a coating method, an ink jet method, and a spraying method.

The elements constituting the luminescence device of the invention will be described in detail below.

Substrate:

The substrate for use in the invention is preferably a substrate that does not scatter or attenuate the light emitted from the organic layers. The specific examples of the materials of the substrate include inorganic materials, e.g., yttria stabilized zirconia (YSZ), glass, etc., and organic materials, such as polyester, e.g., polyethylene terephthalate, polybutylene phthalate, polyethylene naphthalate, etc., polystyrene, polycarbonate, polyether sulfone, polyallylate, polyimide, polycycloolefin, norbornene resin, poly(chlorotrifluoroethylene), etc.

When glass is used as the substrate, non-alkali glass is preferably used as the material for reducing elution of ions from the glass. Further, when soda lime glass is used, it is preferred to provide a barrier coat such as silica. In the case of organic materials, materials excellent in heat resistance, dimensional stability, solvent resistance, electrical insulating properties and processability are preferably used.

The shape, structure and size of the substrate are not especially restricted, and these can be arbitrarily selected in accordance with the intended use and purpose of the luminescent device. In general, the substrate is preferably plate-shaped. The structure of the substrate may be a single layer structure or may be a lamination structure, and may consist of a single member or may be formed of two or more members.

The substrate may be colorless and transparent, or may be colored and transparent, but from the point of not scattering or attenuating the light emitted from the organic light-emitting layer, a colorless and transparent substrate is preferably used.

The substrate can be provided with a moisture permeation-preventing layer (a gas barrier layer) on the front surface or rear surface.

As the materials of the moisture permeation-preventing layer (the gas barrier layer), inorganic materials such as silicon nitride and silicon oxide are preferably used. The moisture permeation-preventing layer (the gas barrier layer) can be formed, for example, by a high frequency sputtering method.

When a thermoplastic substrate is used, if necessary, a hard coat layer and an undercoat layer may further be provided.

Anode:

The anode is generally sufficient to have the function of the electrode to supply holes to an organic layer. The shape, structure and size of the anode are not especially restricted, and these can be arbitrarily selected from known materials of electrode in accordance with the intended use and purpose of the luminescent device. The anode is generally provided as the transparent anode.

As the materials of anode, for example, metals, alloys, metallic oxides, electrically conductive compounds, and mixtures of these materials are preferably exemplified. The specific examples of the materials of anode include electrically conductive metallic oxides, e.g., tin oxides doped with antimony or fluorine (ATO, FTO), tin oxide, zinc oxide, indium oxide, indium tin oxide (ITO), indium zinc oxide (IZO), etc., metals, e.g., gold, silver, chromium, nickel, etc., mixtures or laminates of these metals with electrically conductive metallic oxides, inorganic electrically conductive substances, e.g., copper iodide, copper sulfide, etc., organic electrically conductive materials, e.g., polyaniline, polythiophene, polypyrrole, etc., laminates of these materials with ITO, etc. Of these materials, electrically conductive metallic oxides are preferred, and ITO is especially preferred in view of productivity, high conductivity, transparency and the like.

The anode can be formed on the substrate in accordance with various methods arbitrarily selected from, for example, wet methods, e.g., a printing method, a coating method, etc., physical methods, e.g., a vacuum deposition method, a sputtering method, an ion plating method, etc., and chemical methods, e.g., a CVD method, a plasma CVD method, etc., taking the suitability with the material to be used in the anode into consideration. For example, in the case of selecting ITO as the material of the anode, the anode can be formed according to a direct current or high frequency sputtering method, a vacuum deposition method, an ion plating method, etc.

In the organic electroluminescent device in the invention, the position of the anode to be formed is not especially restricted and can be formed anywhere in accordance with the intended use and purpose of the luminescent device, but preferably provided on the substrate. In this case, the anode may be formed on the entire surface of one side of tie substrate, or may be formed at a part.

As patterning in forming the anode, patterning may be performed by chemical etching such as by photo-lithography, may be carried out by physical etching by laser and the like, may be performed by vacuum deposition or sputtering on a superposed mask, or a lift-off method and a printing method may be used.

The thickness of the anode can be optionally selected in accordance with the materials of the anode, so that it cannot be regulated unconditionally, but the thickness is generally from 10 nm to 50 μm or so, and is preferably from 50 nm to 20 μm.

The value of resistance of the anode is preferably $10^3$ Ω/□ or less, and more preferably $10^2$ Ω/□ or less. In the case where the anode is transparent, it may be colorless and transparent, or may be colored and transparent. For collecting emission from the transparent anode side, the transmittance is preferably 60% or more, and more preferably 70% or more.

In connection with transparent anodes, description is found in Yutaka Sawada supervised, *Tomei Denkyoku-Maku no Shintenkai*(*New Development in Transparent Conductive Films*), CMC Publishing Co., Ltd. (1999), and the description therein can be applied to the invention. In the case of using a plastic substrate low in heat resistance, a transparent anode film formed with ITO or IZO at a low temperature of 150° C. or less is preferred.

Cathode:

The cathode is generally sufficient to have the function of the electrode to inject electrons to organic layers. The shape, structure and size of the cathode are not especially restricted, and these can be arbitrarily selected from known materials of electrode in accordance with the intended use and purpose of the luminescent device.

As the materials to constitute the cathode, for example, metals, alloys, metallic oxides, electrically conductive compounds, and mixtures of these materials are exemplified. The specific examples of the materials of cathode include alkali metals (e.g., Li, Na, K, Cs, etc.), alkaline earth metals (e.g., Mg, Ca, etc.), gold, silver, lead, aluminum, sodium-potassium alloy, lithium-aluminum alloy, magnesium-silver alloy, indium, rare earth metals, e.g., ytterbium, etc. These materials may be used by one kind alone, but from the viewpoint of the compatibility of stability and an electron injecting property, two or more kinds of materials can be preferably used in combination.

As the materials constituting the cathode, alkali metals and alkaline earth metals are preferred of these materials in the point of an electron injecting property, and materials mainly comprising aluminum are preferred for their excellent preservation stability.

The materials mainly comprising aluminum mean aluminum alone, alloys of aluminum with 0.01 to 10 mass % of alkali metal or alkaline earth metal, or mixtures of these (e.g., lithium-aluminum alloy, magnesium-aluminum alloy, etc.).

The materials of the cathode are disclosed in detail in JP-A-2-15595 and JP-A-5-121172, and the materials described in these patents can also be used in the invention.

The cathode can be formed by known methods with no particular restriction. For example, the cathode can be formed according to wet methods, e.g., a printing method, a coating method, etc., physical methods, e.g., a vacuum deposition method, a sputtering method, an ion plating method, etc., and chemical methods, e.g., a CVD method, a plasma CVD method, etc., taking the suitability with the material constituting the cathode into consideration. For example, in the case of selecting metals as the materials of the cathode, the cathode can be formed with one or two or more kinds of the materials at the same time or in order by a sputtering method, etc.

Patterning in forming the cathode may be performed by chemical etching such as a method by photo-lithography, may be carried out by physical etching such as a method by laser, may be performed by vacuum deposition or sputtering on a superposed mask, or a lift-off method and a printing method may be used.

The position of the cathode to be formed is not especially restricted and can be formed anywhere in the invention. The cathode may be formed on the entire surface of the organic layer, or may be formed at a part.

A dielectric layer comprising fluoride or oxide of alkali metal or alkaline earth metal may be inserted between the cathode and the organic layer in a thickness of from 0.1 to 5 nm. The dielectric layer can be regarded as a kind of an electron-injecting layer. The dielectric layer can be formed, for example, according to a vacuum deposition method, a sputtering method, an ion plating method, etc.

The thickness of the cathode can be optionally selected in accordance with the materials of the cathode, so that it cannot be regulated unconditionally, but the thickness is generally from 10 nm to 5 µm or so, and is preferably from 50 nm to 1 µm.

The cathode may be transparent or opaque. The transparent cathode can be formed by forming a film of the material of the cathode in a thickness of from 1 to 10 nm, and further laminating transparent conductive materials such as ITO and IZO.

Organic Layers:

Organic layers in the invention will be described below.

The organic EL device in the invention has at least one organic layer including a light-emitting layer, and as the organic layers other than the light-emitting layer, a hole transporting layer, an electron transporting layer, a charge blocking layer, a hole injecting layer, and an electron injecting layer are exemplified, as described above.

In the organic EL device of the invention, each layer constituting the organic layers can be preferably formed by any of dry film-forming methods such as a vacuum deposition method, a sputtering method, etc., a wet coating method, a transfer method, a printing method, an ink jet method, etc.

Light-Emitting Layer:

The light-emitting layer is a layer having functions to receive, at the time of electric field application, holes from the anode, hole injecting layer or hole transporting layer, and to receive electrons from the cathode, electron injecting layer or electron transporting layer, and offer the field of recombination of holes and electrons to emit light.

The light-emitting layer in the invention may consist of light-emitting materials alone, or may comprise a mixed layer of a host material and a light-emitting material. As the host material, the compound represented by formula (I) of the invention is preferred, but compounds other than the compound according to the invention may be used in combination or alone. The details will be described in the item of "Host Materials" later.

The light-emitting material may be a single layer, or may comprise two or more layers, and each layer may emit light in different luminescent color. Further, a material not having a charge-transporting property and not emitting light may be contained in the light-emitting layer.

Light-Emitting Materials:

As the light-emitting materials, both of phosphorescent materials and fluorescent materials can be used in the invention.

The light-emitting layer in the invention can contain two or more light-emitting materials for the purpose of improving color purity and widening light emission wavelength region. It is preferred that the at least one light-emitting materials contains a phosphorescent material.

In view of driving durability, it is preferred that the relationship of at least one of 1.2 eV>ΔIp>0.2 eV and 1.2 eV>ΔEa>0.2 eV is satisfied between the light-emitting material in the invention and the host material. Here, ΔIp means the difference in the Ip values of the host material and the light-emitting material, and ΔEa means the difference in the Ea values of the host material and the light-emitting material.

It is preferred that the at least one light-emitting materials comprises a platinum complex or an iridium complex.

Fluorescent Materials:

The examples of the fluorescent materials generally include various metal complexes represented by metal complexes of benzoxazole, benzimidazole, benzothiazole, styrylbenzene, polyphenyl, diphenylbutadiene, tetraphenylbutadiene, naphthalimide, coumarin, pyran, perinone, oxadiazole, aldazine, pyraridine, cyclopentadiene, bisstyrylanthracene, quinacridone, pyrrolopyridine, thiadiazolopyridine, cyclopentadiene, styrylamine, aromatic dimethylidyne compounds, condensed polycyclic aromatic compounds (anthracene, phenanthroline, pyrene, perylene, rubrene, pentacene, etc.), and 8-quinolinol, pyrromethene complexes, and rare earth complexes, polymer compounds, e.g., polythiophene, polyphenylene, polyphenylenevinylene, etc., organic silanes, and the derivatives thereof.

Phosphorescent Materials:

As the phosphorescent materials, complexes containing a transition metal atom or a lanthanoid atom can be generally exemplified.

For example, the transition metal atom is not especially restricted, but preferably ruthenium, rhodium, palladium, tungsten, rhenium, osmium, iridium, gold, silver, copper and platinum are exemplified, more preferably rhenium, iridium and platinum, and still more preferably iridium and platinum are exemplified.

As the lanthanoid atoms, e.g., lanthanum, cerium, praseodymium, neodymium, samarium, europium, gadolinium, terbium, dysprosium, holmium, erbium, thulium, ytterbium and lutetium are exemplified, and cerium, neodymium, europium and gadolinium are preferred of these lanthanoid atoms.

As the examples of ligands of complexes, the ligands described, for example, in G. Wilkinson et al., *Comprehensive Coordination Chemistry*, Pergamon Press (1987), H. Yersin, *Photochemistry and Photophysics of Coordination Compounds*, Springer-Verlag (1987), and Akio Yamamoto, *Yuki Kinzoku Kagaku-Kiso to Oyo*-(*Organic Metal Chemistry—Elements and Applications*) Shokabo Publishing Co. (1982) are exemplified.

As the specific examples of ligands, halogen ligands (preferably a chlorine ligand), aromatic carbocyclic ligands (preferably having from 5 to 30 carbon atoms, more preferably from 6 to 30 carbon atoms, still more preferably from 6 to 20 carbon atoms, and especially preferably from 6 to 12 carbon atoms, e.g., a cyclopentadienyl anion, a benzene anion, a naphthyl anion, etc.), nitrogen-containing heterocyclic ligands (preferably having from 5 to 30 carbon atoms, more preferably from 6 to 30 carbon atoms, still more preferably from 6 to 20 carbon atoms, and especially preferably from 6 to 12 carbon atoms, e.g., pyrazolylpyridine, pyrrolylpyridine, imidazolylpyridine, triazolylpyridine, phenylisoquinoline, picolinic acid, phenylpyridine, benzoquinoline, quinolinol, bipyridyl, phenanthroline, etc.), diketone ligands (e.g., acetylacetone, etc.), carboxylic acid ligands (preferably having from 2 to 30 carbon atoms, more preferably from 2 to 20 carbon atoms, and still more preferably from 2 to 16 carbon atoms, e.g., an acetic acid ligand, etc.), alcoholate ligands (preferably having from 1 to 30 carbon atoms, more preferably from 1 to 20 carbon atoms, and still more preferably from 6 to 20 carbon atoms, e.g., a phenolate ligand, etc.), silyloxy ligands (preferably having from 3 to 40 carbon atoms, more preferably from 3 to 30 carbon atoms, and still more preferably from 3 to 20 carbon atoms, e.g., a trimethylsilyloxy ligand, a dimethyl-tert-butylsilyloxy ligand, a triphenylsilyloxy ligand, etc.), carbon monoxide ligands, isonitrile ligands, cyano ligands, phosphorus ligands (preferably having from 3 to 40 carbon atoms, more preferably from 3 to 30 carbon atoms, still more preferably from 3 to 20 carbon atoms, and especially preferably from 6 to 20 carbon atoms, e.g., a triphenylphosphine ligand, etc.), thiolate ligands (preferably having from 1 to 30 carbon atoms, more preferably from 1 to 20 carbon atoms, and still more preferably from 6 to 20 carbon atoms, e.g., a phenylthiolate ligand, etc.), phosphine oxide ligands (preferably having from 3 to 30 carbon atoms, more preferably from 8 to 30 carbon atoms, and still more preferably from 18 to 30 carbon atoms, e.g., a triphenylphosphine oxide ligand, etc.) are preferably exemplified, and more preferably nitrogen-containing heterocyclic ligands are exemplified.

These complexes may have one transition metal atom in a compound, or they may be what are called polynuclear complexes having two or more transition metal atoms. They may contain dissimilar metal atoms at the same time.

The specific examples of the phosphorescent materials include phosphorescent compounds disclosed, for example, in U.S. Pat. Nos. 6,303,238B1, 6,097,147, 6,653,654, WO 00/57,676, WO 00/70,655, WO 01/08,230, WO 01/39,234A2, WO 01/41,512A1, WO 02/02,714A2, WO 02/15,645A1, WO 02/44,189A1, WO 04/108,857, WO 04/081,017, WO 04/085,450, WO 05/113,704, WO 05/019,373A2, WO 05/042,444, WO 05/042,550, WO 06/098,505, WO 06/121,811, WO 06/014,599, WO 07/095,118, JP-A2001-247859, JP-A-2002-302671, JP-A-2002-117978, JP-A-2003-133074, JP-A-2002-235076, JP-A-2003-123982, JP-A-2002-170684, EP 1,211,257, JP-A-2002-226495, JP-A-2002-234894, JP-A-2001-247859, JP-A-2001-298470, JP-A-2002-173674, JP-A-2002-203678, JP-A-2002-203679, JP-A-2004-357791, JP-A-2005-310733, JP-A-2005-317516, JP-A-2006-261623, JP-A-2006-232784, JP-A-2006-256999, JP-A-2007-19462, JP-A-2007-84635, and JP-A-2007-96259. Further, as other complex phosphorescent materials, compounds described in *Coordination Chemistry Reviews*, 250, pp. 2093-2126 (2006) are exemplified.

As phosphorescent materials, iridium complexes, platinum complexes and rhenium complexes having at least one coordination manner of a metal-carbon bond, a metal-nitrogen bond, a metal-oxygen bond, and a metal-sulfur bond are preferred. Further, from the viewpoints of luminous efficiency, driving durability and chromaticity, an iridium complex, a platinum complex and a rhenium complex containing a tridentate or higher multidentate ligand are especially preferred. A platinum complex having a tridentate or tetradentate ligand is most preferred.

As the platinum complex, a platinum complex represented by the following formula (C-1) is preferred.

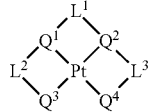
(C-1)

In formula (C-1), each of $Q^1$, $Q^2$, $Q^3$ and $Q^4$ independently represents a ligand to coordinate to Pt; and each of $L^1$, $L^2$ and $L^3$ independently represents a single bond or a divalent liking group.

The platinum complex represented by formula (C-1) will be explained below. Each of $Q^1$, $Q^2$, $Q^3$ and $Q^4$ independently represents a ligand to coordinate to Pt. At this time, bonding of $Q^1$, $Q^2$, $Q^3$ and $Q^4$ to Pt may be any of a covalent bond, an ionic bond, and a coordinate bond. The atoms in $Q^1$, $Q^2$, $Q^3$ and $Q^4$ to bond to Pt are preferably a carbon atom, a nitrogen atom, an oxygen atom, a sulfur atom and a phosphorus atom, and it is preferred that at least one of the atoms in $Q^1$, $Q^2$, $Q^3$ and $Q^4$ to bond to Pt is a carbon atom, and it is more preferred that two of these atoms are carbon atoms.

$Q^1$, $Q^2$, $Q^3$ and $Q^4$ to bond to Pt via a carbon atom may be an anionic ligand or a neutral ligand. As the anionic ligands, a vinyl ligand, an aromatic hydrocarbon ring ligand (e.g., a benzene ligand, a naphthalene ligand, an anthracene ligand, a phenanthrene ligand, etc.), a heterocyclic ligand (e.g., a furan ligand, a thiophene ligand, a pyridine ligand, a pyrazine ligand, a pyrimidine ligand, a pyridazine ligand, a triazine ligand, a thiazole ligand, an oxazole ligand, a pyrrole ligand, an imidazole ligand, a pyrazole ligand, a triazole ligand, and condensed ring products containing these ligands (e.g, a quinoline ligand, a benzothiazole ligand, etc.)) are exemplified. As the neutral ligand, a carbene ligand is exemplified.

$Q^1$, $Q^2$, $Q^3$ and $Q^4$ to bond to Pt via a nitrogen atom may be a neutral ligand or an anionic ligand. As the neutral ligands, a nitrogen-containing aromatic heterocyclic ligand (a pyridine ligand, a pyrazine ligand, a pyrimidine ligand, a pyridazine ligand, a triazine ligand, an imidazole ligand, a pyrazole ligand, a triazole ligand, an oxazole ligand, a thiazole ligand, and condensed ring products containing these ligands (e.g., a quinoline ligand, a benzimidazole ligand, etc.)), an amine ligand, a nitrile ligand, and an imine ligand are exemplified. As the anionic ligands, an amino ligand, an imino ligand, a nitrogen-containing aromatic heterocyclic ligand (e.g., a pyrrole ligand, an imidazole ligand, a triazole ligand, and condensed ring products containing these ligands (e.g., an indole ligand, a benzimidazole ligand, etc,)) are exemplified.

$Q^1$, $Q^2$, $Q^3$ and $Q^4$ to bond to Pt via an oxygen atom may be a neutral ligand or an anionic ligand. As the neutral ligands, an ether ligand, a ketone ligand, an ester ligand, an amido ligand, an oxygen-containing heterocyclic ligand (e.g., a furan ligand, an oxazole ligand, and condensed ring products containing these ligands (e.g., a benzoxazole ligand, etc.)) are exemplified. As the anionic ligands, an alkoxy ligand, an aryloxy ligand, a hetero-aryloxy ligand, an acyloxy ligand, a silyloxy ligand, etc., are exemplified.

$Q^1$, $Q^2$, $Q^3$ and $Q^4$ to bond to Pt via a sulfur atom may be a neutral ligand or an anionic ligand. As the neutral ligands, a thioether ligand, a thioketone ligand, a thioester ligand, a thioamide ligand, a sulfur-containing heterocyclic ligand (e.g., a thiophene ligand, a thiazole ligand, and condensed ring products containing these ligands (e.g., a benzothiazole ligand, etc.)) are exemplified. As the anionic ligands, an alkylmercapto ligand, an arylmercapto ligand, a hetero-arylmercapto ligand, etc., are exemplified.

$Q^1$, $Q^2$, $Q^3$ and $Q^4$ to bond to Pt via a phosphorus atom may be a neutral ligand or an anionic ligand. As the neutral ligands, a phosphine ligand, a phosphoric ester ligand, a phosphorous ester ligand, a phosphorus-containing ligand (e.g., a phosphinine ligand, etc.) are exemplified. As the anionic ligands, a phosphino ligand, a phosphinyl ligand, a phosphoryl ligand are exemplified.

Each of the groups represented by $Q^1$, $Q^2$, $Q^3$ and $Q^4$ may have a substituent, and as the substituents, those exemplified above as substituent group A can be arbitrarily applied. In addition, substituents may be linked to each other (when $Q^3$ and $Q^4$ are linked, the Pt complex is a Pt complex of a cyclic tetradentate ligand).

The groups represented by $Q^1$, $Q^2$, $Q^3$ and $Q^4$ are preferably an aromatic hydrocarbon ring ligand to bond to Pt via a carbon atom, an aromatic heterocyclic ligand to bond to Pt via a carbon atom, a nitrogen-containing aromatic heterocyclic ligand to bond to Pt via a nitrogen atom, an acyloxy ligand, an alkyloxy ligand, an aryloxy ligand, a hetero-aryloxy ligand, and a silyloxy ligand, more preferably an aromatic hydrocarbon ring ligand to bond to Pt via a carbon atom, an aromatic heterocyclic ligand to bond to Pt via a carbon atom, a nitrogen-containing aromatic heterocyclic ligand to bond to Pt via a nitrogen atom, an acyloxy ligand, and an aryloxy ligand, and still more preferably an aromatic hydrocarbon ring ligand to bond to Pt via a carbon atom, an aromatic heterocyclic ligand to bond to Pt via a carbon atom, a nitrogen-containing aromatic heterocyclic ligand to bond to Pt via a nitrogen atom, and an acyloxy ligand.

Each of $L^1$, $L^2$ and $L^3$ represents a single bond or a divalent linking group. As the divalent lining groups represented by $L^1$, $L^2$ and $L^3$, an alkylene group (e.g., methylene, ethylene, propylene, etc.), an arylene group (e.g., phenylene, naphthalenediyl), a hetero-arylene group (e.g., pyridinediyl, thiophenediyl, etc.), an imino group (—NR—) (e.g., a phenylimino group, etc.), an oxy group (—O—), a thio group (—S—), a phosphinidene group (—PR—) (e.g., a phenylphosphinidene group, etc.), a silylene group (—SiRR'—) (e.g., a dimethylsilylene group, a diphenylsilylene group, etc.), and groups obtained by combining these groups are exemplified. These linking groups may further have a substituent.

Each of $L^1$, $L^2$ and $L^3$ preferably represents a single bond, an alkylene group, an arylene group, a hetero-arylene group, an imino group, an oxy group, a thio group, or a silylene group, more preferably a single bond, an alkylene group, an arylene group, or an imino group, still more preferably a single bond, an alkylene group, or an arylene group, still further preferably a single bond, a methylene group, or a phenylene group, still yet more preferably a single bond, a di-substituted methylene group, still yet further preferably a single bond, a dimethylmethylene group, a diethylmethylene group, a diisobutylmethylene group, a dibenzylmethylene group, an ethylmethylene group, a methylpropylmethylene group, an isobutylmethylmethylene group, a diphenylmethylene group, a methylphenylmethylene group, a cyclohexanediyl group, a cyclopentanediyl group, a fluorenediyl group, or a fluoromethylmethylene gropu, and especially preferably represents a single bond, a dimethylmethylene group, a diphenylmethylene group, or a cyclohexanediyl group.

The platinum complex represented by formula (C-1) is more preferably represented by the following formula (C-2).

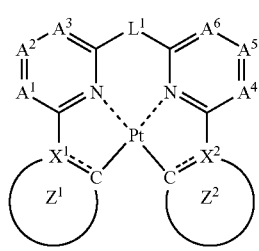

(C-2)

In formula (C-2), $L^1$ represents a single bond or a divalent linking group; each of $A^1$, $A^2$, $A^3$, $A^4$, $A^5$ and $A^6$ independently represents C—R or N; R represents a hydrogen atom or a substituent; each of $X^1$ and $X^2$ represents C or N; and each of $Z^1$ and $Z^2$ represents a 5- or 6-membered aromatic ring or an aromatic heterocyclic ring formed together with X—C in the formula.

Formula (C-2) will be described below. $L^1$ has the same definition as in formula (C-1) and the preferred range is also the same. Each of $A^1$, $A^2$, $A^3$, $A^4$, $A^5$ and $A^6$ independently represents C—R or N, R represents a hydrogen atom or a substituent. As the substituents represented by R, those exemplified above as substituent group A can be applied.

Each of $A^1$, $A^2$, $A^3$, $A^4$, $A^5$ and $A^6$ preferably represents C—R, and R may be linked to each other to form a ring. When each of $A^1$, $A^2$, $A^3$, $A^4$, $A^5$ and $A^6$ represents C—R, R represented by $A^2$ and $A^5$ is preferably a hydrogen atom, an alkyl group, an aryl group, an amino group, an alkoxy group, an aryloxy group, a fluorine group, or a cyano group, more preferably a hydrogen atom, an amino group, an alkoxy group, an aryloxy group, or a fluorine group, and especially preferably a hydrogen atom or a fluorine group. R represented by $A^1$, $A^3$, $A^4$ and $A^6$ is preferably a hydrogen atom, an alkyl group, an aryl group, an amino group, an alkoxy group, an aryloxy group, a fluorine group, or a cyano group, more preferably a hydrogen atom, an amino group, an alkoxy group, an aryloxy group, or a fluorine group, and especially preferably a hydrogen atom. Each of $X^1$ and $X^2$ represents C or N. $Z^1$ represents a 5- or 6-membered aromatic hydrocarbon ring or an aromatic heterocyclic ring formed together with $X^1$—C in the formula. $Z^2$ represents a 5- or 6-membered aromatic hydrocarbon ring or an aromatic heterocyclic ring formed together with $X^2$—C in the formula. As the aromatic hydrocarbon rings or the aromatic heterocyclic rings represented by $Z^1$ and $Z^2$, a benzene ring, a naphthalene ring, an anthracene ring, a pyrene ring, a phenanthrene ring, a perylene ring, a pyridine ring, a quinoline ring, an isoquinoline ring, a phenanthridine ring, a pyrimidine ring, a pyrazine ring, a pyridazine ring, a triazine ring, a cinnoline ring, an acridine ring, a phthalazine ring, a quinazoline ring, a quinoxaline ring, a naphthyridine ring, a pteridine ring, a pyrrole ring, a pyrazole ring, a triazole ring, an indole ring, a carbazole ring, an indazole ring, a benzimidazole ring, an oxazole ring, a thiazole ring, an oxadiazole ring, a thiadiazole ring, a benzoxazole ring, a benzothiazole ring, an imidazopyridine ring, a thiophene ring, a benzothiophene ring, a furan ring, a benzofuran ring, a phosphor ring, a phosphinine ring, and a silol ring are exemplified. $Z^1$ and $Z^2$ may have a substituent, and as the substituents, those exemplified above as substituent group A can be applied. Further, $Z^1$ and $Z^2$ may form a condensed ring with other rings.

Each of $Z^1$ and $Z^2$ preferably represents a benzene ring, a naphthalene ring, a pyrazole ring, an imidazole ring, a triazole ring, a pyridine ring, an indole ring or a thiophene ring, and more preferably a benzene ring, a pyrazole ring or a pyridine ring.

The platinum complex represented by formula (C-2) is more preferably represented by the following formula (C-3).

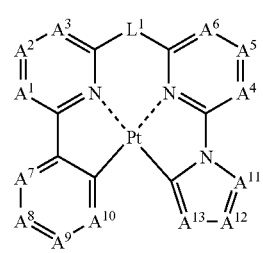

(C-3)

In formula (C-3), each of $A^1$ to $A^{13}$ independently represents C—R or N. R represents a hydrogen atom or a substituent. $L^1$ represents a single bond or a divalent linking group.

As the specific examples of the light-emitting materials, for example, the following are exemplified, but the invention is not restricted thereto.

D-1 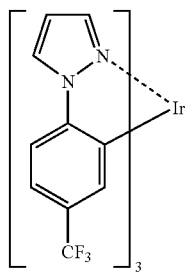
D-2 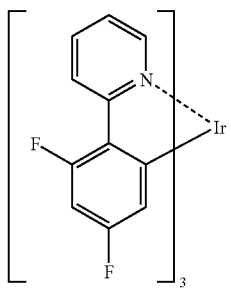
D-3 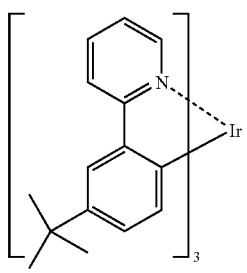
D-4 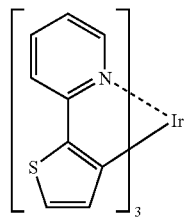
D-5 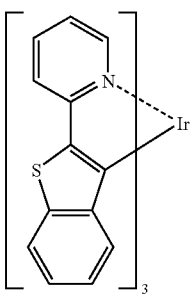
D-6 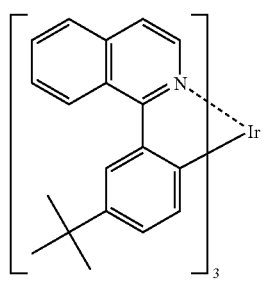
D-7 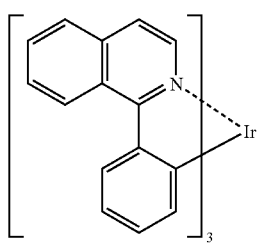
D-8 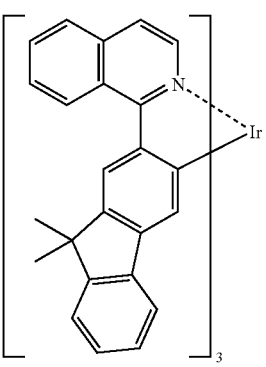
D-9 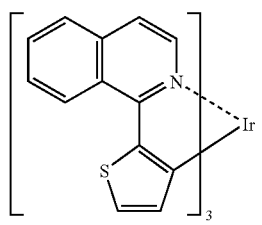
D-10 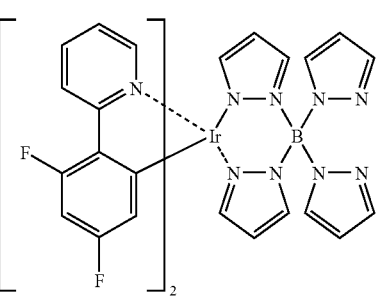
D-11 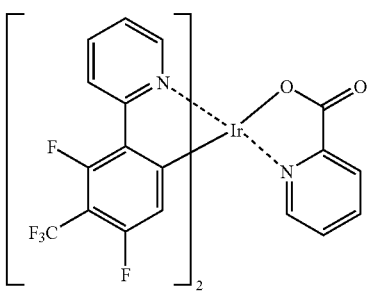

D-12 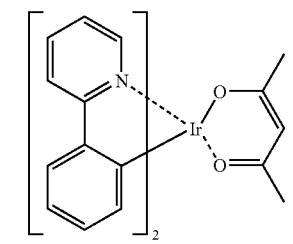
D-13 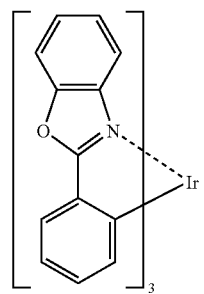
D-14 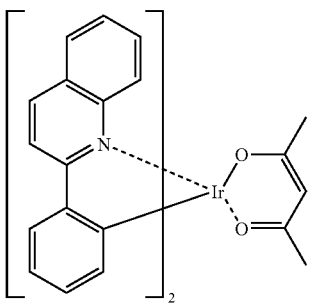
D-15 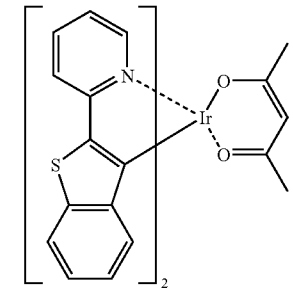
D-16 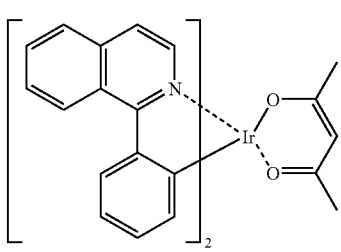
D-17 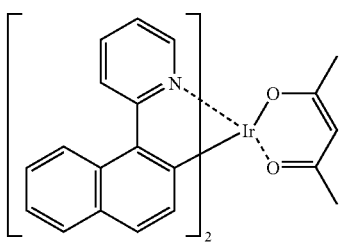
D-18 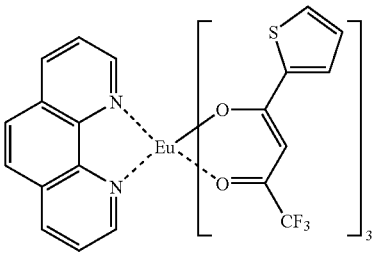
D-19 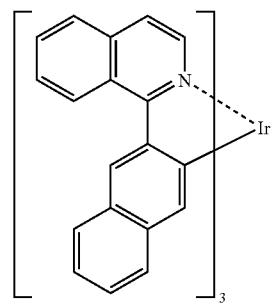
D-20 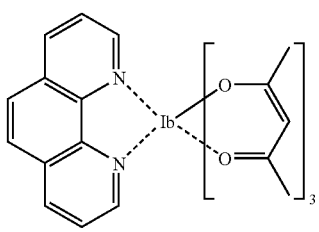
D-21 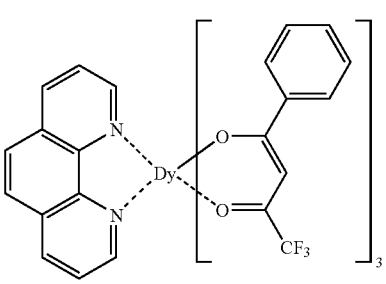
D-22 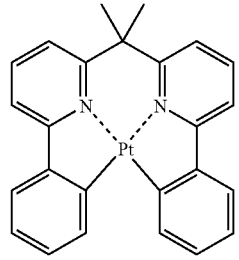
D-23 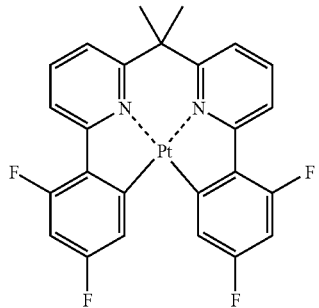

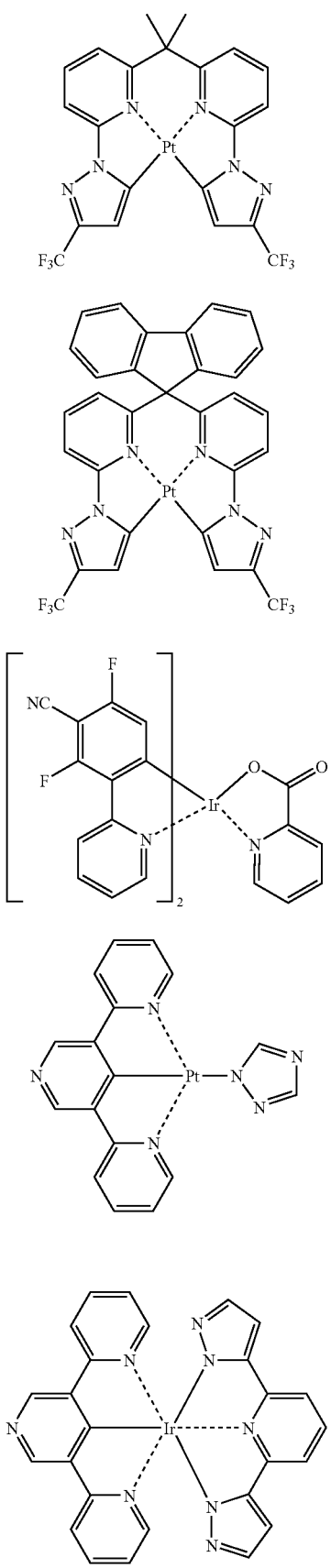
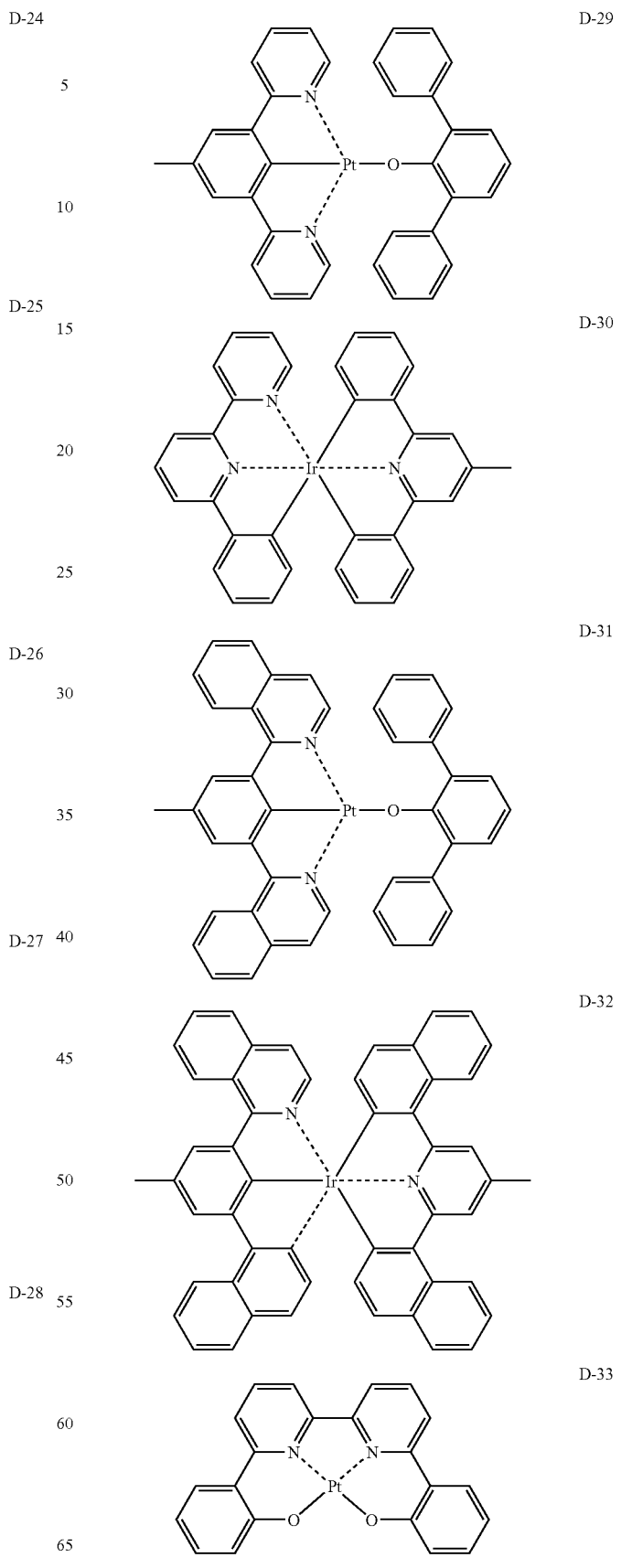

-continued
D-34
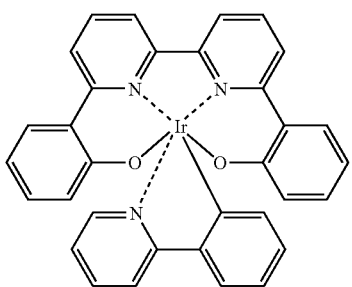
D-35
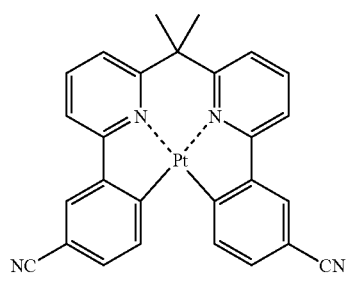
D-36
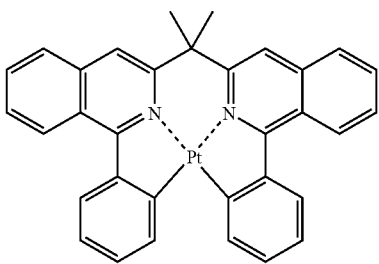
D-37
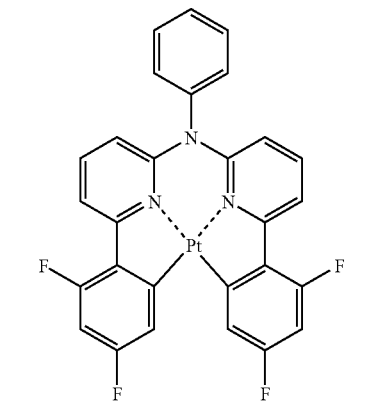
D-38
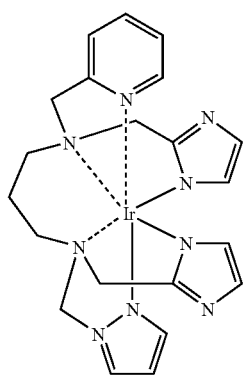
-continued
D-39
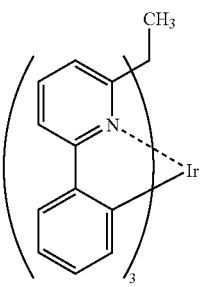
D-40
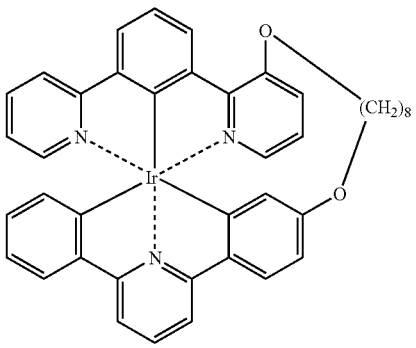
D-41
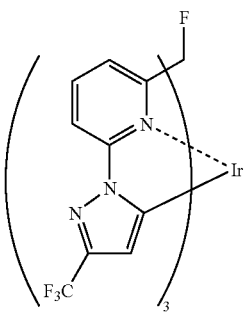
D-42
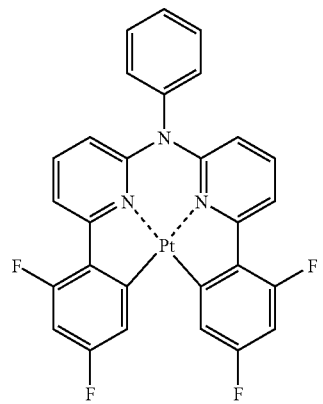

D-43
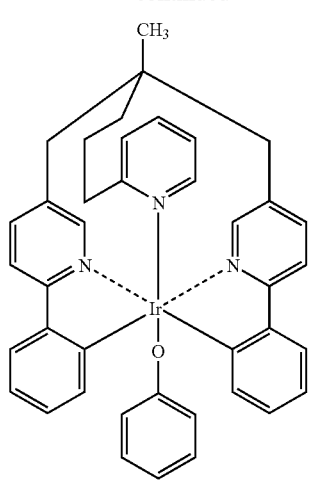
D-44
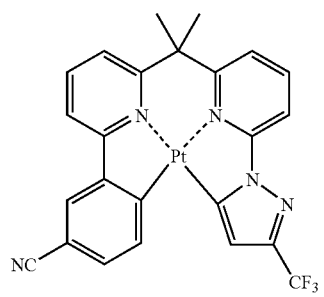
D-45
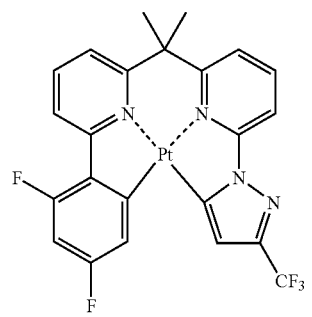
D-46
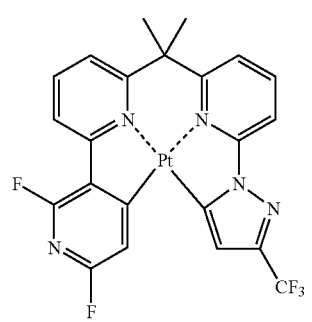
D-47
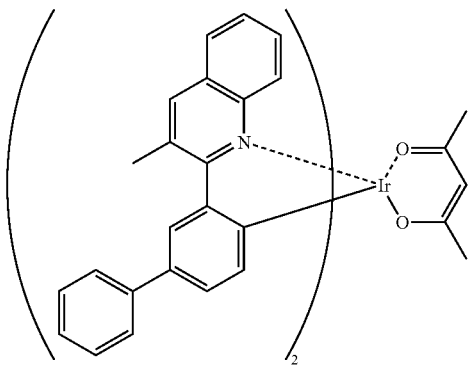
D-48
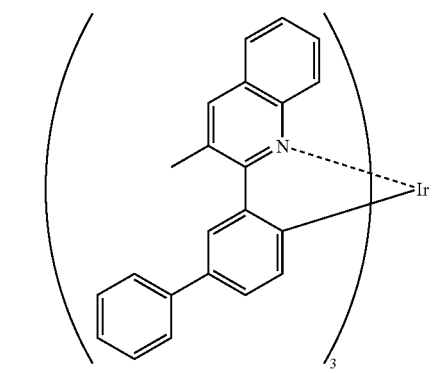
D-49
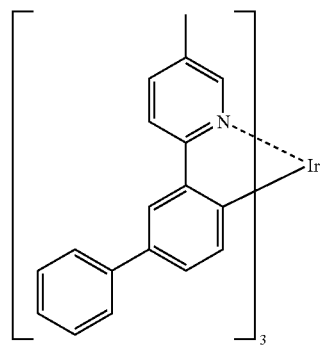
D-50
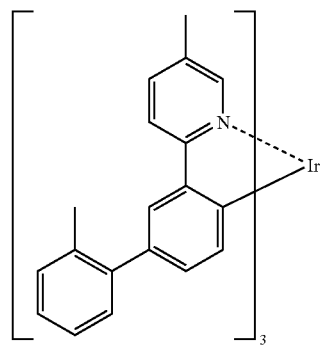

-continued
D-51
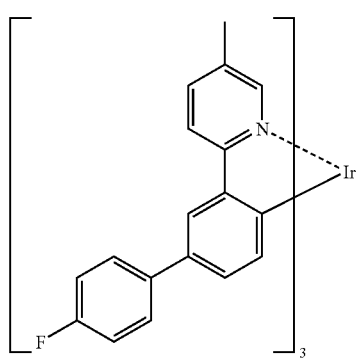
D-52
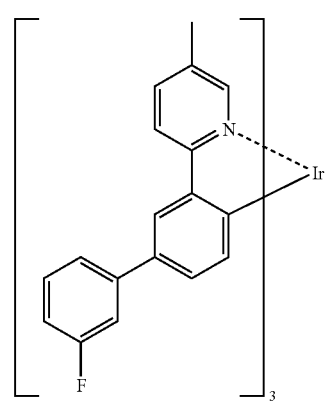
D-53
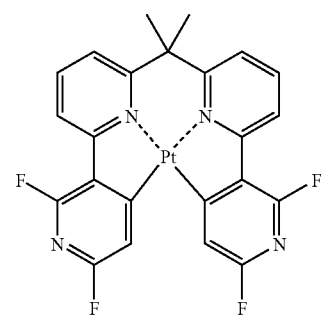
D-54
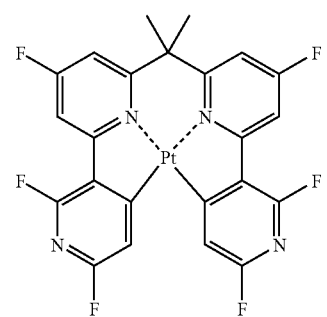
D-55
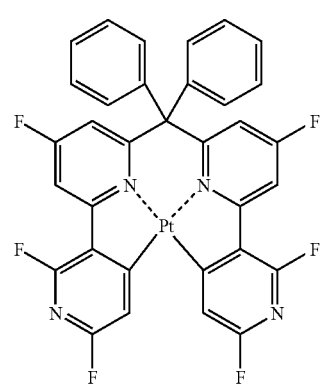
D-56
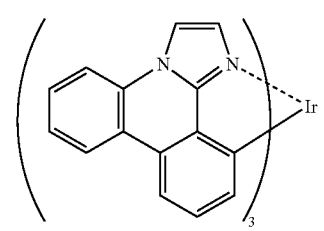
D-57
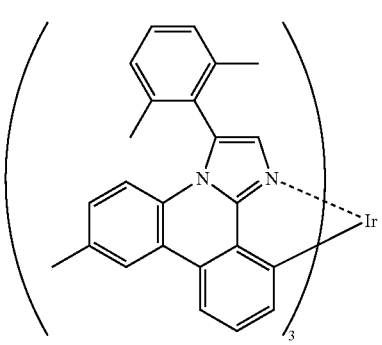
D-58
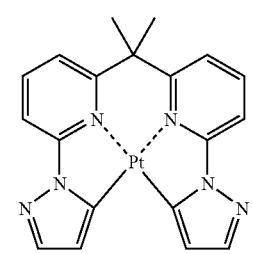
D-59
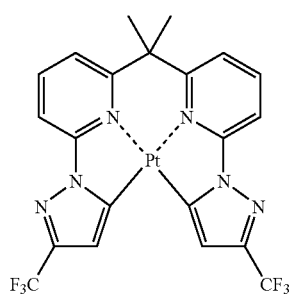

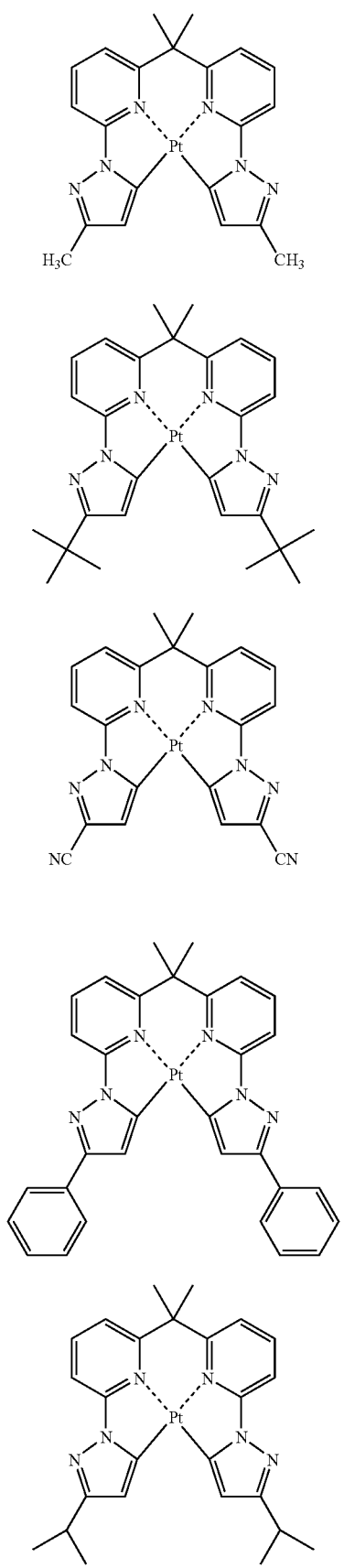
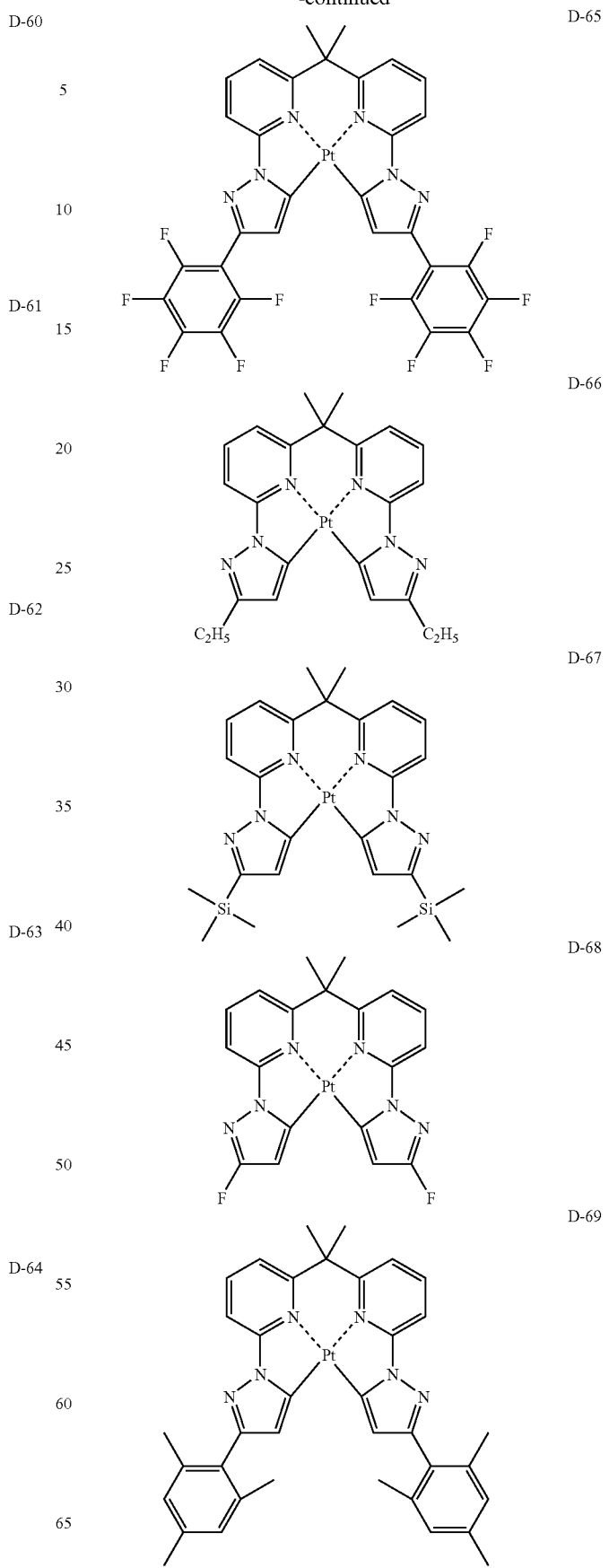

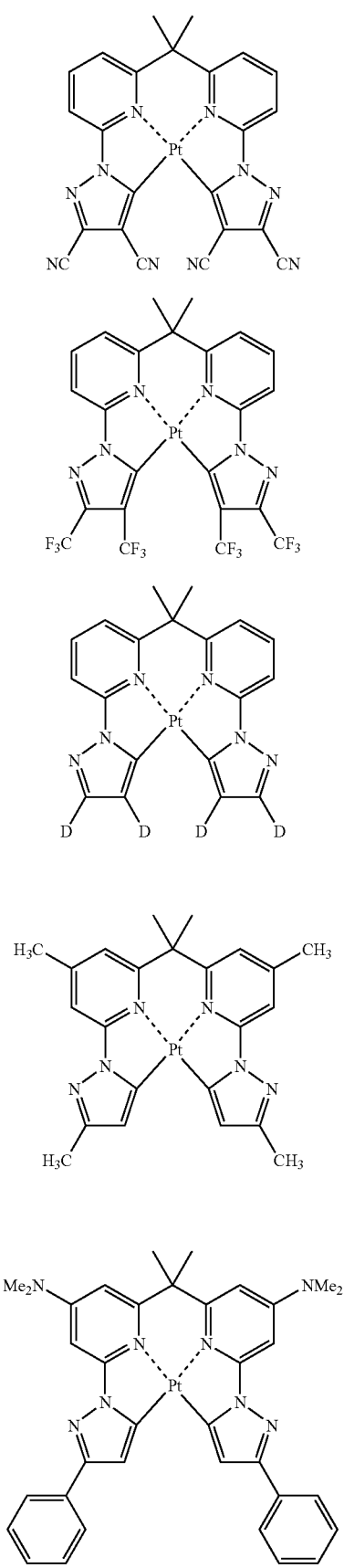
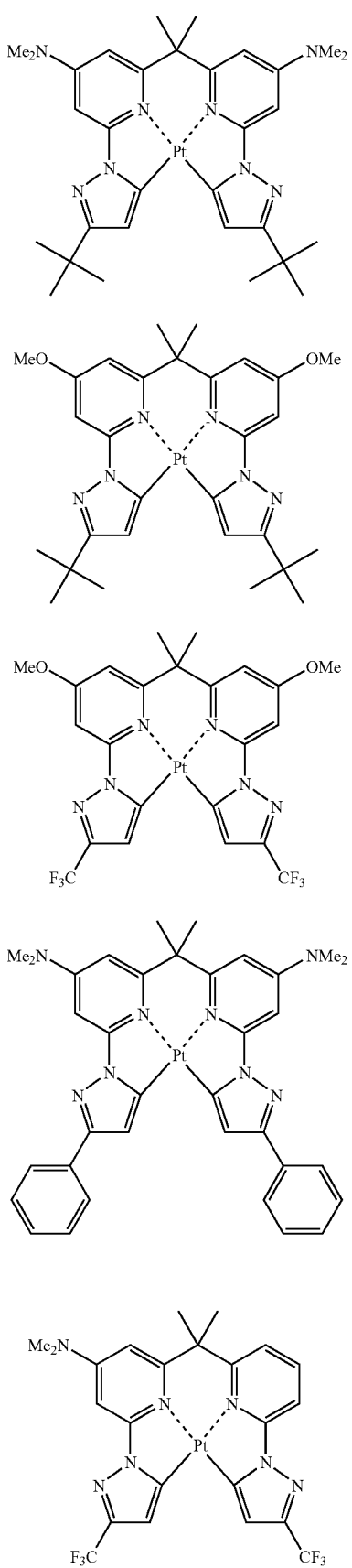

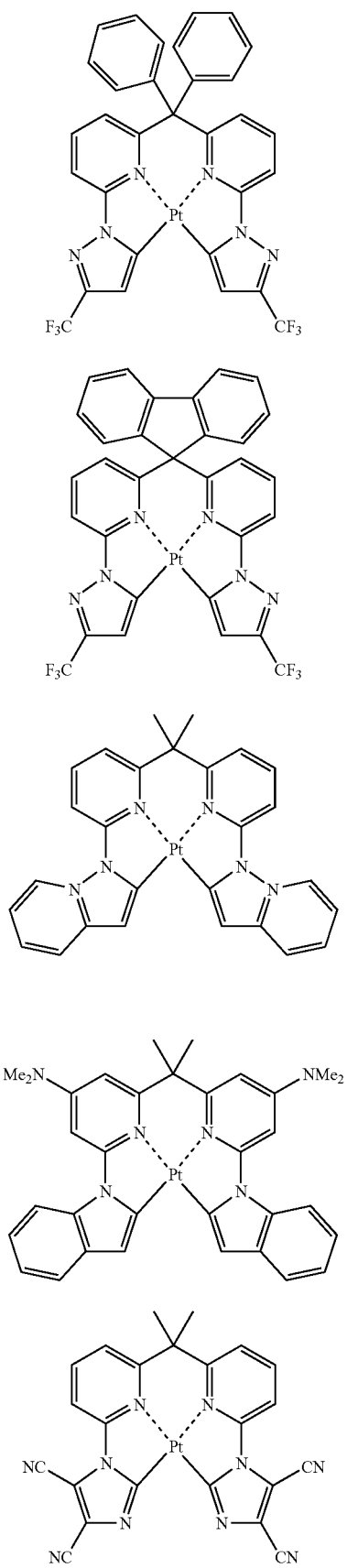
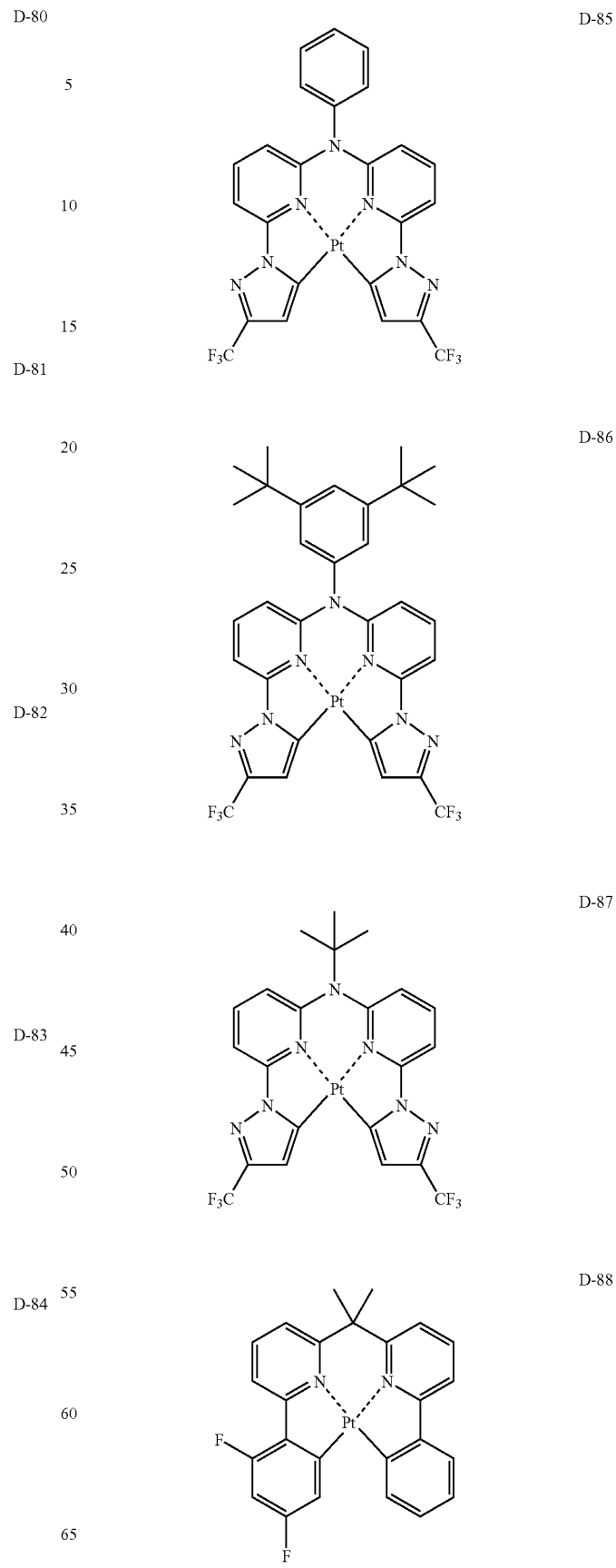

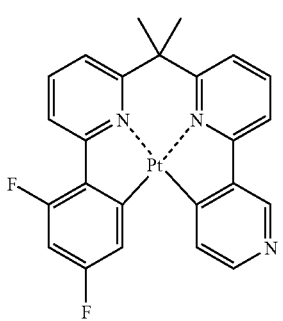
D-89
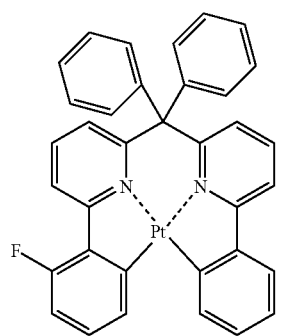
D-90
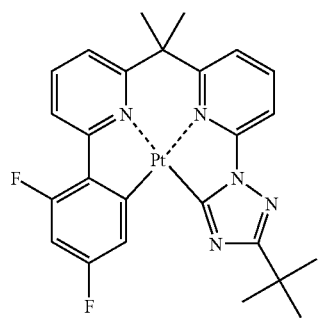
D-91
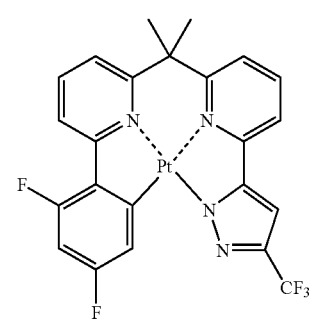
D-92
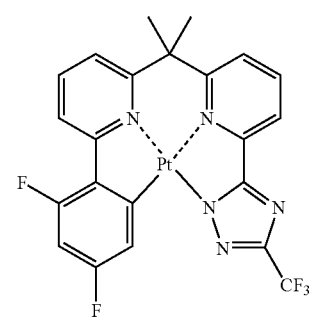
D-93
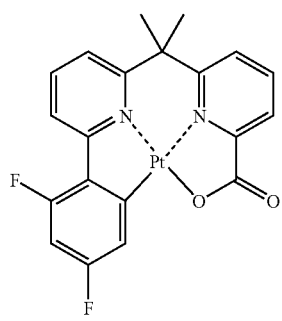
D-94
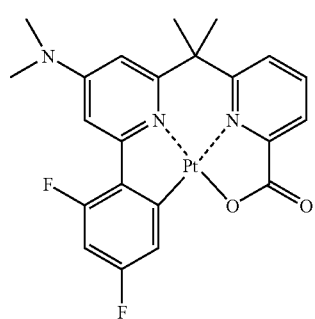
D-95
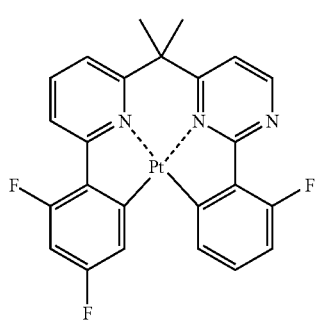
D-96
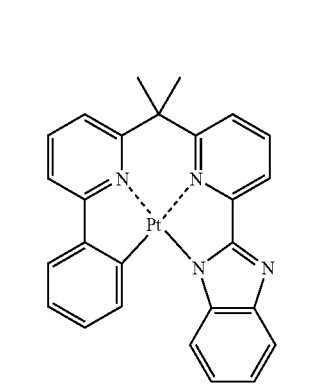
D-97
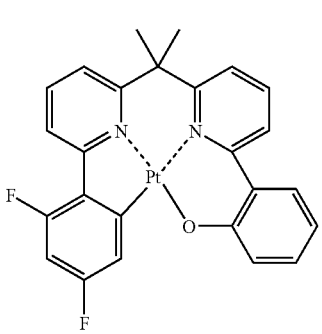
D-98

D-99 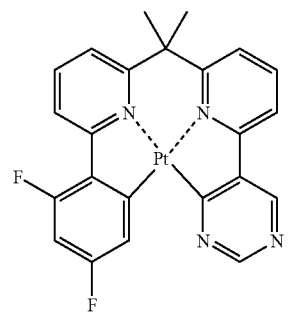
D-100 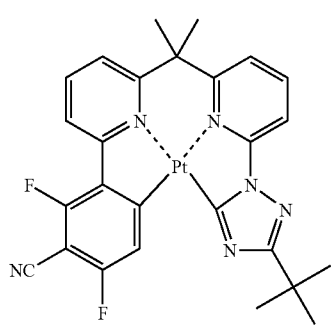
D-101 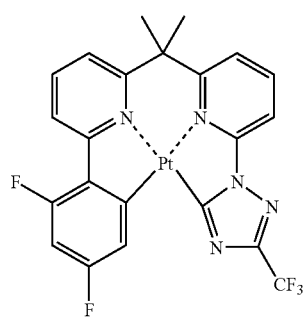
D-102 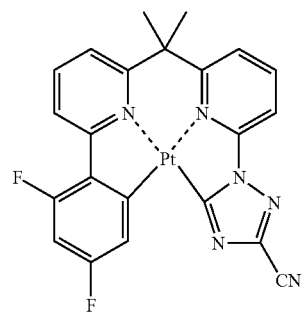
D-103 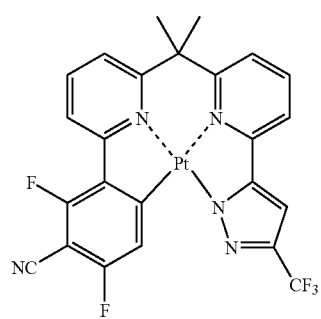
D-104 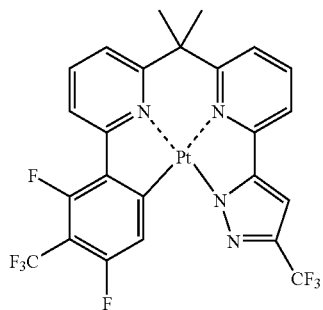
D-105 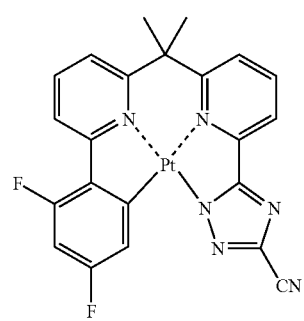
D-106 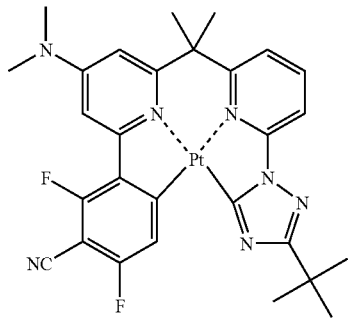
D-107 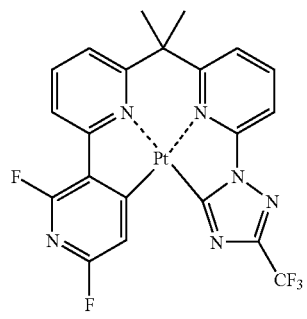
D-108 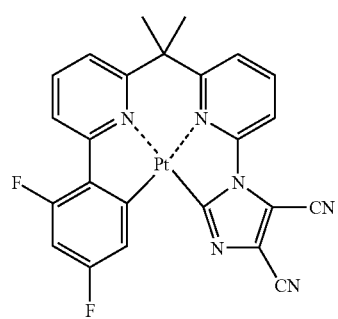

D-109
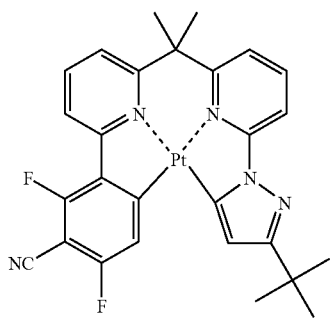
D-110
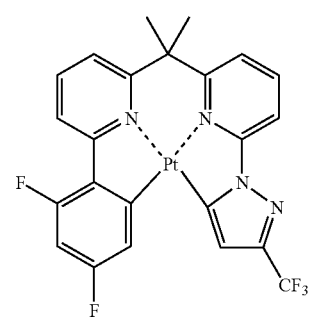
D-111
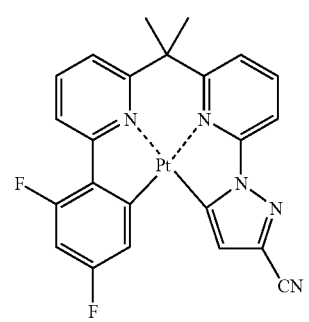
D-112
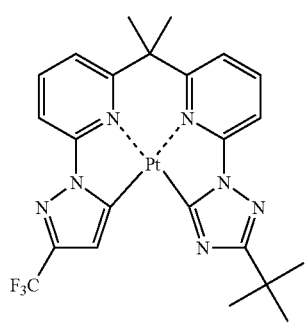
D-113
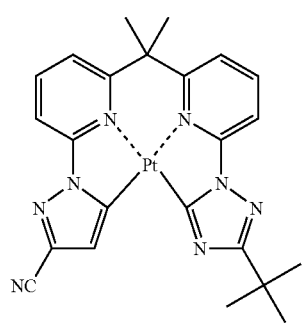
D-114
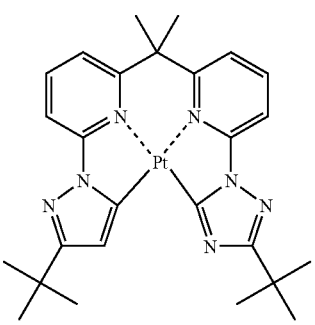
D-115
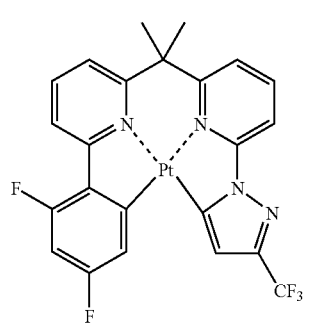
D-116
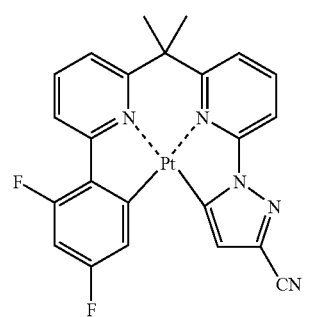
D-117
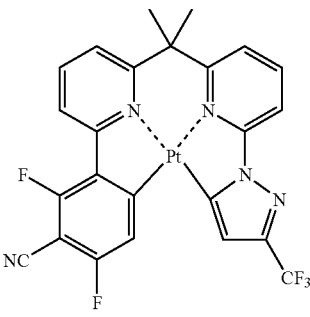
D-118
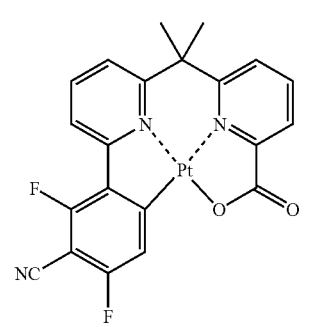

D-119 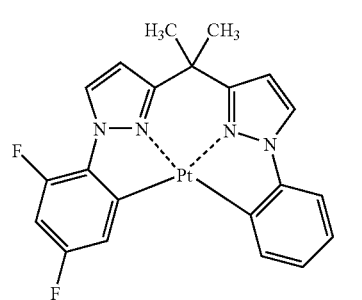
D-120 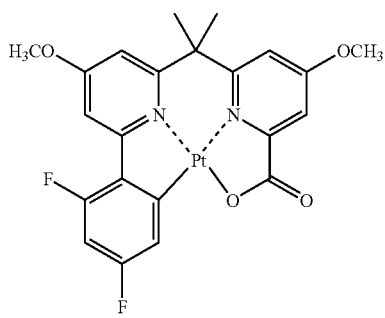
D-121 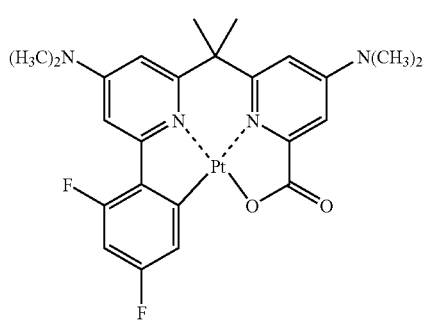
D-122 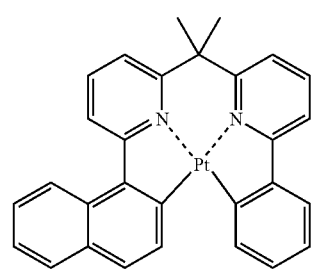
D-123 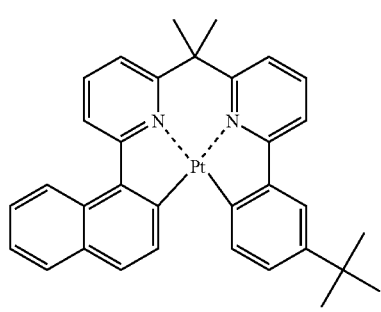
D-124 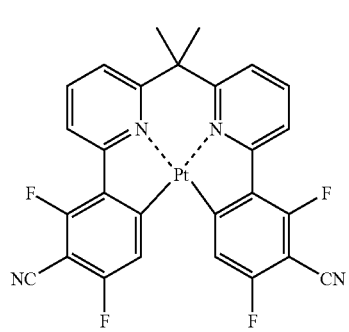
D-125 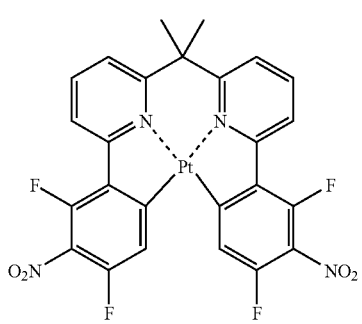
D-126 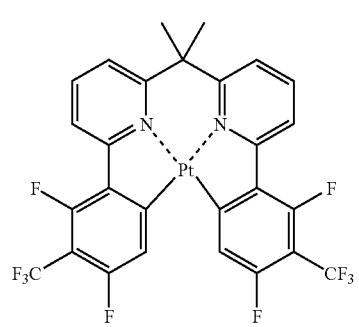
D-127 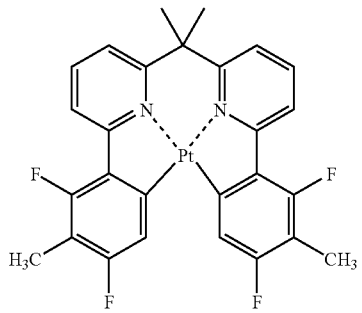
D-128 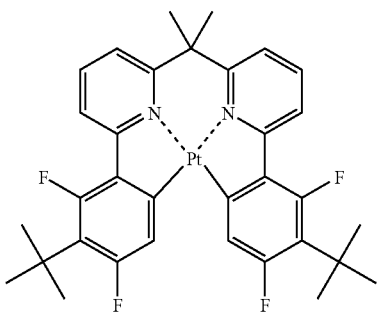

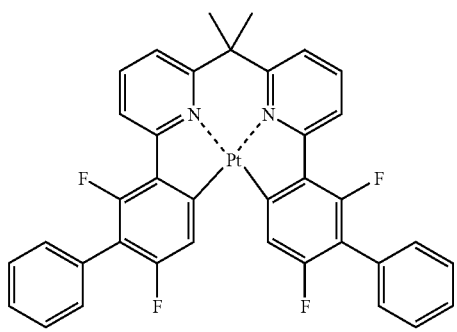
D-129
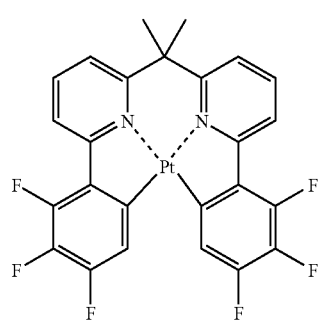
D-130
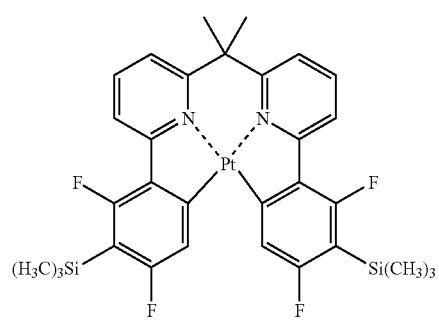
D-131
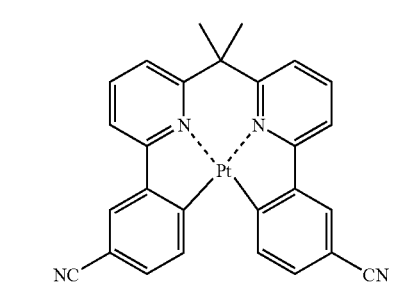
D-132
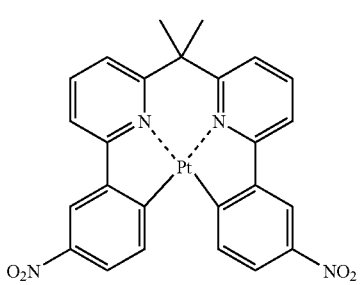
D-133
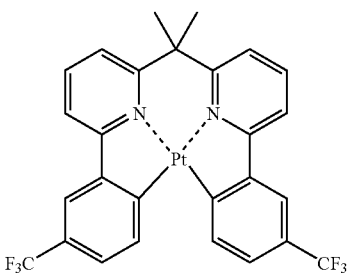
D-134
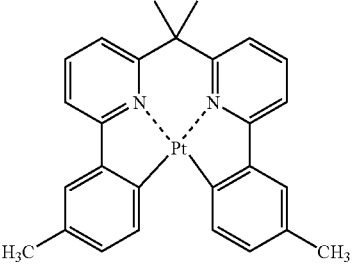
D-135
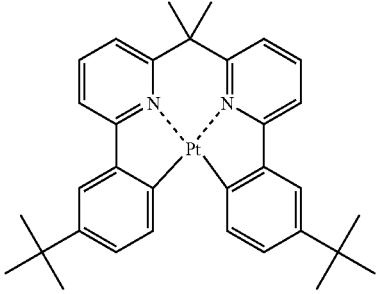
D-136
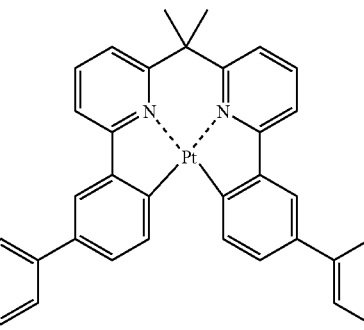
D-137
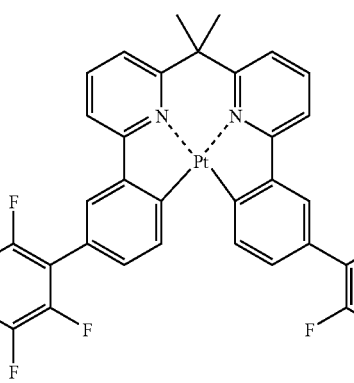
D-138

D-139
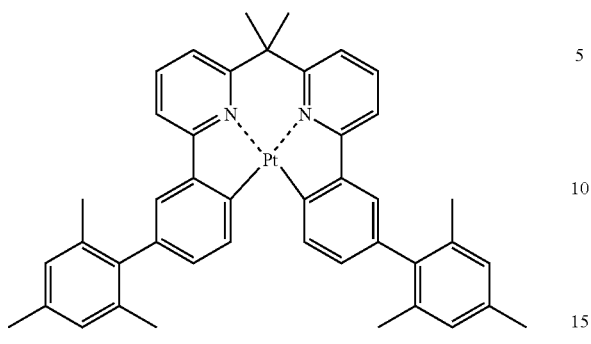
D-140
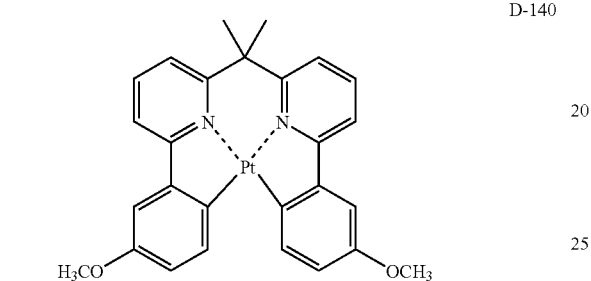
D-141
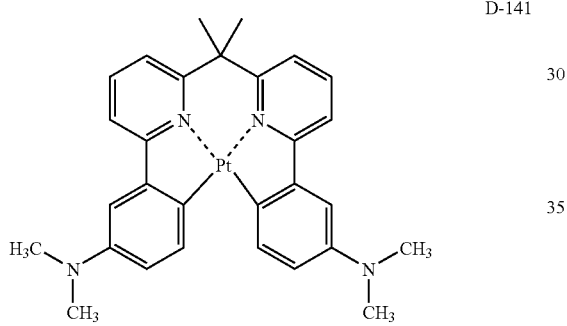
D-142
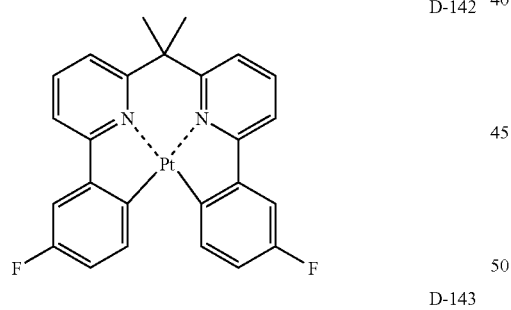
D-143
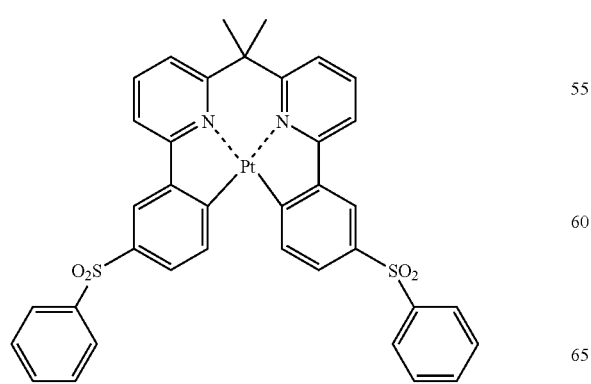
D-144
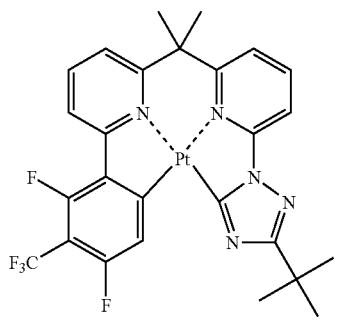
D-145
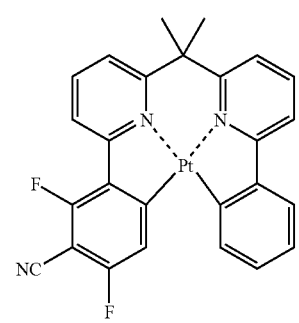
D-146
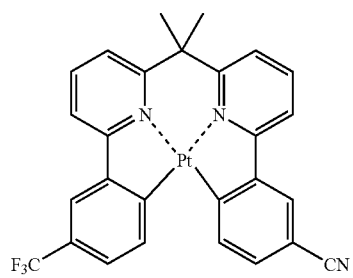
D-147
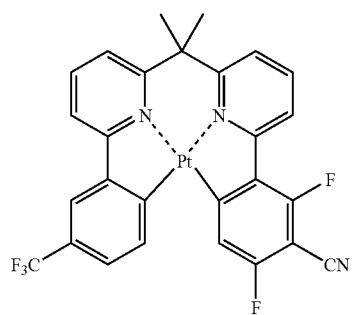
D-148
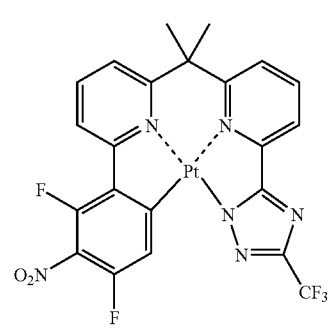

-continued

D-149
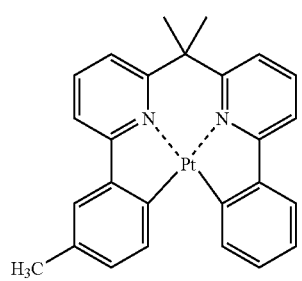

D-150
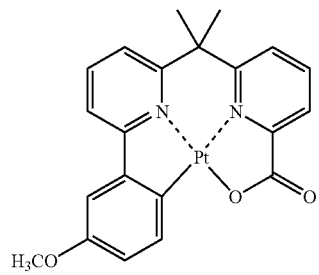

D-151
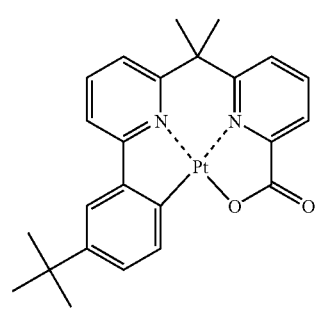

D-152
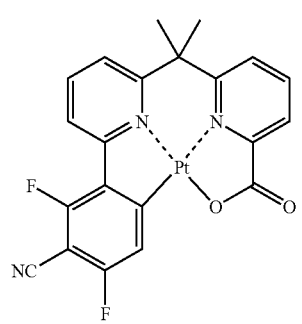

D-153
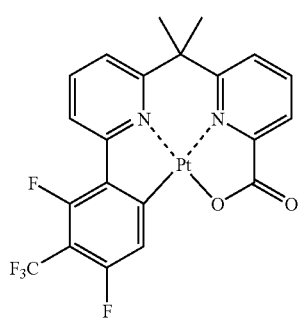

-continued

D-154
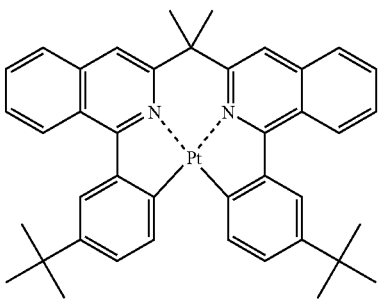

D-155
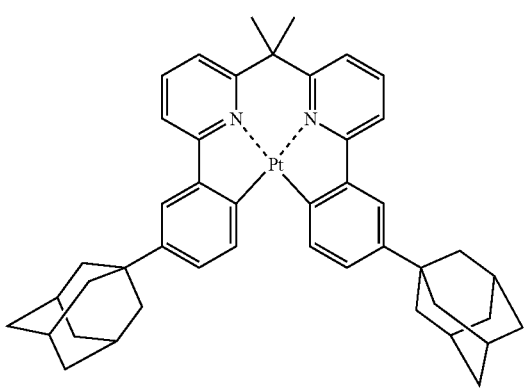

D-156
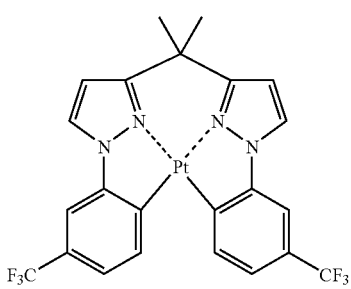

The light-emitting material is generally contained in the light-emitting layer in an amount of from 0.1 to 50 mass % based on the mass of all the compounds forming the light-emitting layer, preferably from 1 to 50 mass % in view of durability and external quantum efficiency, and more preferably from 2 to 40 mass %.

The thickness of the light-emitting layer is not especially restricted, but generally preferably the thickness is from 2 to 500 nm, more preferably from 3 to 200 nm from the viewpoint of external quantum efficiency, and still more preferably from 5 to 100 nm.

Host Materials:

As host materials for use in the invention, for example, the following materials can be exemplified besides the compound of the invention.

As host materials, a charge transporting material and a hole transporting material can be exemplified, and preferably the host material is a charge transporting material. The host material may be one kind or may be two or more kinds, and, for example, the constitution of mixture of an electron transporting host material and a hole transporting host material is exemplified.

As the host materials, various kinds of metal complexes represented by electrically conductive high molecular oligomers such as pyrrole, indole, carbazole, azaindole, azacarbazole, triazole, oxazole, oxadiazole, pyrazole, imidazole, thiophene, polyarylalkane, pyrazoline, pyrazolone, phenylenediamine, arylamine, amino-substituted chalcone, styrylanthracene, fluorenone, hydrazone, stilbene, silazane, an aromatic tertiary amine compound, a styrylamine compound, a porphyrin compound, a polysilane compound, poly (N-vinylcarbazole), an aniline copolymer, a thiophene oligomer, polythiophene, etc., organic silane, a carbon film, pyridine, pyrimidine, triazine, imidazole, pyrazole, triazole, oxazole, oxadiazole, fluorenone, anthraquinodimethane, anthrone, diphenylquinone, thiopyran dioxide, carbodiimide, fluorenylidenemethane, distyrylpyrazine, fluorine-substituted aromatic compounds, heterocyclic tetracarboxylic anhydrides such as naphthaleneperylene, etc., phthalocyanine, metal complexes of 8-quinolinol derivatives, and metal complexes having metal phthalocyanine, benzoxazole, or benzothiazole as the ligand, and derivatives thereof (which may have a substituent and a condensed ring) can be exemplified.

In the light-emitting layer in the invention, it is preferred in the points of color purity, luminous efficiency and driving durability that the lowest excitation triplet energy ($T_1$ energy) of the host material (also including the compound represented by formula (I)) is higher than $T_1$ energy of the phosphorescent material.

The content of the host compound in the invention is not especially restricted, but from the aspects of luminous efficiency and driving voltage, the content of the host compound is preferably from 15 to 95 mass % based on the mass of all the compounds forming the light-emitting layer.

Hole Injecting Layer and Hole Transporting Layer:

The hole injecting layer and the hole transporting layer are layers having functions of receiving holes from the anode or anode side and transporting the holes to the cathode side. The hole injecting material and hole transporting material used in these layers may be a low molecular weight compound or may be a polymer compound.

Specifically, these layers are preferably layers containing various metal complexes of pyrrole derivatives, carbazole derivatives, triazole derivatives, oxazole derivatives, oxadiazole derivatives, imidazole derivatives, polyarylalkane derivatives, pyrazoline derivatives, pyrazolone derivatives, phenylenediamine derivatives, arylamine derivatives, amino-substituted chalcone derivatives, styrylanthracene derivatives, fluorenone derivatives, hydrazone derivatives, stilbene derivatives, silazane derivatives, aromatic tertiary amine compounds, styrylamine compounds, phthalocyanine compounds, porphyrin compounds, thiophene derivatives, organic silane derivatives, carbon, iridium complex, etc.

The hole injecting layer or hole transporting layer of the organic EL device in the invention can contain an electron accepting dopant. As the electron accepting dopants to be introduced to the hole injecting layer or hole transporting layer, either inorganic compounds or organic compounds can be used so long as they are electron-acceptive and have a property capable of oxidizing organic compounds.

Specifically, the examples of the inorganic compounds include metal halides, such as ferric chloride, aluminum chloride, gallium chloride, indium chloride, and antimony pentachloride, and metallic oxides, such as vanadium pentoxide and molybdenum trioxide.

In the case of organic compounds, compounds having a nitro group, halogen, a cyano group or a trifluoromethyl group as the substituent, quinone compounds, acid anhydride compounds and Fullerene can be preferably used.

In addition to the above compounds, the compounds disclosed in JP-A-6-212153, JP-A-11-111463, JP-A-11-251067, JP-A-2000-196140, JP-A-2000-286054, JP-A-2000-315580, JP-A-2001-102175, JP-A-2001-160493, JP-A-2002-252085, JP-A-2002-56985, JP-A-2003-157981, JP-A-2003-217862, JP-A-2003-229278, JP-A-2004-342614, JP-A-2005-72012, JP-A-2005-166637 and JP-A-2005-209643 can be preferably used.

Of the compounds, hexacyanobutadiene, hexacyanobenzene, tetracyanoethylene, tetracyanoquinodimethane, tetrafluorotetracyanoquinodimethane, p-fluoranyl, p-chloranyl, p-bromanyl, p-benzoquinone, 2,6-dichlorobenzoquinone, 2,5-dichlorobenzoquinone, 1,2,4,5-tetracyanobenzene, 1,4-dicyanotetrafluorobenzene, 2,3-dichloro-5,6-dicyanobenzoquinone, p-dinitrobenzene, m-dinitrobenzene, o-dinitrobenzene, 1,4-naphthoquinone, 2,3-dichloronaphthoquinone, 1,3-dinitronaphthalene, 1,5-dinitronaphthalene, 9,10-anthraquinone, 1,3,6,8-tetranitrocarbazole, 2,4,7-trinitro-9-fluorenone, 2,3,5,6-tetracyanopyridine, and Fullerene C60 are preferred, hexacyanobutadiene, hexacyanobenzene, tetracyanoethylene, tetracyanoquinodimethane, tetrafluorotetracyanoquinodimethane, p-fluoranyl, p-chloranyl, p-bromanyl, 2,6-dichlorobenzoquinone, 2,5-dichlorobenzoquinone, 2,3-dichloronaphthoquinone, 1,2,4,5-tetracyanobenzene, 2,3-dichloro-5,6-dicyanobenzoquinone, and 2,3,5,6-tetracyanopyridine are more preferred, and tetrafluorotetracyanoquinodimethane is especially preferred.

These electron accepting dopants may be used by one kind alone, or two or more dopants may be used. The amount to be used of the electron accepting dopants differs according to the kind of the material, but the amount is preferably from 0.01 to 50 mass % on the basis of the material of the hole transporting layer, more preferably from 0.05 to 20 mass %, and especially preferably from 0.1 to 10 mass %.

The thickness of the hole-injecting layer and hole transporting layer is each preferably 500 nm or less in view of lowering driving voltage.

The thickness of the hole-transporting layer is preferably from 1 to 500 nm, more preferably from 5 to 200 nm, and still more preferably from 10 to 100 nm. The thickness of the hole-injecting layer is preferably from 0.1 to 200 nm, more preferably from 0.5 to 100 nm, and still more preferably from 1 to 100 nm.

The hole-injecting layer and the hole-transporting layer may have a single layer structure comprising one kind or two or more kinds of the above materials, or may be a multilayer structure comprising a plurality of layers having the same composition or different compositions.

Electron Injecting Layer and Electron Transporting Layer:

The electron-injecting layer and the electron-transporting layer are layers having functions of receiving electrons from the cathode or cathode side and transporting the electrons to the anode side. The electron-injecting material and the electron-transporting material used in these layers may be a low molecular weight compound or a polymer compound.

Specifically, these layers are preferably layers containing, besides the compounds of the invention, various metal complexes represented by metal complexes of pyridine derivatives, quinoline derivatives, pyrimidine derivatives, pyrazine derivatives, phthalazine derivatives, phenanthroline derivatives, triazine derivatives, triazole derivatives, oxazole derivatives, oxadiazole derivatives, imidazole derivatives, fluorenone derivatives, anthraquinodimethane derivatives, anthrone derivatives, diphenylquinone derivatives, thiopyran dioxide derivatives, carbodiimide derivatives, fluorenylidenemethane derivatives, distyrylpyrazine derivatives, aromatic cyclic tetracarboxylic anhydrides such as naphthalene and perylene, phthalocyanine derivatives, metal complexes of 8-quinolinol derivatives, metal complexes having metal-phthalocyanine, benzoxazole or benzothiazole as the ligand, and organic silane derivatives represented by silol.

The electron-injecting layer and the electron-transporting layer of the organic EL device of the invention can contain an electron donating dopant. The electron donating dopants to be introduced to the electron-injecting layer and the electron-transporting layer are sufficient to be electron donating and have a property capable of reducing organic compounds, and alkali metals such as Li, alkaline earth metals such as Mg, transition metals containing rare earth metals, and reductive organic compounds are preferably used. As the metals, metals having a work function of 4.2 eV or less can be preferably used, and specifically Li, Na, K, Be, Mg, Ca, Sr, Ba, Y, Cs, La, Sm, Gd, and Yb are exemplified. As the reductive organic compounds, e.g., nitrogen-containing compounds, sulfur-containing compounds and phosphorus-containing compounds are exemplified.

In addition to the above, materials disclosed in JP-A-6-212153, JP-A-2000-196140, JP-A-2003-68468, JP-A-2003-229278 and JP-A-2004-342614 can be used.

These electron-donating dopants may be used by one kind alone, or two or more kinds of dopants may be used. The amount to be used of the electron-donating dopants differs by the kinds of materials, but the amount is preferably from 0.1 to 99 mass % on the basis of the electron transporting layer material, more preferably from 1.0 to 80 mass %, and especially preferably from 2.0 to 70 mass %.

The thickness of the electron injecting layer and the electron transporting layer is preferably 500 nm or less from the point of lowering the driving voltage.

The thickness of the electron transporting layer is preferably from 1 to 500 nm, more preferably from 5 to 200 nm, and still more preferably from 10 to 100 nm. The thickness of the electron injecting layer is preferably from 0.1 to 200 nm, more preferably from 0.2 to 100 nm, and still more preferably from 0.5 to 50 nm.

The electron injecting layer and the electron transporting layer may have a single layer structure comprising one kind or two or more kinds of the above materials, or may be a multi-layer structure comprising a plurality of layers having the same composition or different compositions.

Hole-Blocking Layer:

The hole-blocking layer is a layer having a function of preventing the holes transported from the anode side to the light-emitting layer from passing through to the cathode side. In the invention, a hole-blocking layer can be provided as an organic layer contiguous to the light-emitting layer on the cathode side.

As the examples of the compounds constituting the hole-blocking layer, aluminum complexes such as aluminum(III) bis(2-methyl-8-quinolinato)-4-phenylphenolate (abbreviation: BAlq), triazole derivatives, and phenanthroline derivatives such as 2,9-dimethyl-4,7-diphenyl-1,10-phenanthroline (abbreviation: BCP) can be exemplified.

The thickness of the hole-blocking layer is preferably from 1 to 500 nm, more preferably from 5 to 200 nm, and still more preferably from 10 to 100 nm.

The hole-blocking layer may have a single layer structure comprising one kind or two or more kinds of the above materials, or may be a multilayer structure comprising a plurality of layers having the same composition or different compositions.

Electron-Blocking Layer:

The electron-blocking layer is a layer having a function of preventing the electrons transported from the cathode side to the light-emitting layer from passing through to the anode side. In the invention, an electron-blocking layer can be provided as an organic layer contiguous to the light-emitting layer on the anode side.

As the examples of the compounds constituting the electron-blocking layer, for example, the hole-transporting materials described above can be applied.

The thickness of the electron-blocking layer is preferably from 1 to 500 nm, more preferably from 5 to 200 nm, and still more preferably from 10 to 100 nm.

The electron-blocking layer may have a single layer structure comprising one kind or two or more kinds of the above materials, or may be a multilayer structure comprising a plurality of layers having the same composition or different compositions.

Protective Layer:

In the invention, the organic EL device may be entirely protected with a protective layer.

The materials contained in the protective layer are sufficient to have a function of preventing substances that accelerate deterioration of the device such as water and oxygen from entering the device.

As the examples of the materials, metals, e.g., In, Sn, Pb, Au, Cu, Ag, Al, Ti, Ni, etc., metallic oxides, e.g., MgO, SiO, $SiO_2$, $Al_2O_3$, GeO, NiO, CaO, BaO, $Fe_2O_3$, $Y_2O_3$, $TiO_2$, etc., metallic nitrides, e.g., $SiN_x$, $SiN_xO_y$, etc., metallic fluorides, e.g., $MgF_2$, LiF, $AlF_3$, $CaF_2$, etc., copolymers of any of polyethylene, polypropylene, polymethyl methacrylate, polyimide, polyurea, polytetrafluoroethylene, polychlorotrifluoroethylene, polydichlorodifluoroethylene, and chlorotrifluoroethylene with dichlorodifluoroethylene, copolymers obtained by copolymerization of tetrafluoroethylene and monomer mixture containing at least one kind of comonomer, fluorine-containing copolymers having a cyclic structure in the copolymer main chain, water-absorbing materials having a coefficient of water absorption of 1% or more, and moisture-proof materials having a coefficient of water absorption of 0.1% or less are exemplified.

The method of forming the protective layer is not especially restricted and, for example, a vacuum deposition method, a sputtering method, a reactive sputtering method, an MBE (molecular beam epitaxy) method, a cluster ion beam method, an ion plating method, a plasma polymerization method (a high frequency excitation ion plating method), a plasma CVD method, a laser CVD method, a thermal CVD method, a gas source CVD method, a coating method, a printing method, and a transfer method can be used.

Sealing Case:

The organic electroluminescence device in the invention may be entirely sealed with a sealing case.

A water-absorbing agent or an inactive liquid may be sealed in the space between the sealing case and the luminescence device. The water-absorbing agent is not especially restricted, and, for example, barium oxide, sodium oxide, potassium oxide, calcium oxide, sodium sulfate, calcium sulfate, magnesium sulfate, phosphorus pentoxide, calcium chloride, magnesium chloride, copper chloride, cesium fluoride, niobium fluoride, calcium bromide, vanadium bromide, molecular sieve, zeolite, and magnesium oxide can be exemplified. The inactive liquid is not especially restricted, and, for example, paraffins, liquid paraffins, fluorine solvents, e.g., perfluoroalkane, perfluoroamine, perfluoroether, etc., chlorine solvents, and silicone oils can be exemplified.

A method of sealing with the following shown resin sealing layer is also preferably used.

Resin Sealing Layer:

It is preferred to restrain deterioration of performance of the functional device of the invention due to oxygen and moisture by bringing into contact with air by the resin sealing layer.

Materials:

The materials of the resin sealing layer are not especially restricted, and acrylic resins, epoxy resins, fluorine resins, silicon resins, rubber resins, and ester resins can be used, and epoxy resins are preferred in the point of moisture content-preventing function. Of epoxy resins, thermosetting epoxy resins and photo-curable epoxy resins are preferred.

Manufacturing Method:

The manufacturing method of the resin sealing layer is not especially restricted and, for example, a method of coating a resin solution, a method of contact bonding or thermal contact bonding of a resin sheet, and a method of dry polymerization by deposition or sputtering are exemplified.

Film Thickness:

The thickness of the resin sealing layer is preferably 1 µm or more and 1 mm or less, more preferably 5 µm or more and 100 µm or less, and most preferably 10 µm or more and 50 µm or less. When the resin sealing layer is thinner than the above range, there is a possibility that the inorganic film is damaged when a second substrate is applied. While when the resin sealing layer is thicker than the above range, the thickness of the organic electroluminescence device itself becomes thick and a thin film property of the characteristics of the organic electroluminescence device is impaired.

Sealing Adhesive:

Sealing adhesive for use in the invention has a function of preventing water and oxygen from getting in from the edge parts.

Materials:

As the materials of the sealing adhesives, the same materials as the materials used in the resin sealing layer can be used. From the point of waterproofing, epoxy resins are preferred and photo-curable adhesives and thermosetting adhesives are preferred above all.

It is also preferred to add fillers to the above materials.

As the fillers to be added to the sealing agent, inorganic materials such as $SiO_2$, SiO (silicon oxide), SiON (silicon oxide nitride) and SiN (silicon nitride) are preferred. By the addition of fillers, the viscosity of the sealing agent increases, processing suitability is bettered, and a moisture-proofing property is improved.

Desiccant:

The sealing adhesive may contain a desiccant. As the desiccant, barium oxide, calcium oxide, and strontium oxide are preferably used.

The addition amount of the desiccant to the sealing adhesive is preferably from 0.01 to 20 mass %, and more preferably from 0.05 to 15 mass %. When the addition amount is less than the above range, the effect of the addition of the desiccant decreases, while when the amount is greater than the above range, it is difficult to uniformly disperse the desiccant in the sealing adhesive, so that not preferred.

Prescription of Sealing Adhesive:

Polymer Composition, Concentration

The sealing adhesive is not especially restricted and the above materials can be used. For example, as the photo-curable epoxy adhesive, XNR5516 (manufactured by Nagase Chemtex Corporation) can be exemplified, and it is sufficient that the desiccant is directly added thereto and dispersed.

Thickness

The coating thickness of the sealing adhesive is preferably from 1 µm to 1 mm. When the coating thickness is thinner than that, the sealing adhesive cannot be coated uniformly and not preferred. When the thickness is greater than that, a way for water to enter widens, so that not preferred.

Method of Sealing:

In the invention, a functional device can be obtained by coating the sealing adhesive containing the desiccant by means of a dispenser and the like, and superposing a second substrate thereon after coating and hardening.

Driving:

By the application of D.C. (if necessary, A.C. component may be contained) voltage (generally from 2 to 15 volts) between the anode and the cathode, or by the application of D.C. electric current, light emission of the organic electroluminescence device of the invention can be obtained.

With respect to the driving method of the organic electroluminescence device of the invention, the driving methods disclosed in JP-A-2-148687, JP-A-6-301355, JP-A-5-29080, JP-A-7-134558, JP-A-8-234685, JP-A-8-241047, Japanese Patent 2784615, U.S. Pat. Nos. 5,828,429 and 6,023,308 can be applied to the invention.

The luminescence device of the invention can be improved in the efficiency of collection of light by various known contrivances. For example, it is possible to improve efficiency of collection of light and improve external quantum efficiency by processing the shape of the substrate surface (for example, by forming a minute rugged pattern), by controlling the refractive indices of the substrate, ITO layer and organic layers, and by controlling the thicknesses of the substrate, ITO layer and organic layers.

The luminescence device of the invention may be what is called top emission system of collecting light from the anode side.

The organic EL device of the invention can take a structure of providing a charge-generating layer between each two layers of a plurality of light-emitting layers for improving luminous efficiency.

The charge-generating layer has functions of generating charge (holes and electrons) at the time of application of electric field and injecting the generated charge to the layer contiguous to the charge-generating layer.

As the material for forming the charge-generating layer, any material can be used so long as it has the above functions, and the charge-generating layer may comprise a single compound or a plurality of compounds.

Specifically, the material may be a material having conductivity, may be a material having semi-conductivity such as a doped organic layer, or may be a material having an electric insulating property, and the materials disclosed in JP-A-11-329748, JP-A-2003-272860 and JP-A-2004-39617 can be exemplified.

More specifically, transparent conductive materials such as ITO and IZO (indium zinc oxide), Fullerenes such as C60, conductive organic materials such as oligothiophene, conductive organic materials such as metallic phthalocyanines, metal-free phthalocyanines, metallic porphyrins, and metal-free porphyrins, metallic materials such as Ca, Ag, Al, Mg—Ag alloy, Al—Li alloy, and Mg—Li alloy, hole-conductive materials, electron-conductive materials, and mixtures of these materials may be used.

As the hole-conductive materials, for example, materials obtained by doping oxidants having an electron-withdrawing property such as F4-TCNQ, TCNQ, $FeCl_3$ to hole-transporting organic materials such as 2-TNATA and NPD, P-type conductive polymers, and P-type semiconductors are exemplified. As the electron-conductive materials, for example, materials obtained by doping metals or metallic compounds having a work function of less than 4.0 eV to electron-transporting organic materials, N-type conductive polymers, and N-type semiconductors are exemplified. As the N-type semiconductors, N-type Si, N-type CdS, and N-type ZnS are exemplified, and the P-type semiconductors, P-type Si, P-type dTe, and P-type CuO are exemplified.

Further, an electrically insulating material such as $V_2O_5$ can also be used as the charge-generating layer.

The charge-generating layer may be a monolayer, or a laminate of a plurality of layers. As the structure of lamination of a plurality of layers, a layer having a structure of the lamination of a material having conductivity such as a transparent conductive material or a metallic material and a hole-conductive material or an electron-conductive material, and a layer having a structure of the lamination of the hole-conductive material and the electron-conductive material are exemplified.

The thickness is not especially restricted, but is preferably from 0.5 to 200 nm, more preferably from 1 to 100 nm, still more preferably from 3 to 50 nm, and especially preferably from 5 to 30 nm.

It is preferred to select the thickness and material of the charge-generating layer so that the transmittance of visible light is 50% or more. The forming method of the charge-generating layer is not especially restricted, and the forming method of the organic layers can be used.

The charge-generating layer is formed between each two layers of a plurality of light-emitting layers, and the anode side and the cathode side of the charge generating layer may contain materials having a function of injecting charge to the contiguous layers. For heightening an electron injecting property to the layer contiguous to the anode side, electron injecting compounds such as BaO, SrO, $Li_2O$, LiCl, LiF, $MgF_2$, MgO, $CaF_2$ may be laminated on the anode side of the charge-generating layer.

Besides the above description, the materials of the charge-generating layer can be selected with reference to JP-A-2003-45676, U.S. Pat. Nos. 6,337,492, 6,107,734 and 6,872,472.

The organic EL device in the invention may have a resonator structure. For example, the organic EL device has a multilayer film mirror comprising a plurality of laminated films different in refractive index, a transparent or translucent electrode, a light-emitting layer, and a metal electrode by superposition on a transparent substrate. The light generated from the light-emitting layer repeats reflection and resonates between the multilayer film mirror and the metal electrode as reflectors.

As another preferred embodiment, a transparent or translucent electrode and a metal electrode respectively function as reflectors on a transparent substrate, and light generated from the light-emitting layer repeats reflection and resonates between them.

To form a resonance structure, effective refractive indices of two reflectors, optical path determined by the refractive index and thickness of each layer between the reflectors are adjusted to be optimal values to obtain a desired resonance wavelength. The expression of the case of the first embodiment is disclosed in JP-A-9-180883. The expression of the case of the second embodiment is disclosed in JP-A-2004-127795.

Use of the Invention:

The organic electroluminescence device in the invention can be preferably used in display devices, displays, backlights, electrophotography, illumination light sources, recording light sources, exposure light sources, reading light sources, indicators, signboards, interior designs, optical communications, and the like.

As a method of making the organic EL device full colors, for example, as described in *Monthly Display*, pp. 33-37 (September, 2000), a three-color light-emitting method of arranging organic EL devices emitting lights corresponding to three primary colors (blue (B), green (G) and red (R)) of colors on a substrate, a white color method of separating white color emission by an organic EL device for white color emission to three colors through a color filter, and a color-converting method of converting blue color emission by an organic EL device for blue color emission to red (R) and green (G) through a fluorescent dye layer are known.

Further, by using in combination of a plurality of organic EL devices different in luminescent colors capable of obtaining by the above method, plane light sources of desired luminescent colors can be obtained. For example, a white emission light source of combining luminescence devices of blue and yellow luminescence devices, and a white emission light source of combining luminescence devices of blue, green and red are exemplified.

EXAMPLES

The invention will be described in further detail with reference to examples, but the invention is by no means restricted thereto.

Synthesis Examples

Synthesis Example 1

Synthesis of Exemplified Compound 1

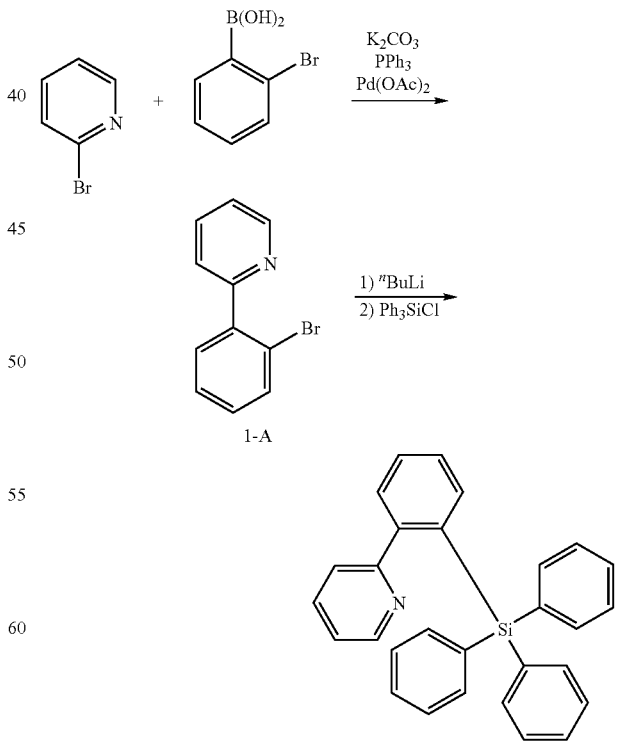

Exemplified Compound 1

Under nitrogen flow, 16.4 g of 2-bromopyridine, 25 g of 2-bromophenylboronic acid, 2.72 g of triphenylphosphine, 38.7 g of potassium carbonate, 200 ml of water, and 150 ml of 1,2-dimethoxyethane are put in a three-neck round bottom flask having a capacity of 1 liter and stirred. Palladium acetate (0.58 g) is added to the mixture and stirred while heating for 5 hours, followed by cooling up to room temperature. The obtained reaction mixture is subjected to extraction with ethyl acetate, washed with water and saturated brine in order, dried with magnesium sulfate to distill off the solvent. The reaction product is refined by silica gel column chromatography (hexane/ethyl acetate: 9/1) to obtain 15.7 g of Compound 1-A (yield: 65%).

Under nitrogen flow, 3.5 g of Compound 1-A and 70 ml of tetrahydrofuran are put in a three-neck round bottom flask having a capacity of 200 ml, and cooled up to −60° C. while stirring. n-Butyl lithium (a 1.6M hexane solution) (10.3 ml) is slowly dripped to the above mixture, and the mixture is stirred for 30 minutes after termination of dripping. A solution prepared by dissolving 5.7 g of triphenylsilyl chloride in 20 ml of tetrahydrofuran is slowly dripped into the reaction liquid at −60° C. After termination of dripping, the reaction liquid is stirred at −60° C. for 10 minutes, and the temperature is gradually raised to room temperature. The obtained reaction mixture is subjected to extraction with ethyl acetate, washed with water and saturated brine in order, and then dried with magnesium sulfate to distill off the solvent. The reaction product is refined by silica gel column chromatography (hexane/ethyl acetate: 9/1) to obtain 3.1 g of Compound 1 (yield: 50%).

$^1$H-NMR (300 MHz, CDCl$_3$) δ6.75 (1H, mC), 7.25 (10H, mC), 7.42 (8H, mC), 7.47 (1H, dd), 7.64 (2H, mC), 7.93 (1H, d)

T$_1$ energy of Compound 1 in a state of film is 72 kcal/mol.

Synthesis Example 2

Synthesis of Exemplified Compound 11

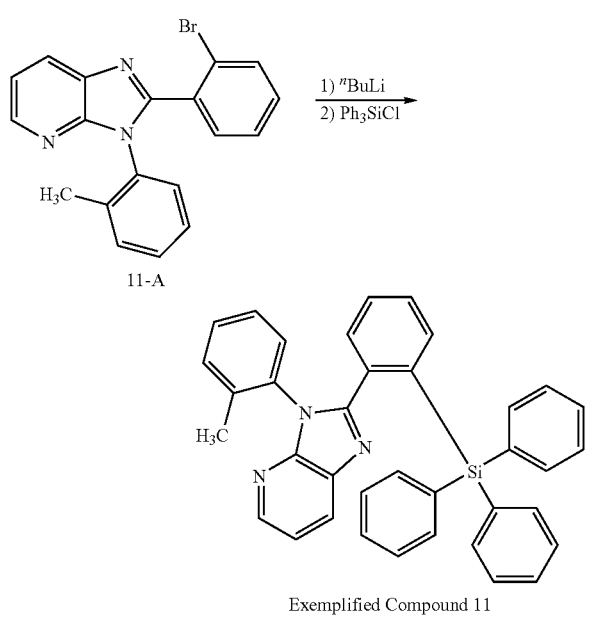

Exemplified Compound 11

Under nitrogen flow, 4 g of Compound 11-A and 80 ml of tetrahydrofuran are put in a three-neck round bottom flask having a capacity of 200 ml, and cooled up to −70° C. while stirring. n-Butyl lithium (a 1.6M hexane solution) (7.6 ml) is slowly dripped to the above mixture, and the mixture is stirred for 1 hour after termination of dripping. A solution prepared by dissolving 3.6 g of triphenylsilyl chloride in 15 ml of tetrahydrofuran is slowly dripped into the reaction liquid at −60° C. After termination of dripping, the temperature is gradually raised to room temperature. The obtained reaction mixture is subjected to extraction with ethyl acetate, washed with water and saturated brine in order, and then dried with magnesium sulfate to distill off the solvent. The reaction product is recrystallized from ethyl acetate to obtain 3.0 g of Compound 11 (yield: 51%).

$^1$H-NMR (300 MHz, CDCl$_3$) δ2.02 (3H, s), 6.84 (1H, d), 6.99 (2H, mC), 7.22 (11H, mC), 7.25-7.4 (3H, m), 7.47 (1H, dd), 7.61 (7H, mC), 8.16 (1H, dd)

T$_1$ energy of Compound 11 in a state of film is 73 kcal/mol.

Organic Electroluminescence Device:

Example 1

Manufacture of Organic Electroluminescence Device 1-1 of the Invention:

An anode substrate having a film of ITO formed on a glass substrate in a thickness of 150 nm is washed, copper phthalocyanine is deposited on the ITO film in a thickness of 10 nm (a hole injecting layer), NPD is deposited on the hole injecting layer in a thickness of 40 nm (a hole transporting layer), Compound 1 of the invention and Ir(ppy)$_3$ in a mass ratio of 92/8 is deposited thereon in a thickness of 40 nm (a light-emitting layer), BAlq is deposited thereon in a thickness of 30 nm (an electron transporting layer), lithium fluoride is deposited thereon in a thickness of 1 nm, a patterned mask is installed, and aluminum is deposited as the cathode in a thickness of about 70 nm. Each layer is formed according to a resistance heating vacuum deposition method. The manufactured device is sealed with a stainless steel sealing case and an ultraviolet-curable adhesive under nitrogen gas to obtain Organic Electroluminescence Device 1-1 of the invention.

Manufacture of Organic Electroluminescence Device 1-2 of the Invention:

Organic Electroluminescence Device 1-2 of the invention is manufactured in the same manner as in the manufacture of_Organic Electroluminescence Device 1-1 of the invention except for using Compound 11 of the invention in place of Compound 1 of the invention.

Manufacture of Organic Electroluminescence Device 1-3 of the Invention:

Organic Electrolumninescence Device 1-3 of the invention is manufactured in the same manner as in the manufacture of_Organic Electroluminescence Device 1-1 of the invention except for using Compound 31 of the invention in place of Compound 1 of the invention.

Manufacture of Comparative Device 1-1:

Comparative Device 1-1 is manufactured in the same manner as in the manufacture of Organic Electroluminescence Device 1-1 of the invention except for using Compound M1 (the compound disclosed in Patent Document 3, p. 149, "specified substance 54") in place of Compound 1 of the invention.

Manufacture of Comparative Device 1-2:

Comparative Device 1-2 is manufactured in the same manner as in the manufacture of Organic Electroluminescence Device 1-1 of the invention except for using Compound X1 (the compound disclosed in Patent Document 4, p. 60 and claim 49) in place of Compound 1 of the invention.

Manufacture of Comparative Device 1-3:

Comparative Device 1-3 is manufactured in the same manner as in the manufacture of Organic Electroluminescence Device 1-1 of the invention except for using Compound F31 (the compound disclosed in Patent Document 5, p. 11) in place of Compound 1 of the invention.

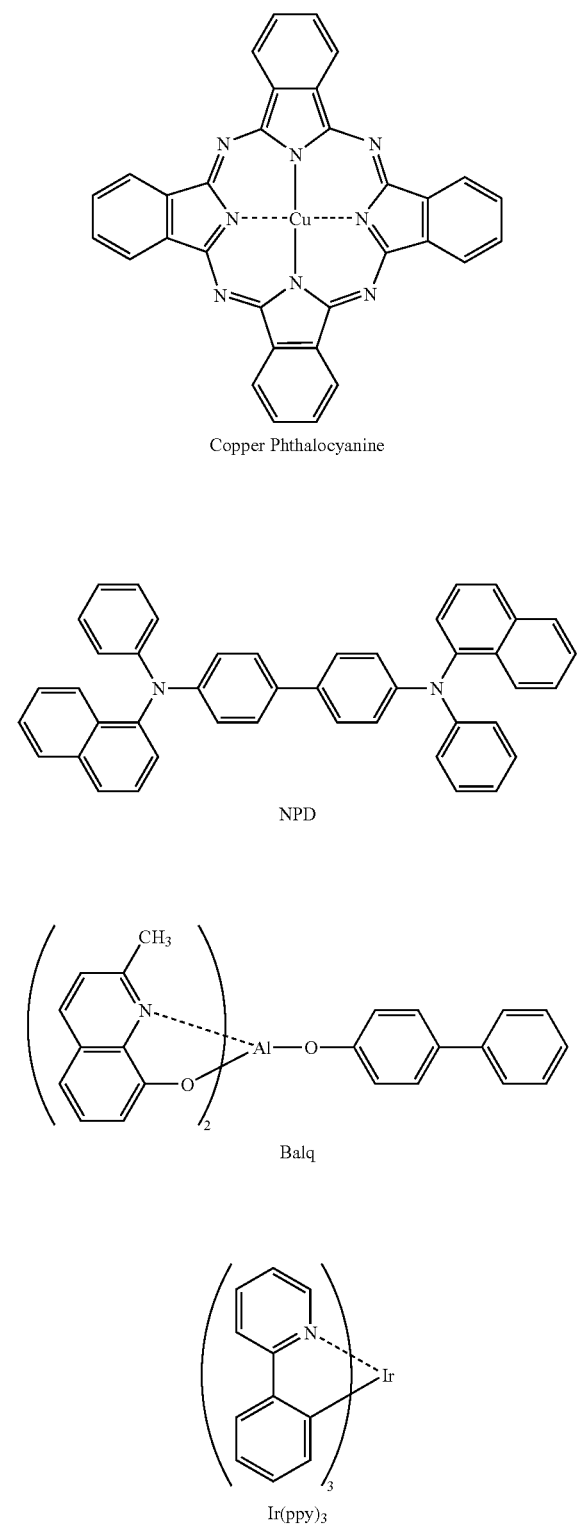

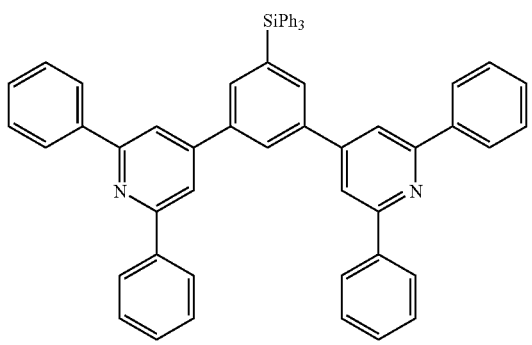

M1

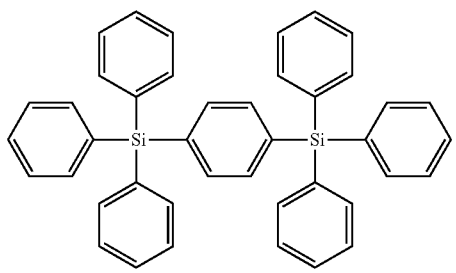

X1

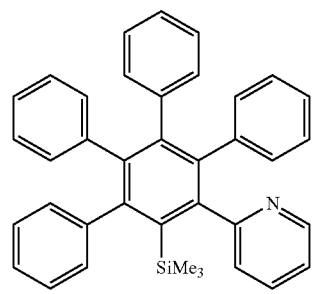

F-31

Evaluation of Performance of the Organic Electroluminescence Device:

(a) External Quantum Efficiency

DC voltage is applied to each device for light emission with source measure unit Model 2400 (manufactured by Toyo Corporation). The luminance at that time is measured with a luminometer BM-8 (manufactured by Topcon Corporation). The light emission spectrum and emission wavelength are measured with a spectrum analyzer PMA-11 (manufactured by Hamamatsu Photonics K.K.). On the basis of these measurements, external quantum efficiency around 1,000 cd/m$^2$ of luminance is computed according to a luminance conversion method.

(b) Driving Durability

DC voltage is applied to each device so as to reach luminance of 1,000 cd/m$^2$, and the time required to reach luminance of 500 cd/m$^2$ is measured. This half life time of luminance is taken as the index of evaluation of driving durability.

(c) Driving Voltage

DC voltage is applied to each device so as to reach luminance of 1,000 cd/m$^2$ for light emission, and the applied voltage is taken as the index of evaluation of driving voltage.

The results obtained are shown in Table 1 below.

TABLE 1

|  | External Quantum Efficiency in Relative Value | Driving Durability in Relative Value | Driving Voltage in Relative Value |
| --- | --- | --- | --- |
| Organic EL device 1-1 of the invention | 10 | 100 | 10 |
| Organic EL device 1-2 of the invention | 9 | 90 | 11 |
| Organic EL device 1-3 of the invention | 14 | 130 | 9 |
| Comparative device 1-1 | 3 | 45 | 13 |
| Comparative device 1-2 | 9 | 25 | 18 |
| Comparative device 1-3 | 6 | 60 | 11 |

As is apparent from the above results, the devices of the invention are high in external quantum efficiency, excellent in driving durability, and low in driving voltage as compared with the comparative devices.

Example 2

Manufacture of Organic Electroluminescence Device 2-1 of the Invention:

An anode substrate having a film of ITO formed on a glass substrate in a thickness of 150 nm is washed, copper phthalocyanine is deposited on the ITO film in a thickness of 10 nm (a hole injecting layer), NPD is deposited on the hole injecting layer in a thickness of 30 nm (a hole transporting layer), Compound 15 of the invention and compound i-1 in a mass ratio of 80/20 is deposited thereon in a thickness of 50 nm (a light-emitting layer), BAlq is deposited thereon in a thickness of 30 nm (an electron transporting layer), lithium fluoride is deposited thereon in a thickness of 1 nm, a patterned mask is installed, and aluminum is deposited as the cathode in a thickness of about 70 nm. Each layer is formed according to a resistance heating vacuum deposition method. The manufactured device is sealed with a stainless steel sealing case and an ultraviolet-curable adhesive under nitrogen gas to obtain Organic Electroluminescence Device 2-1 of the invention.

Manufacture of Comparative Device 2-1:

Comparative Device 2-1 is manufactured in the same manner as in the manufacture of Organic Electroluminescence Device 2-1 of the invention except for using Compound M1 in place of Compound 15 of the invention.

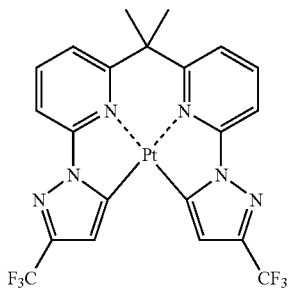

i-1

The organic electroluminescence devices are evaluated in the same manner as in Example 1, and the results obtained are shown in Table 2 below.

TABLE 2

|  | External Quantum Efficiency in Relative Value | Driving Durability in Relative Value | Driving Voltage in Relative Value |
| --- | --- | --- | --- |
| Organic EL device 2-1 of the invention | 10 | 100 | 10 |
| Comparative device 2-1 | 1 | 11 | 11 |

As is apparent from the above results, the device of the invention is high in external quantum efficiency, excellent in driving durability, and low in driving voltage as compared with the comparative device.

Example 3

Manufacture of Organic Electroluminescence Device 3-1 of the Invention:

An anode substrate having a film of ITO formed on a glass substrate in a thickness of 150 nm is washed, copper phthalocyanine is deposited on the ITO film in a thickness of 10 nm (a hole injecting layer), NPD is deposited on the hole injecting layer in a thickness of 30 nm (a hole transporting layer), Compound 1 of the invention, mCP and compound i-1 in a mass ratio of 20/65/15 is deposited thereon in a thickness of 60 nm (a light-emitting layer), BAlq is deposited thereon in a thickness of 30 nm (an electron transporting layer), lithium fluoride is deposited thereon in a thickness of 1 nm, a patterned mask is installed, and aluminum is deposited as the cathode in a thickness of about 70 nm. Each layer is formed according to a resistance heating vacuum deposition method. The manufactured device is sealed with a stainless steel sealing case and an ultraviolet-curable adhesive under nitrogen gas to obtain Organic Electroluminescence Device 3-1 of the invention.

Manufacture of Organic Electroluminescence Device 3-2 of the Invention:

Organic Electroluminescence Device 3-2 of the invention is manufactured in the same manner as in the manufacture of_Organic Electroluminescence Device 3-1 of the invention except for using Compound 31 of the invention in place of Compound 1 of the invention.

Manufacture of Comparative Device 3-1:

Comparative Device 3-1 is manufactured in the same manner as in the manufacture of Organic Electroluminescence Device 3-1 of the invention except for using Compound M1 in place of Compound 1 of the invention.

Manufacture of Comparative Device 3-2:

Comparative Device 3-2 is manufactured in the same manner as in the manufacture of Organic Electroluminescence Device 3-1 of the invention except for using Compound X1 in place of Compound 1 of the invention.

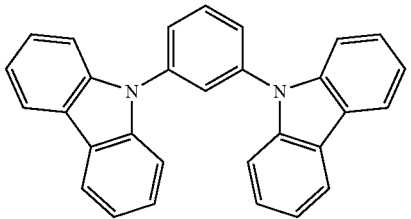

mCP

The organic electroluminescence devices are evaluated in the same manner as in Example 1, and the results obtained are shown in Table 3 below.

TABLE 3

|  | External Quantum Efficiency in Relative Value | Driving Durability in Relative Value | Driving Voltage in Relative Value |
|---|---|---|---|
| Organic EL device 3-1 of the invention | 10 | 100 | 10 |
| Organic EL device 3-2 of the invention | 10 | 120 | 8 |
| Comparative device 3-1 | 1 | 30 | 14 |
| Comparative device 3-2 | 7 | 33 | 16 |

As is apparent from the above results, the devices of the invention are high in external quantum efficiency, excellent in driving durability, and low in driving voltage as compared with the comparative devices.

Example 4

Manufacture of Organic Electroluminescence Device 4-1 of the Invention:

Organic Electroluminescence Device 4-1 of the invention is manufactured in the same manner as in the manufacture of_Organic Electroluminescence Device 2-1 of the invention except for using Compound i-2 in place of Compound i-1.

Manufacture of Organic Electroluminescence Device 4-2 of the Invention:

Organic Electroluminescence Device 4-2 of the invention is manufactured in the same manner as in the manufacture of_Organic Electroluminescence Device 4-1 of the invention except for using Compound 26 of the invention in place of Compound 15 of the invention.

Manufacture of Comparative Device 4-1:

Comparative Device 4-1 is manufactured in the same manner as in the manufacture of Organic Electroluminescence Device 4-1 of the invention except for using Compound M1 in place of Compound 15 of the invention.

Manufacture of Comparative Device 4-2:

Comparative Device 4-2 is manufactured in the same manner as in the manufacture of Organic Electroluminescence Device 4-1 of the invention except for using Compound X1 in place of Compound 15 of the invention.

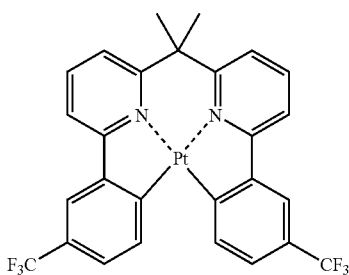

i-2

The organic electroluminescence devices are evaluated in the same manner as in Example 1, and the results obtained are shown in Table 4 below.

TABLE 4

|  | External Quantum Efficiency in Relative Value | Driving Durability in Relative Value | Driving Voltage in Relative Value |
|---|---|---|---|
| Organic EL device 4-1 of the invention | 10 | 100 | 10 |
| Organic EL device 4-2 of the invention | 13 | 110 | 9 |
| Comparative device 4-1 | 6 | 54 | 15 |
| Comparative device 4-2 | 9 | 46 | 17 |

As is apparent from the above results, the devices of the invention are high in external quantum efficiency, excellent in driving durability, and low in driving voltage as compared with the comparative devices.

Example 5

Manufacture of Organic Electroluminescence Device 5-1 of the Invention:

Organic Electroluminescence Device 5-1 of the invention is manufactured in the same manner as in the manufacture of_Organic Electroluminescence Device 3-1 of the invention except for using Compound i-3 in place of Compound i-1.

Manufacture of Organic Electroluminescence Device 5-2 of the Invention:

Organic Electroluminescence Device 5-2 of the invention is manufactured in the same manner as in the manufacture of_Organic Electroluminescence Device 5-1 of the invention except for using Compound 31 of the invention in place of Compound 1 of the invention.

Manufacture of Comparative Device 5-1:

Comparative Device 5-1 is manufactured in the same manner as in the manufacture of Organic Electroluminescence Device 5-1 of the invention except for using Compound M1 in place of Compound 1 of the invention.

Manufacture of Comparative Device 5-2:

Comparative Device 5-2 is manufactured in the same manner as in the manufacture of Organic Electroluminescence Device 5-1 of the invention except for using Compound X1 in place of Compound 1 of the invention.

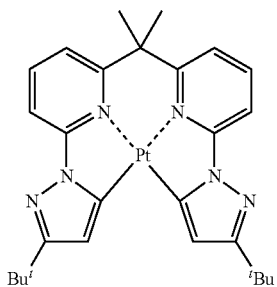

i-3

The organic electroluminescence devices are evaluated in the same manner as in Example 1, and the results obtained are shown in Table 5 below.

TABLE 5

|  | External Quantum Efficiency in Relative Value | Driving Durability in Relative Value | Driving Voltage in Relative Value |
| --- | --- | --- | --- |
| Organic EL device 5-1 of the invention | 10 | 100 | 10 |
| Organic EL device 5-2 of the invention | 11 | 130 | 8 |
| Comparative device 5-1 | 2 | 10 | 13 |
| Comparative device 5-2 | 5 | 22 | 16 |

As is apparent from the above results, the devices of the invention are high in external quantum efficiency, excellent in driving durability, and low in driving voltage as compared with the comparative devices.

Example 6

Manufacture of Organic Electroluminescence Device 6-1 of the Invention:

Organic Electroluminescence Device 6-1 of the invention is manufactured in the same manner as in the manufacture of_Organic Electroluminescence Device 1-1 of the invention except for using Compound FR-1 in place of Compound Ir(ppy)$_3$.

Manufacture of Organic Electroluminescence Device 6-2 of the Invention:

Organic Electroluminescence Device 6-2 of the invention is manufactured in the same manner as in the manufacture of_Organic Electroluminescence Device 6-1 of the invention except for using Compound 11 of the invention in place of Compound 1 of the invention.

Manufacture of Comparative Device 6-1:

Comparative Device 6-1 is manufactured in the same manner as in the manufacture of Organic Electroluminescence Device 6-1 of the invention except for using Compound X1 in place of Compound 1 of the invention.

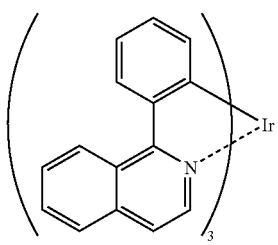

FR-1

The organic electroluminescence devices are evaluated in the same manner as in Example 1, and the results obtained are shown in Table 6 below.

TABLE 6

|  | External Quantum Efficiency in Relative Value | Driving Durability in Relative Value | Driving Voltage in Relative Value |
| --- | --- | --- | --- |
| Organic EL device 6-1 of the invention | 10 | 100 | 10 |
| Organic EL device 6-2 of the invention | 10 | 150 | 8 |
| Comparative device 6-1 | 4 | 30 | 15 |

As is apparent from the above results, the devices of the invention are high in external quantum efficiency, excellent in driving durability, and low in driving voltage as compared with the comparative device.

Example 7

Manufacture of Organic Electroluminescence Device 7-1 of the Invention:

An anode substrate having a film of ITO formed on a glass substrate in a thickness of 150 nm is washed, copper phthatocyanine is deposited on the ITO film in a thickness of 10 nm (a hole injecting layer), NPD is deposited on the hole injecting layer in a thickness of 50 nm (a hole transporting layer), Compound 1 of the invention and Rubrene in a mass ratio of 97/3 is deposited thereon in a thickness of 10 nm (a light-emitting layer), Alq is deposited thereon in a thickness of 30 nm (an electron transporting layer), lithium fluoride is deposited thereon in a thickness of 1 nm, a patterned mask is installed, and aluminum is deposited as the cathode in a thickness of about 70 nm. Each layer is formed according to a resistance heating vacuum deposition method. The manufactured device is sealed with a stainless steel sealing case and an ultraviolet-curable adhesive under nitrogen gas to obtain Organic Electroluminescence Device 7-1 of the invention.

Manufacture of Organic Electroluminescence Device 7-2 of the Invention:

Organic Electroluminescence Device 7-2 of the invention is manufactured in the same manner as in the manufacture of_Organic Electroluminescence Device 7-1 of the invention except for using Compound 11 of the invention in place of Compound 1 of the invention.

Manufacture of Comparative Device 7-1:

Comparative Device 7-1 is manufactured in the same manner as in the manufacture of Organic Electroluminescence Device 7-1 of the invention except for using Compound X1 in place of Compound 1 of the invention.

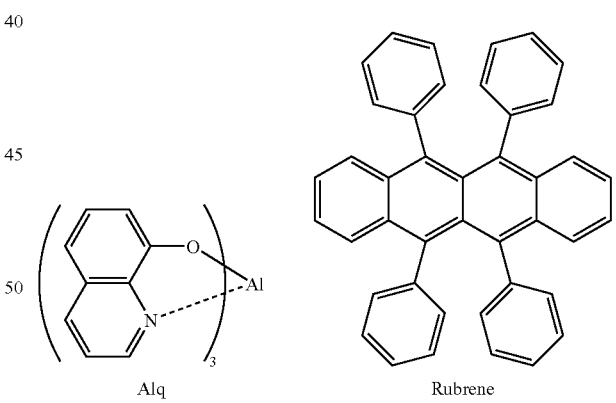

Alq    Rubrene

The organic electroluminescence devices are evaluated in the same manner as in Example 1, and the results obtained are shown in Table 7 below.

TABLE 7

|  | External Quantum Efficiency in Relative Value | Driving Durability in Relative Value | Driving Voltage in Relative Value |
| --- | --- | --- | --- |
| Organic EL device 7-1 of the invention | 10 | 100 | 10 |

TABLE 7-continued

|  | External Quantum Efficiency in Relative Value | Driving Durability in Relative Value | Driving Voltage in Relative Value |
|---|---|---|---|
| Organic EL device 7-2 of the invention | 11 | 140 | 8 |
| Comparative device 7-1 | 7 | 10 | 20 |

As is apparent from the above results, the devices of the invention are high in external quantum efficiency, excellent in driving durability, and low in driving voltage as compared with the comparative device.

Example 8

Manufacture of Organic Electroluminescence Device 8-1 of the Invention:

An anode substrate having a film of ITO formed on a glass substrate in a thickness of 150 nm is washed, copper phthalocyanine is deposited on the ITO film in a thickness of 10 nm (a hole injecting layer), NPD is deposited on the hole injecting layer in a thickness of 40 nm (a hole transporting layer), Compound mCP and Compound i-1 in a mass ratio of 88/12 is deposited thereon in a thickness of 80 nm (a light-emitting layer), Compound 11 of the invention is deposited thereon in a thickness of 15 nm, BAlq is deposited thereon in a thickness of 15 nm (an electron transporting layer), lithium fluoride is deposited thereon in a thickness of 1 nm, and a patterned mask is installed, and aluminum is deposited as the cathode in a thickness of about 70 nm. Each layer is formed according to a resistance heating vacuum deposition method. The manufactured device is sealed with a stainless steel sealing case and an ultraviolet-curable adhesive under nitrogen gas to obtain Organic Electroluminescence Device 8-1 of the invention.

Manufacture of Organic Electroluminescence Device 8-2 of the Invention:

Organic Electroluminescence Device 8-2 of the invention is manufactured in the same manner as in the manufacture of_Organic Electroluminescence Device 8-1 of the invention except for using Compound 30 of the invention in place of Compound 11 of the invention.

Manufacture of Comparative Device 8-1:

Comparative Device 8-1 is manufactured in the same manner as in the manufacture of Organic Electroluminescence Device 8-1 of the invention except for using Compound X1 in place of Compound 11 of the invention.

Manufacture of Comparative Device 8-2:

Comparative Device 8-2 is manufactured in the same manner as in the manufacture of Organic Electroluminescence Device 8-1 of the invention except for using Compound Alq in place of Compound 11 of the invention.

The organic electroluminescence devices are evaluated in the same manner as in Example 1, and the results obtained are shown in Table 8 below.

TABLE 8

|  | External Quantum Efficiency in Relative Value | Driving Durability in Relative Value | Driving Voltage in Relative Value |
|---|---|---|---|
| Organic EL device 8-1 of the invention | 10 | 100 | 10 |
| Organic EL device 8-2 of the invention | 9 | 85 | 12 |

TABLE 8-continued

|  | External Quantum Efficiency in Relative Value | Driving Durability in Relative Value | Driving Voltage in Relative Value |
|---|---|---|---|
| Comparative device 8-1 | 4 | 8 | 24 |
| Comparative device 8-2 | 1 | 33 | 18 |

As is apparent from the above results, the devices of the invention are high in external quantum efficiency, excellent in driving durability, and low in driving voltage as compared with the comparative devices.

Example 9

Manufacture of Organic Electroluminescence Device 9-1 of the Invention:

Organic Electroluminescence Device 9-1 of the invention is manufactured in the same manner as in the manufacture of_Organic Electroluminescence Device 6-1 of the invention except for using Compound D-16 in place of Compound FR-1.

Manufacture of Organic Electroluminescence Device 9-2 of the Invention:

Organic Electroluminescence Device 9-2 of the invention is manufactured in the same manner as in the manufacture of_Organic Electroluminescence Device 9-1 of the invention except for using Compound 11 of the invention in place of Compound 1 of the invention.

Manufacture of Comparative Device 9-1:

Comparative Device 9-1 is manufactured in the same manner as in the manufacture of Organic Electroluminescence Device 9-1 of the invention except for using Compound X1 in place of Compound 1 of the invention.

The organic electroluminescence devices are evaluated in the same manner as in Example 1, and the results obtained are shown in Table 9 below.

TABLE 9

|  | External Quantum Efficiency in Relative Value | Driving Durability in Relative Value | Driving Voltage in Relative Value |
|---|---|---|---|
| Organic EL device 9-1 of the invention | 10 | 100 | 10 |
| Organic EL device 9-2 of the invention | 10 | 150 | 9 |
| Comparative device 9-1 | 3 | 43 | 20 |

Example 10

Manufacture of Organic Electroluminescence Device 10-1 of the Invention:

Organic Electroluminescence Device 10-1 of the invention is manufactured in the same manner as in the manufacture of_Organic Electroluminescence Device 3-1 of the invention except for using Compound D-46 in place of Compound i-1.

Manufacture of Organic Electroluminescence Device 10-2 of the Invention:

Organic Electroluminescence Device 10-2 of the invention is manufactured in the same manner as in the manufacture of_Organic Electroluminescence Device 10-1 of the invention except for using Compound 31 of the invention in place of Compound 1 of the invention.

Manufacture of Comparative Device 10-1:

Comparative Device 10-1 is manufactured in the same manner as in the manufacture of Organic Electroluminescence Device 10-1 of the invention except for using Compound M1 in place of Compound 1 of the invention.

Manufacture of Comparative Device 10-2:

Comparative Device 10-2 is manufactured in the same manner as in the manufacture of Organic Electroluminescence Device 10-1 of the invention except for using Compound X1 in place of Compound 1 of the invention.

The organic electroluminescence devices are evaluated in the same manner as in Example 1, and the results obtained are shown in Table 10 below.

TABLE 10

| | External Quantum Efficiency in Relative Value | Driving Durability in Relative Value | Driving Voltage in Relative Value |
|---|---|---|---|
| Organic EL device 10-1 of the invention | 10 | 100 | 10 |
| Organic EL device 10-2 of the invention | 11 | 90 | 11 |
| Comparative device 10-1 | 3 | 8 | 19 |
| Comparative device 10-2 | 3 | 20 | 17 |

Example 11

Manufacture of Organic Electroluminescence Device 11-1 of the Invention:

Organic Electroluminescence Device 11-1 of the invention is manufactured in the same manner as in the manufacture of_Organic Electroluminescence Device 3-1 of the invention except for using Compound D-53 in place of Compound i-1.

Manufacture of Organic Electroluminescence Device 11-2 of the Invention:

Organic Electroluminescence Device 11-2 of the invention is manufactured in the same manner as in the manufacture of_Organic Electroluminescence Device 11-1 of the invention except for using Compound 31 of the invention in place of Compound 1 of the invention.

Manufacture of Comparative Device 11-1:

Comparative Device 11-1 is manufactured in the same manner as in the manufacture of Organic Electroluminescence Device 11-1 of the invention except for using Compound M1 in place of Compound 1 of the invention.

Manufacture of Comparative Device 11-2:

Comparative Device 11-2 is manufactured in the same manner as in the manufacture of Organic Electroluminescence Device 11-1 of the invention except for using Compound X1 in place of Compound 1 of the invention.

The organic electroluminescence devices are evaluated in the same manner as in Example 1, and the results obtained are shown in Table 11 below.

TABLE 11

| | External Quantum Efficiency in Relative Value | Driving Durability in Relative Value | Driving Voltage in Relative Value |
|---|---|---|---|
| Organic EL device 11-1 of the invention | 10 | 100 | 10 |
| Organic EL device 11-2 of the invention | 9 | 100 | 9 |
| Comparative device 11-1 | 3 | 8 | 17 |
| Comparative device 11-2 | 2 | 14 | 33 |

Example 12

Manufacture of Organic Electroluminescence Device 12-1 of the Invention:

Organic Electroluminescence Device 12-1 of the invention is manufactured in the same manner as in the manufacture of_Organic Electroluminescence Device 3-1 of the invention except for using Compound D-54 in place of Compound i-1.

Manufacture of Organic Electroluminescence Device 12-2 of the Invention:

Organic Electroluminescence Device 12-2 of the invention is manufactured in the same manner as in the manufacture of_Organic Electroluminescence Device 12-1 of the invention except for using Compound D-31 of the invention in place of Compound 1 of the invention.

Manufacture of Comparative Device 12-1:

Comparative Device 12-1 is manufactured in the same manner as in the manufacture of Organic Electroluminescence Device 12-1 of the invention except for using Compound M1 in place of Compound 1 of the invention.

Manufacture of Comparative Device 12-2:

Comparative Device 12-2 is manufactured in the same manner as in the manufacture of Organic Electroluminescence Device 12-1 of the invention except for using Compound X1 in place of Compound 1 of the invention.

The organic electroluminescence devices are evaluated in the same manner as in Example 1, and the results obtained are shown in Table 12 below.

TABLE 12

| | External Quantum Efficiency in Relative Value | Driving Durability in Relative Value | Driving Voltage in Relative Value |
|---|---|---|---|
| Organic EL device 12-1 of the invention | 10 | 100 | 10 |
| Organic EL device 12-2 of the invention | 10 | 100 | 8 |
| Comparative device 12-1 | 4 | 10 | 13 |
| Comparative device 12-2 | 4 | 21 | 19 |

According to the present invention, a luminescence device has high emission luminance and high external quantum efficiency, and is excellent in durability. In addition, also in a blue region, the luminescence device in the invention has high emission luminance, emits light in high external quantum efficiency, and is excellent in durability.

The entire disclosure of each and every foreign patent application from which the benefit of foreign priority has been claimed in the present application is incorporated herein by reference, as if fully set forth.

What is claimed is:

1. An organic electroluminescence device comprising:
an anode;
a cathode; and
at least one organic layer,
wherein
the at least one organic layer comprises a first organic layer which is a light-emitting layer being provided between the anode and the cathode and containing at least one light-emitting material, and
the at least one organic layer contains at least one compound represented by formula (I):

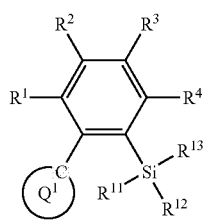

wherein
$Q^1$ represents an aromatic heterocyclic ring;
each of $R^1$, $R^2$, $R^3$ and $R^4$ independently represents a hydrogen atom or a substituent; and
each of $R^{11}$, $R^{12}$ and $R^{13}$ independently represents an alkyl group, an aryl group, or an aromatic heterocyclic group, provided that at least one of $R^{11}$, $R^{12}$ and $R^{13}$ represents an aryl group or an aromatic heterocyclic group.

2. The organic electroluminescence device as claimed in claim 1, wherein
the compound represented by formula (I) is a compound represented by formula (II):

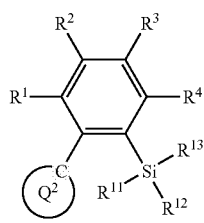

wherein
$Q^2$ represents a nitrogen-containing aromatic heterocyclic ring;
each of $R^1$, $R^2$, $R^3$ and $R^4$ independently represents a hydrogen atom or a substituent; and
each of $R^{11}$, $R^{12}$ and $R^{13}$ independently represents an alkyl group, an aryl group, or an aromatic heterocyclic group, provided that at least one of $R^{11}$, $R^{12}$ and $R^{13}$ represents an aryl group or an aromatic heterocyclic group.

3. The organic electroluminescence device as claimed in claim 1, wherein
the light-emitting layer contains the compound represented by formula (I).

4. The organic electroluminescence device as claimed in claim 1, wherein
the at least one organic layer further comprises a second organic layer being provided between the light-emitting layer and the cathode, and
the second organic layer contains the compound represented by formula (I).

5. The organic electroluminescence device as claimed in claim 1, wherein
the at least one light-emitting material comprises a phosphorescent material.

6. The organic electroluminescence device as claimed in claim 1, wherein
the at least one light-emitting material comprises a platinum complex or an iridium complex.

7. The organic electroluminescence device as claimed in claim 6, wherein
the platinum complex is a platinum complex having a tridentate or tetradentate ligand.

8. The organic electroluminescence device as claimed in claim 7, wherein
the platinum complex is represented by the following formula (C-1):

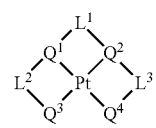

(C-1)

wherein
each of $Q^1$, $Q^2$, $Q^3$ and $Q^4$ independently represents a ligand to coordinate to Pt; and
each of $L^1$, $L^2$ and $L^3$ independently represents a single bond or a divalent linking group.

9. A compound represented by the following formula (III);

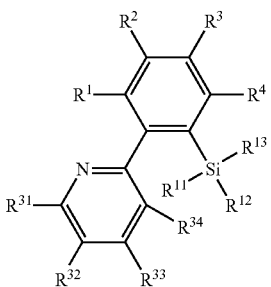

wherein
each of $R^1$, $R^2$, $R^3$ and $R^4$ independently represents a hydrogen atom or a substituent;
each of $R^{11}$, $R^{12}$ and $R^{13}$ independently represents an alkyl group, an aryl group, or an aromatic heterocyclic group, provided that at least one of $R^{11}$, $R^{12}$ and $R^{13}$ represents an aryl group or an aromatic heterocyclic group; and
each of $R^{31}$, $R^{32}$, $R^{33}$ and $R^{34}$ independently represents a hydrogen atom or a substituent.

10. A compound represented by the following formula (IV):

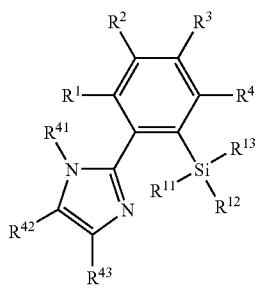

wherein
each of $R^1$, $R^2$, $R^3$ and $R^4$ independently represents a hydrogen atom or a substituent;

each of $R^{11}$, $R^{12}$ and $R^{13}$ independently represents an alkyl group, an aryl group, or an aromatic heterocyclic group, provided that at least one of $R^{11}$, $R^{12}$ and $R^{13}$ represents an aryl group or an aromatic heterocyclic group;

$R^{41}$ represents an alkyl group, an aryl group, or an aromatic heterocyclic group; and each of $R^{42}$ and $R^{43}$ independently represents a hydrogen atom or a substituent.

* * * * *